United States Patent
Mika et al.

(10) Patent No.: US 6,233,487 B1
(45) Date of Patent: May 15, 2001

(54) APPARATUS AND METHOD FOR SETTING THE PARAMETERS OF AN ALERT WINDOW USED FOR TIMING THE DELIVERY OF ETC SIGNALS TO A HEART UNDER VARYING CARDIAC CONDITIONS

(75) Inventors: Yuval Mika, Zichon-Yaacov (IL); David Prutchi, Lake Jackson, TX (US); Ziv Belsky, Haifa (IL); Andre G. Routh, Lake Jackson, TX (US)

(73) Assignee: Impulse Dynamics N.V., Curacao (AN)

( * ) Notice: Subject to any disclaimer, the term of this patent is extended or adjusted under 35 U.S.C. 154(b) by 0 days.

(21) Appl. No.: 09/338,649

(22) Filed: Jun. 23, 1999

Related U.S. Application Data

(63) Continuation-in-part of application No. 09/328,068, filed on Jun. 8, 1999.

(51) Int. Cl.[7] .................................................. A61N 1/362
(52) U.S. Cl. ................................ 607/27; 607/25; 600/510
(58) Field of Search ................................... 607/9, 17, 18, 607/25, 27; 600/510, 521

(56) References Cited

U.S. PATENT DOCUMENTS 4,554,922   11/1985   Prystowsky et al. .

(List continued on next page.)

FOREIGN PATENT DOCUMENTS

WO 97/25098   7/1997   (WO) .

(List continued on next page.)

OTHER PUBLICATIONS

H. Antoni, et al., Polarization Effects of Sinusoidal 50–Cycle Alternating Current on Membrane Potential of Mammalian Cardiac Fibres, Pflugers Arch. 314, pp. 274–291 (1970).

(List continued on next page.)

*Primary Examiner*—Jeffrey R. Jastrzab
(74) *Attorney, Agent, or Firm*—Cowan, Liebowitz & Latman, P.C.; William H. Dippert

(57) ABSTRACT

A method for setting the parameters of an alert time window in an excitable tissue control device operative under a plurality of different cardiac conditions of a heart of a patient. The method includes providing said excitable tissue control device with a set of data including a plurality of sets of alert time window parameters. Each set of window parameters is uniquely associated with a different set of values of a plurality of cardiac condition defining parameters identifying one of the different cardiac conditions. Each set of window parameters includes at least a set of timing parameters usable for obtaining a beginning time point and an ending time point of the alert window. The sets of window parameters are obtained by processing data collected within a data collection session from a plurality of cardiac beats of the same patient under the different cardiac conditions. The methods updates for each current beat cycle the values of a plurality of cardiac condition defining variables corresponding to said cardiac condition defining parameters, automatically selects a current set of alert time window parameters based on the current values of the cardiac condition defining variables, starts and terminates the alert time window based on the time of detecting a first depolarization event at a first cardiac site, detects within the duration of the alert window a second depolarization event at a second cardiac site, and triggers the delivery of a delayed non-excitatory excitable tissue control signal at the second cardiac site based on the time of detection of the second depolarization event. The different cardiac conditions include different beat cycle lengths, and may include beats which are or are not influenced by prior application of ETC signals to the heart and, where relevant, naturally and artificially paced beats. The alert window parameters may include an event detection sensitivity level parameter. Implantable and external devices are describe which are adapted for implementing the disclosed method.

68 Claims, 29 Drawing Sheets

U.S. PATENT DOCUMENTS

| | | |
|---|---|---|
| 4,559,947 | 12/1985 | Renger et al. . |
| 4,830,006 | 5/1989 | Haluska et al. . |
| 4,971,058 | 11/1990 | Pless et al. . |
| 5,083,564 | 1/1992 | Scherlag . |
| 5,154,501 | 10/1992 | Svenson et al. . |
| 5,161,527 | 11/1992 | Nappholz et al. . |
| 5,172,699 | 12/1992 | Svenson et al. . |
| 5,184,620 | 2/1993 | Cudahy et al. . |
| 5,281,219 | 1/1994 | Kallok . |
| 5,391,192 | 2/1995 | Lu et al. . |
| 5,443,485 | 8/1995 | Housworth et al. . |
| 5,443,489 | 8/1995 | Ben-Haim . |
| 5,549,646 | 8/1996 | Katz et al. . |
| 5,683,431 | 11/1997 | Wang . |
| 5,749,906 | 5/1998 | Kieval et al. . |
| 5,782,876 | 7/1998 | Flammang . |
| 5,782,881 | 7/1998 | Lu et al. . |
| 5,800,464 | 9/1998 | Kieval . |
| 5,814,079 | 9/1998 | Kieval . |
| 5,871,506 | 2/1999 | Mower . |

FOREIGN PATENT DOCUMENTS

| | | |
|---|---|---|
| WO 98/10828 | 3/1998 | (WO) . |
| WO 98/10829 | 3/1998 | (WO) . |
| WO 98/10830 | 3/1998 | (WO) . |
| WO 98/10831 | 3/1998 | (WO) . |
| WO 98/10832 | 3/1998 | (WO) . |
| WO 99/03533 | 1/1999 | (WO) . |
| WO 00/57952 | 10/2000 | (WO) . |

OTHER PUBLICATIONS

Classification of Cardiac Arrhythmias Using Fuzzy ART-MAP by Fredric M. Ham and Soowhan Han; IEEE Transactions on Biomedical Engineering, vol. 43, No. 4, Apr. 1996.

Neural–Network–Based Adaptive Matched Filtering for QRS Detection by Quizhen Xue et al. , IEEE Transactions on Biomedical Engineering, vol. 39, No. 4. Apr. 1992.

Identification of Ventricular tachycardia with use of the morphology of the endocardial electrogram by Jonathan J. Langberg. et al. Circulation vol. 77. No. 6, Jun. 1988.

APPARATUS AND METHOD FOR SETTING THE PARAMETERS OF AN ALERT WINDOW USED FOR TIMING THE DELIVERY OF ETC SIGNALS TO A HEART UNDER VARYING CARDIAC CONDITIONS

RELATED U.S. PATENT APPLICATIONS

This Application is a continuation in part of U.S. patent application Ser. No. 09/328,068, to Mika et al., titled "APPARATUS AND METHOD FOR COLLECTING DATA USEFUL FOR DETERMINING THE PARAMETERS OF AN ALERT WINDOW FOR TIMING DELIVERY OF ETC SIGNALS TO A HEART UNDER VARYING CARDIAC CONDITIONS", filed Jun. 8, 1999, the entire specification of which is incorporated herein by reference.

FIELD OF THE INVENTION

The present invention relates generally to the field of methods and medical devices for modulating cardiac muscle activity and contractility and more specifically to methods and devices for setting the parameters of a detection time window used for initiating the delivery of excitable tissue controller (ETC) signals under a variety of conditions including varying heart rates, paced or sensed beats and the absence and presence of ETC signals' effects on the velocity of propagation of a cardiac depolarization wave.

BACKGROUND OF THE INVENTION

Excitable tissue controllers (ETCs) are devices which modulate the activity of excitable tissues by application of non-excitatory electrical stimulation to the excitable tissue through suitable electrodes in contact with the tissue. For example, ETC devices may be used, inter alia, to increase or decrease the contractility of cardiac muscle in vitro, in vivo and in situ., as disclosed in detail in PCT application, International Publication Number WO 97/25098 to Ben-Haim et al., titled "ELECTRICAL MUSCLE CONTROLLER", incorporated herein by reference. Other methods and applications of ETC devices are disclosed in PCT applications commonly-assigned to the assignee of the present application, International Publication Number WO 98/10828, titled "APPARATUS AND METHOD FOR CONTROLLING THE CONTRACTILITY OF MUSCLES" to Ben Haim et al., incorporated herein by reference, International Publication Number WO 98/10829, titled "DRUG-DEVICE COMBINATION FOR CONTROLLING THE CONTRACTILITY OF MUSCLES" to Ben Haim et al., incorporated herein by reference and International Publication Number WO 98/10830, titled "FENCING OF CARDIAC MUSCLES" to Ben Haim et al., incorporated herein by reference, International Publications Number WO 98/10831 to Ben Haim et al., titled "CARDIAC OUTPUT CONTROLLER", incorporated herein by reference.

Further applications of the ETC including devices combining cardiac pacing and cardiac contractility modulation are disclosed in PCT Application, International Publication No. WO 98/10832, titled "CARDIAC OUTPUT ENHANCED PACEMAKER" to Ben Haim et al., co-assigned to the assignee of the present application. Such ETC devices function by applying non-excitatory electrical field signals of suitable amplitude and waveform, appropriately timed with respect to the heart's intrinsic electrical activity to selected cardiac segments. The contraction of the selected segments can be modulated to increase or decrease the stroke volume of the heart. The timing of the ETC signals must be carefully controlled since application of the ETC signal to the myocardium at inappropriate times may be arrhythmogenic. The ETC signals must therefore be applied to the selected cardiac segment within a defined time interval during which the selected cardiac segment will not be stimulated by the ETC signals.

As disclosed in International Publication No. WO 98/10832, the ETC signals may be timed relative to a trigger signal which is also used as a pacing trigger, or may be timed relative to locally sensed electrogram signals.

U.S. patent application to Mika et al., Ser. No. 09/276,460, Titled "APPARATUS AND METHOD FOR TIMING THE DELIVERY OF NON-EXCITATORY ETC SIGNALS TO A HEART", filed Mar. 25, 1999 and assigned to the common assignee of the present application, the entire specification of which is incorporated herein by reference, discloses a method for timing the delivery of non-excitatory ETC signals to a heart using, inter alia, an alert window period for reducing the probability of delivering an improperly timed ETC signal to the heart due to spurious detection of noise or ectopic beats.

The methods of timing of the delivery of ETC signals disclosed hereinabove do not take into account the fact that naturally occurring and pacemaker induced changes in heart rate (HR) may cause changes in the velocity of propagation of the depolarization wave in the myocardium. Additionally, the delivery of the ETC signals to the myocardium may also cause changes in the velocity of propagation of the depolarization wave in the myocardium. Other factors such as, inter alia, various cardio-active drug treatments and myocardial pathological conditions such as ischemia may also cause changes in the velocity of propagation of the depolarization wave in the myocardium. It is therefore desirable to have a method for determining proper timing of the delivery of ETC signals which takes into account variations in velocity of propagation of the depolarization wave in the myocardium under different cardiac conditions.

SUMMARY OF THE INVENTION

There is therefore provided, in accordance with a preferred embodiment of the present invention, a method for setting the parameters of an alert time window in an excitable tissue control device operative under a plurality of different cardiac conditions of a heart of a patient. The method includes the step of providing the excitable tissue control device with a set of data. The set of data includes a plurality of sets of alert time window parameters. Each set of alert time window parameters is associated with one of the plurality of different cardiac conditions. Each set of alert time window parameters includes at least a set of timing parameters usable for obtaining a beginning time point and an ending time point for the alert time window. Each set of the plurality of sets of alert time window parameters is obtained by processing data collected from a plurality of cardiac beats of the heart of the patient under the plurality of different cardiac conditions within a data collection session prior to the step of providing. The method further includes the step of automatically selecting, for a current beat cycle of the heart, a current set of alert time window parameters of the plurality of sets of alert time window parameters based on the current cardiac conditions detected for the current beat cycle. The method further includes the step of using, for the current beat cycle, the current set of alert time window parameters selected in the step of automatically selecting to start and terminate the alert time window based on the time of detecting a first depolarization event at or about a first cardiac site. The method further includes the steps of detecting, within the duration of the alert time window of the current beat cycle, a second depolarization event at a second cardiac site of the heart, and triggering the delivery of a delayed non-excitatory excitable tissue control signal at or about the second cardiac site based on the time of detection of the second depolarization event.

There is further provided, in accordance with a preferred embodiment of the present invention, a method for setting the parameters of an alert time window in an excitable tissue control device operative under a plurality of different cardiac conditions of a heart of a patient. The method includes the step of providing the excitable tissue control device with a set of data. The set of data includes a plurality of sets of alert time window parameters. Each set of alert time window parameters is uniquely associated with a different set of values of a plurality of cardiac condition defining parameters identifying one of the plurality of different cardiac conditions. Each set of alert time window parameters of the plurality of sets of alert time window parameters includes at least a set of timing parameters usable for obtaining a beginning time point and an ending time point for the alert time window. Each set of alert time window parameters is obtained by processing data collected from a plurality of cardiac beats of the heart of the patient under the plurality of different cardiac conditions within a data collection session prior to the step of providing. The method further includes the step of updating for a current beat cycle of the heart the values of a plurality of cardiac condition defining variables corresponding to the cardiac condition defining parameters. The method further includes the step of automatically selecting for the current beat cycle a current set of alert time window parameters of the plurality of sets of alert time window parameters based on the current values of the cardiac condition defining variables. The method further includes the step of using, for the current beat cycle, the current set of alert time window parameters selected in the step of automatically selecting to start and terminate the alert time window based on the time of detecting a first depolarization event at or about a first cardiac site. The method further includes the steps of detecting within the duration of the alert time window of the current beat cycle a second depolarization event at a second cardiac site of the heart, and triggering the delivery of a delayed non-excitatory excitable tissue control signal at or about the second cardiac site based on the time of detection of the second depolarization event.

There is also provided, in accordance with a preferred embodiment of the present invention, an excitable tissue control device for setting, on a beat by beat basis, the parameters of an alert time window under a plurality of different cardiac conditions of a heart of a patient. The device includes a plurality of electrodes implanted in or about the heart. The device further includes detection circuitry for detecting electrical depolarization events in a first cardiac site through at least a first electrode of the plurality of electrodes. The first electrode is disposed in or about the first cardiac site. The detection circuitry is also used for detecting electrical depolarization events in a second cardiac site through at least a second electrode of the plurality of electrodes. The second electrode is disposed in or about the second cardiac site. The device further includesan excitable tissue control unit for delivering non-excitatory excitable tissue control signals to at least part of the second cardiac site through one or more electrodes of the plurality of electrodes. The device further includes a memory unit for storing a set of data. The set of data includes a plurality of sets of alert time window parameters. Each set of alert time window parameters is uniquely associated with a different set of values of a plurality of cardiac condition defining parameters identifying one of the plurality of different cardiac conditions. Each set of alert time window parameters includes at least a set of timing parameters usable for obtaining a beginning time point and an ending time point for the alert time window. Each set of alert time window parameters is obtained by processing data collected from a plurality of cardiac beats of the heart of the patient under the plurality of different cardiac conditions within a data collection session performed in the patient. The device further includes a processor unit operatively connected to the detection circuitry, the excitable tissue control unit and the memory unit. The processor unit is usable for receiving detection signals from the detection circuitry, for controlling the excitable tissue control unit by using the received detection signals, for updating in a current beat cycle of the heart the values of a plurality of cardiac condition defining variables corresponding to the cardiac condition defining parameters, for automatically selecting for the current beat cycle a current set of alert time window parameters of the plurality of sets of alert time window parameters based on the current values of the cardiac condition defining variables, for applying the current set of alert time window parameters to start the alert time window within the current beat cycle after detecting a first depolarization event at or about the first cardiac site and to terminate the alert time window, and for initiating the delivery of a delayed excitable tissue control signal at or about the second cardiac site upon detecting, within the duration of the alert time window, a depolarization event in or about the second cardiac site of the heart. The device further includes a power source for providing power to the detection circuitry, the processor unit the memory unit and the excitable tissue control unit.

Furthermore, in accordance with another preferred embodiment of the present invention, the device further includes a telemetry unit operatively connected to the power source and the processor unit for telemetrically receiving data from a second telemetry unit disposed outside the patient.

Furthermore, in accordance with another preferred embodiment of the present invention, the plurality of sets of alert time window parameters of the set of data are stored in the memory unit as a data array or a look up table.

Furthermore, in accordance with another preferred embodiment of the present invention, the detection circuitry is adapted for being controllably switched between a plurality of detection sensitivity levels, and each set of alert time window parameters of the plurality of sets of alert time window parameters further includes at least one detection sensitivity parameter having a value representing one of the plurality of detection sensitivity levels of the detection circuitry, and the processor unit is adapted for using the value of the at least one detection sensitivity parameter of the current beat cycle to switch the detection circuitry to a detection sensitivity level represented by the at least one detection sensitivity parameter of the current beat cycle.

Furthermore, in accordance with another preferred embodiment of the present invention, the detection circuitry is adapted for being switched between a plurality of voltage threshold levels and the at least one detection sensitivity parameter includes a voltage threshold level.

Furthermore, in accordance with another preferred embodiment of the present invention, the detection circuitry is adapted for performing event detection based on a morphological detection method and wherein the at least one detection sensitivity parameter includes at least one morphological detection parameter.

Furthermore, in accordance with another preferred embodiment of the present invention, the set of data is a degenerate set of data in which at least some of the sets of alert time window parameters of the plurality of sets of alert time window parameters have identical values of the at least one detection sensitivity parameter.

Furthermore, in accordance with another preferred embodiment of the present invention, the plurality of cardiac conditions includes beats having a plurality of different beat to beat time intervals representing different instantaneous heart rates of the heart.

Furthermore, in accordance with another preferred embodiment of the present invention, the plurality of cardiac conditions further includes beats occurring during a time period in which the prior application of excitable tissue control signals results in a change of the velocity of propagation of a depolarization wave in at least a portion of the myocardial tissue disposed between the first cardiac site and the second cardiac site of the heart, and beats occurring during a time period in which the prior application of excitable tissue control signals does not result in a change in the velocity of propagation of a depolarization wave in at least a portion of the myocardial tissue disposed between the first cardiac site and the second cardiac site of the heart.

Furthermore, in accordance with another preferred embodiment of the present invention, the device further includes a pacing unit operatively connected to the power source, the processor unit and to at least one electrode of the plurality of electrodes, for delivering pacing pulses to the heart through the at least one electrode.

Furthermore, in accordance with another preferred embodiment of the present invention, the plurality of cardiac conditions includes beats initiated by the natural pacemaker of the heart and beats initiated by a pacing pulse delivered by the excitable tissue control device.

Furthermore, in accordance with another preferred embodiment of the present invention, the set of timing parameters of the alert time window parameters includes a beginning time point value and an ending time point value for the alert time window.

Furthermore, in accordance with another preferred embodiment of the present invention, the excitable tissue control device is provided with a value of the bin duration of a time bin used for collecting data within the data collection session. The value is stored in the memory unit. The set of timing parameters of the alert time window parameters includes a starting bin number and an ending bin number, and the processor unit is adapted for computing the starting time point and ending time point of the alert time window from the bin duration, the starting bin number and the ending bin number, prior to starting of the alert time window within the current beat cycle.

Furthermore, in accordance with another preferred embodiment of the present invention, the set of timing parameters includes a set of approximation parameters and wherein the processing of the data collected from the heart in the data collection session includes using an approximation method to obtain a plurality of sets of approximation parameters usable for computing improved approximated values of the beginning time point and the ending time point of the alert time window.

Furthermore, in accordance with another preferred embodiment of the present invention, the approximation method is a linear piecewise approximation method. The set of approximation parameters includes a beginning time point parameter and a first slope parameter associated with the beginning time point parameter. The set of approximation parameters also includes an ending time point parameter and a second slope parameter associated with the ending time point parameter. The step of using includes computing an approximated beginning time point for the alert time window of the current beat cycle from the values of the current cycle length measured for the current beat cycle, the first slope parameter and the beginning time point parameter, and computing an approximated ending time point for the alert time window of the current beat cycle from the values of the current cycle length, the second slope parameter and the ending time point parameter.

Furthermore, in accordance with another preferred embodiment of the present invention, the current cycle length is the instantaneous cycle length determined from the current R—R interval or the current A—A interval measured for the current beat cycle.

Furthermore, in accordance with another preferred embodiment of the present invention, the current cycle length is an average cycle length computed from the values of a plurality of consecutive R—R intervals including the R—R interval of the current beat cycle.

Furthermore, in accordance with another preferred embodiment of the present invention, the current cycle length is an average cycle length computed from the values of a plurality of consecutive A—A intervals including the A—A interval of the current beat cycle.

Furthermore, in accordance with another preferred embodiment of the present invention, the set of data is a degenerate set of data in which at least some of the sets of alert time window parameters of the plurality of sets of alert time window parameters have identical values of the set of timing parameters.

Furthermore, in accordance with another preferred embodiment of the present invention, the first cardiac site is the right ventricle of the heart and the second cardiac site is the left ventricle of the heart.

Furthermore, in accordance with another preferred embodiment of the present invention, the first cardiac site is the right atrium of the heart and the second cardiac site is the left ventricle of the heart.

Furthermore, in accordance with another preferred embodiment of the present invention, the excitable tissue control device is implanted in the patient.

Furthermore, in accordance with another preferred embodiment of the present invention, the excitable tissue control device is disposed out of the patient and is operatively connected to the plurality of electrodes implanted in or about the heart of the patient.

There is also provided, in accordance with a preferred embodiment of the present invention, an excitable tissue control device for setting on a beat by beat basis the parameters of an alert time window under a plurality of different cardiac conditions of a heart of a patient. The device includes a plurality of electrodes implanted in or about the heart. The device also includes means for detecting electrical depolarization events in a first cardiac site through at least a first electrode disposed in or about the first cardiac site, and for detecting electrical depolarization events in a second cardiac site through at least a second electrode disposed in or about the second cardiac site. The device also includes excitable tissue control means for delivering non-excitatory excitable tissue control signals to at least part of the second cardiac site through one or more electrodes of the plurality of electrodes. The device also includes memory means for storing a set of data. The set of data includes a plurality of sets of alert time window parameters. Each set of alert time window parameters is uniquely associated with a different set of values of a plurality of cardiac condition defining parameters identifying one of the plurality of different cardiac conditions. Each set of alert time window parameters includes at least a set of timing parameters usable for obtaining a beginning time point and an ending time point for the alert time window. Each set of alert time window parameters is obtained by processing data collected from a plurality of cardiac beats of the heart of the patient under the plurality of different cardiac conditions within a data collection session performed in the patient. The device also includes processing means operatively connected to the detection means, the excitable tissue control means and the memory means. The processing means are used for receiving detection signals from the detection means, for controlling the excitable tissue control means by using the received detection signals, for updating in a current beat cycle of the heart the values of a plurality of cardiac condition defining variables corresponding to the cardiac condition defining parameters, for automatically selecting for the current beat cycle a current set of alert time window parameters of the plurality of sets of alert time window parameters based on the current values of the cardiac condition defining variables, for applying the current set of alert time window parameters to start the alert time window within the current beat cycle after detecting a first depolarization event at or about the first cardiac site and to terminate the alert time window, and for initiating the delivery of a delayed excitable tissue control signal at or about the second cardiac site upon detecting within the duration of the alert time window a depolarization event in or about the second cardiac site of the heart. The device also includes a power source for providing power to the detection means, the processing means the memory means and the excitable tissue control means.

Furthermore, in accordance with another preferred embodiment of the present invention, the device further includes telemetry means operatively connected to the power source and the processing means for telemetrically receiving data from a second telemetry means disposed outside the patient.

Finally, in accordance with another preferred embodiment of the present invention, the device further includes pacing means operatively connected to the power source, the processing means and to at least one electrode of the plurality of electrodes, for delivering pacing pulses to the heart through the at least one electrode.

BRIEF DESCRIPTION OF THE DRAWINGS

The invention is herein described, by way of example only, with reference to the accompanying drawings, in which like components are designated by like reference numerals, wherein.

DETAILED DESCRIPTION OF THE INVENTION

Notation Used Throughout

The following notation is used throughout this document.

| Term | Definition |
| --- | --- |
| RV | Right ventricle |
| LV | Left ventricle |
| SE | Sensed Event |
| PE | Paced Event |
| ETC | Excitable Tissue Control |
| PVC | Premature Ventricular Contraction |
| IEGM | Intra-cardiac Electrogram |
| SVC | Superior Vena Cava |
| GCV | Great Cardiac Vein |
| CS | Coronary Sinus |
| PAC | Premature Atrial Contraction |

Method of timing of ETC signal delivery

Typically, ETC signal delivery is timed relative to a sensed signal representing the depolarization wave locally sensed at or near the site of the electrodes used for ETC signal delivery. This signal may be a biphasic or polyphasic intra-cardiac electrogram (IEGM) signal sensed by a lead or catheter including one or more electrodes capable of sensing an IEGM signal and of delivering pacing pulses. The depolarization wave represented by the IEGM is an electrical event caused by spreading myocardial electrical excitation evoked by the natural pacemaker of the heart (normally the Sino-atrial node) in which case the event is referred to as a sensed event (SE), or by a pacing pulse delivered to the myocardium by, in which case the event is referred to as a paced event (PE). The IEGM signal may also include electrical depolarizations caused by ectopic myocardial activation such as premature atrial contractions (PAC) or premature ventricular contraction (PVC). Furthermore, the IEGM signal may include artifacts caused by electrical noise.

Figure 1:
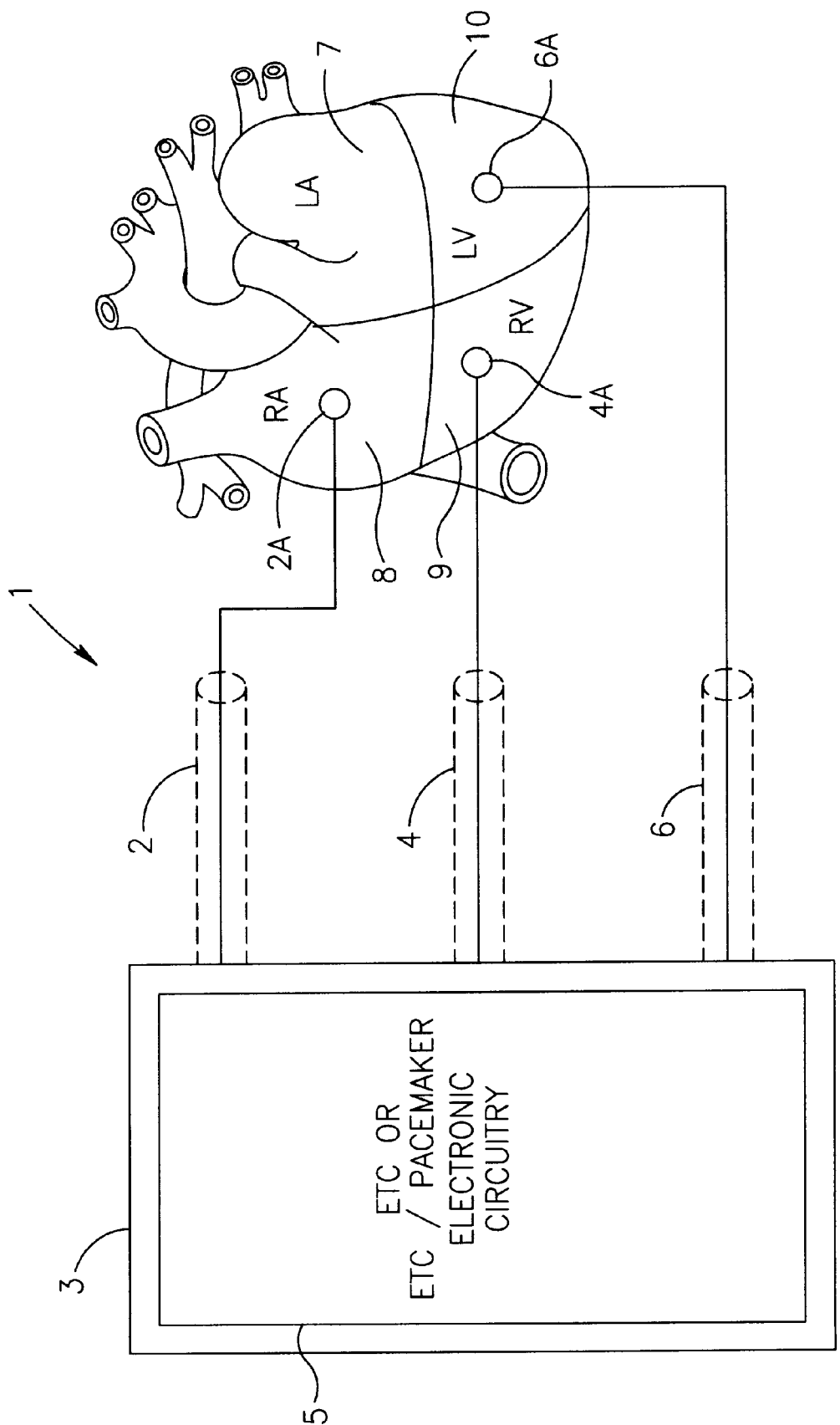
FIG. 1 is a schematic diagram representing a typical lead placement configuration of a pacemaker/ETC device within the heart, in accordance with a preferred embodiment of the present invention.

Reference is now made to FIG. 1 which is a schematic diagram representing a typical lead placement configuration of a pacemaker/ETC device within the heart, in accordance with a preferred embodiment of the present invention. The term pacemaker/ETC device generally refers throughout the present application to a device capable of pacing a heart and of delivering non-excitatory ETC signals to the heart. The Pacemaker/ETC device 1 includes an implantable housing or case 3 for housing the electronic circuitry 5 (not shown in detail in FIG. 1) of the device 1. A pacing/sensing lead 2 is suitably connected to the case 3 and operatively connected to the circuitry 5.

The lead 2 includes an electrode 2A applied to the right atrium (RA) 8. The electrode 2A is used for sensing SEs and for delivering pacing pulses if necessary. The left atrium 7 (LA) is also shown in FIG. 1. The pacing lead 2 may be inserted into the RA 8 through the subclavian vein and the superior vena cava (SVC), but other methods of insertion are also possible. Another pacing/sensing lead 4 is connected to the case 3 and operatively connected to the circuitry 5. The lead 4 includes an electrode 4A which is applied the right ventricle (RV) 9 and is used for sensing right ventricular SEs and PEs and for delivering pacing pulses if necessary. The lead 4 may be inserted into the RV through the subclavian vein and the superior vena cava (SVC), but other methods of insertion are also possible. A third lead 6 is also suitably connected to the case 3 and operatively connected to the circuitry 5. The lead 6 includes an electrode 6A which is applied to the wall of a lateral vein of the great cardiac vein (GCV) and is used for local sensing of SEs and PEs in the left ventricle (LV) 10 and for delivering non-excitatory ETC signals to the LV 10 if required.

The lead 6 may be inserted through the sub-clavian vein, passing through the SVC, the right atrium, the coronary sinus (CS) and the GCV and reaching a lateral vein of the GCV, but other methods of insertion of the leads 6 into or about the left ventricle (LV) are also possible. The implantable case 3 is typically implanted in a thoracic subcutaneous pocket (not shown), but other implantation positions are also possible. It is noted that the above disclosed lead placements and insertion paths and the case placement are given by way of example only and that other electrode placements and lead insertion paths and case placements are also possible.

It is noted that while each of the single electrodes 2A, 4A and 6A of the device 1 of FIG. 1 may be used for sensing with respect to a common reference point such as the case 3 of the device 1, other preferred embodiments of the present invention may use pairs of locally applied electrodes (not shown) which may be used for local differential sensing. For example, The lead 2 may include a pair of electrodes (not shown) which are applied to the RA 8 for local sensing, the lead 4 may include a pair of electrodes (not shown) which are applied to the RV 9 for local sensing and the lead 6 may include a pair of electrodes (not shown) which are applied to the LV 10 for local sensing.

It is further noted that while the electrode 2A of the lead 2 is used for both sensing and pacing the RA 8, in other preferred embodiments of the present invention the lead 2 may include additional electrodes or electrode pairs (not shown) such that one or more electrode or electrode pair is used for sensing in the RA 8 while other separate electrode (s) or electrode pairs are used for pacing the RA 8. Similarly, In accordance with a preferred embodiment of the present invention, The lead 4 may include more than one electrode or pair of electrodes (not shown) which may be separately used for sensing and for pacing the right ventricle 9. Yet similarly, The lead 6 may include more than one electrode or electrode pairs (not shown) of which one or more electrode or electrode pair is used for sensing in the left ventricle 10 and one or more additional electrodes or electrode pairs are used for delivering non-excitatory ETC signals to the left ventricle 10.

It will therefore be appreciated by those skilled in the art, that the number and arrangement of the electrodes within the leads 2,4 and 6 may be varied in many ways and many combinations all being within the scope and spirit of the present invention.

Various types of electrodes and electrode positioning methods known in the art may be used for sensing and pacing and for delivering ETC signals to the heart. One or more of the electrodes or electrode pairs 2A, 4A and 6A may be implanted within a cardiac chamber and placed in contact with the endocardium as disclosed hereinabove. One or more of the electrodes or electrode pairs 2A, 4A and 6A may also be disposed within a cardiac blood vessel, such as a lateral vein of the GCV or another suitable cardiac blood vessel, and used for sensing and/or pacing and/or delivering ETC signals to the myocardial tissue adjacent to or in contact with the blood vessel wall. One or more of the electrodes or electrode pairs 2A, 4A and 6A may also be epicardial electrodes which may be epicardially applied to the heart as is well known in the art.

Typically, ETC signals are delivered to the left ventricle via the electrode(s) 6A of lead 6. The timing of the ETC signal is triggered by locally sensing in the LV the depolarization wave of the PE or the SE. Preferably, a separate sensing electrode (not shown) which is also included within the lead 6 and is positioned in the vicinity of the electrode(s) 6A, is used for the local sensing in or about the LV 10, since the type and surface area optimal for sensing electrodes are usually different than the type and surface area of electrodes which are optimized for delivering the relatively large currents of ETC signals. However, It may also be possible to use the same electrode (or electrodes) 6A for delivering the ETC signal and for locally sensing the depolarization wave in or about the LV 10.

To facilitate correct timing of the ETC delivery, measures need to be taken so that ETC signal delivery is not triggered by local LV sensing of noise, premature ventricular contractions (PVCs), premature atrial contractions (PACs) or by delayed sensing of remote events such as a right ventricular depolarization. One possible approach is the restricting of the local sense triggering for ETC delivery to a predefined time window.

The use of a predefined time window for other different purposes such as to detect activation for capture verification in pacemakers is known in the art. U.S. Pat. No. 5,443,485 to Housworth et al. discloses the use of a timing window to detect a paced stimulation pulse for achieving capture verification to ensure that the pacing pulse energy is high enough.

U.S. Pat. No. 5,683,431 to Wang discloses a method for performing pacemaker capture verification using electrodes different than the pacing electrodes to sense the activation evoked by the pacing pulse.

U.S. Pat. No. 5,391,192 to Lu et al. discloses a method for externally determining the minimum energy of a pacing pulse for capture verification using window based detection of activation.

Figure 2:
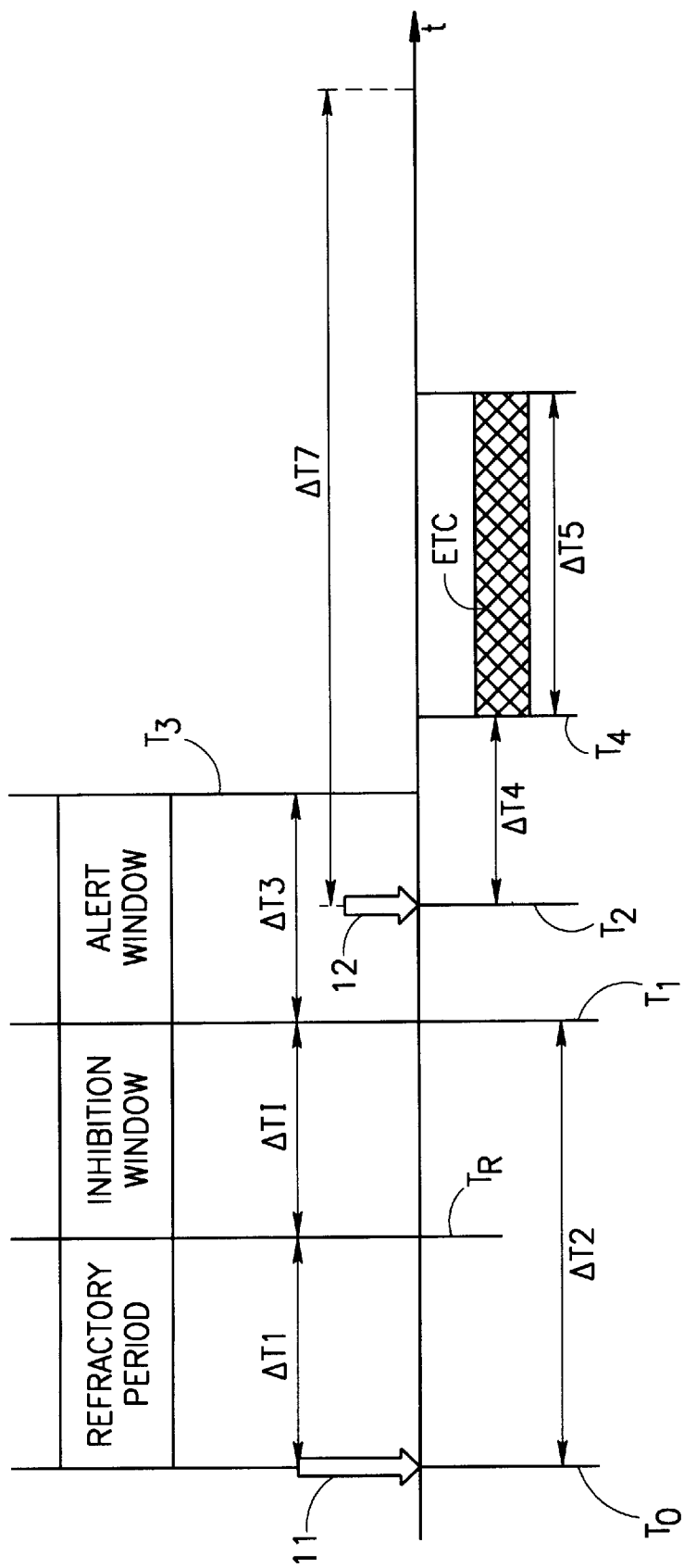
FIG. 2 is a schematic diagram useful in understanding a method using an alert window for timing the delivery of ETC signals useful in operating the device of FIG. 1, in accordance with a preferred embodiment of the present invention.

Reference is now made to FIG. 2 which is a schematic diagram useful in understanding a method using an alert window for timing the delivery of ETC signals useful in operating the device of FIG. 1, in accordance with a preferred embodiment of the present invention. The detection time window is referred to as the "alert window" throughout the present application.

The horizontal axis of FIG. 2 represents time. The arrow labelled 11 schematically represents the timing of a depolarization event 11 locally sensed in the RV by one or more electrodes (not shown) of the lead 4 of FIG. 1. The time $T_0$ represents the time of detection of the RV event. Typically, the time $T_0$ represents the time point at which a threshold crossing occurs. However, $T_0$ may also represent the time of event detection obtained by other methods known in the art for cardiac event detection such as detection methods based on the shape of the signal (also known as signal morphology based detection methods) or other suitable detection methods known in the art. The RV event 11 may represent a locally sensed RV depolarization initiated by a naturally occurring SA node evoked atrial event (not shown) or initiated by artificial atrial pacing. The RV event 11 may also represent a locally sensed RV depolarization initiated by a pacing pulse delivered to the RV through an electrode (not shown) included in the lead 4 of FIG. 1. After the time $T_0$, a local sense "refractory" period labeled $\Delta T1$ begins. The refractory period $\Delta T1$ ends at time $T_R$. During the refractory period $\Delta T1$ no sensing is performed. This refractory period is used to avoid the electrical pacing artifact due to electrode polarization and/or electrode cross-talk. The refractory period may also be useful in avoiding electrical artifacts due to far field sensing as is well known in the art.

Typically, the duration of the refractory period $\Delta T1$ is approximately 10–15 milliseconds but other values may be used depending, inter alia, on the specific application, electrode type, and detection method used. It is noted that, in accordance with one preferred embodiment of the present invention, the value of the refractory period duration may be set to $\Delta T1=0$. In such an embodiment no refractory period $\Delta T1$ is implemented.

A local sense alert window having a duration $\Delta T3$ starts at time $T_1$ and ends at time $T_3$. The time interval between time points $T_0$ and $T_1$ is defined as the alert window delay interval $\Delta T2$ which is the delay between time of detection of the depolarization event 11 and the beginning of the alert window $\Delta T3$.

The arrow labeled 12 of FIG. 2 schematically represents the occurrence of a depolarization event locally sensed in the LV. For example, the locally sensed event 12 may be sensed by a sensing electrode (not shown) or by an ETC signal delivery electrode (not shown) included within the lead 6 of FIG. 1. The time $T_2$ represents the time of detection of the LV depolarization event 12. Typically, the time $T_2$ represents the time point at which a threshold crossing occurs as is disclosed hereinbelow. However, $T_2$ may also represent the time of event detection obtained by other methods known in the art for cardiac event detection.

An article titled "NEURAL NETWORK BASED ADAPTIVE MATCHED FILTERING FOR QRS DETECTION" by Xue et al., published in IEEE Transactions on Biomedical engineering, Vol. 39, No. 4 pp. 317–329 (1992) and incorporated herein by reference, discloses an adaptive matched filtering algorithm based on an artificial neural network for QRS detection.

An article titled "IDENTIFICATION OF VENTRICULAR TACHYCARDIA WITH USE OF THE MORPHOLOGY OF THE ENDOCARDIAL ELECTROGRAM" by Langberg et al., published in Circulation, Vol. 77, No. 6 pp. 1363–1369 (1988) and incorporated herein by reference, discloses the application of a template to derive morphological parameters of unipolar and bipolar electrogram signals for detecting tachycardia.

An article titled "CLASSIFICATION OF CARDIAC ARRHYTHMIAS USING FUZZY ARTMAP" by F. M. Ham and S. Han, published in IEEE Transactions on Biomedical engineering, Vol. 43, No. 4 pp. 425–430 (1996) and incorporated herein by reference, discloses the use of a fuzzy adaptive resonance theory mapping (ARTMAP) neural net classifier for classifying QRS complexes under normal and abnormal conditions.

U.S. Pat. No. 5,782,876 to Flammang titled "METHOD AND APPARATUS USING WINDOWS AND AN INDEX VALUE FOR IDENTIFYING CARDIAC ARRHYTHMIAS", incorporated herein by reference, discloses the use of the sensed electrogram slope (derivative of ECG) for morphological electrogram detection in a device for identifying cardiac arrhythmias.

The above referenced morphological signal detection methods, as well as other signal morphology based detection methods known in the art, may be adapted for detection of the depolarization events within the IEGM signals of the present invention.

The detection of the LV sensed event 12 at time $T_2$ triggers the delivery of an ETC signal represented by the cross hatched area labeled ETC. The ETC signal starts at a time point $T_4$ separated from $T_2$ by a delay interval $\Delta T4$. The ETC signal has a duration $\Delta T5$.

Preferably, the value of the duration of the ETC signal $\Delta T5$ is a variable duration and may vary from one beat cycle to another in accordance with the required modification of myocardial contractility. Typically, the duration and or other parameters of the ETC signal may be modified based on the current value of the heart rate. The methods for determining the required ETC signal duration $\Delta T5$ are not the subject matter of the present invention and will not be disclosed in detail hereinafter.

It is noted that, in accordance with other preferred embodiments of the present invention, the duration of the ETC signal $\Delta T5$ may be a constant value which does not vary from one beat cycle to another beat cycle.

The ETC signals may have various waveforms, durations and intensities as disclosed in detail by Ben Haim et al. in the above referenced International Publications No. WO 97/25098, WO 98/10828, WO 98/10829, WO 98/10830, WO 98/10831 and WO 98/10832. The characteristics of the delivered ETC signals are not the subject of the present invention and will not be further discussed hereinafter.

Only a locally sensed depolarization event detection occurring within the duration of the alert window $\Delta T3$ is used to trigger an ETC signal. The detection of an electrical depolarization event happening outside the alert window will not result in triggering of an ETC signal. This has the advantage of reducing the probability of delivering an improperly timed ETC signal due to electrical noise occurring outside the preset duration of the alert window $\Delta T3$. However, if a depolarization event (not shown) due to an ectopic beat is detected between the time $T_0$ and the time $T_1$ in a case where the refractory period $\Delta T1$ is not used, or between the time $T_R$ and the time $T_1$ in a case where the refractory period $\Delta T1$ is used, and then a later depolarization event (not shown) is detected within the duration of the alert window $\Delta T3$, the triggering of an ETC signal by the later occurring depolarization event may result in an improperly timed ETC signal. Therefore, In order to prevent such improper timing, the timing method may further include an inhibitory window $\Delta TI$. Any depolarization event which is detected within the duration of the inhibition window $\Delta TI$ will result in the inhibiting of ETC signal delivery within the current beat cycle as disclosed in detail hereinbelow.

In accordance with one preferred embodiment of the present invention, $\Delta TI = \Delta T2 - \Delta T1$, in such a preferred embodiment the inhibition window $\Delta TI$ starts at the end of the refractory period $\Delta T1$ and ends at the beginning of the alert window $\Delta T3$. If no refractory period is used ($\Delta T1=0$), the inhibition window spans the entire alert window delay interval $\Delta T2$. However, in accordance with other preferred embodiments of the timing method of present invention, the end of the inhibition period $\Delta TI$ may be separated from the beginning of the alert window $\Delta T3$ by an intermediate time interval (not shown in FIG. 2 for the sake of clarity of illustration). The detection of a depolarization event within the duration of such an intermediate time interval will not result in the inhibition of triggering of an ETC signal by a later depolarization event detected within the duration of the alert window $\Delta T3$.

If a depolarization event was detected in the IEGM signal which is locally sensed in the left ventricle 10 within the duration of the inhibition window $\Delta TI$, ETC signal delivery is inhibited such that later occurrence of a depolarization event within a preset "inhibition refractory period" (not shown in FIG. 2 for the sake of clarity of illustration) of the current beat cycle will not result in a delivery of an ETC signal. This feature has the advantage that it reduces the probability of erroneous detection of spurious noise or of ectopic beats such as PVCs or PACs and the subsequent triggering of the delivery of an incorrectly timed ETC signal. The details of the implementation of the inhibition refractory period are disclosed in detail in co-pending U.S. patent application to Mika et al., Ser. No. 09/276,460, Titled "APPARATUS AND METHOD FOR TIMING THE DELIVERY OF NON-EXCITATORY ETC SIGNALS TO A HEART", filed Mar. 25, 1999.

Typically, the local sensing sensitivity is adjusted such that, only events of a certain amplitude will be detected. This is achieved by setting a detection threshold. Threshold crossing detection methods for electrical signals are well known in the art and are not the subject matter of the present invention. Such threshold crossing detection methods are commonly used in pacemakers for sensed event detection.

Briefly, any acceptable detection method based on threshold crossing of one or more threshold levels may be used with the present invention. For example, the sensed electrogram may be biphasic, and two threshold levels may be used including a positive threshold level and a negative threshold level. Alternatively, full wave rectification of the electrogram may be used to obtain a signal which is positive only, such that a single positive threshold level may be used. Additionally, other methods of detection may be used which are based on signal morphology as disclosed in detail hereinabove.

Since multiple threshold crossings may occur during the same depolarization event or during noise signals, ambiguity may arise as to which threshold crossing should be used as the trigger. This may be solved by triggering by the first threshold crossing in the window and by implementing an "alert refractory period" $\Delta T7$ following the first threshold crossing of the LV sensed event 12 at time $T_2$ to prevent multiple triggering by multiple threshold crossings occurring within a single depolarization wave representing a single event. The alert refractory period $\Delta T7$ starts at the time $T_2$ and has a fixed duration represented by the double headed arrow labeled $\Delta T7$. During the alert refractory period $\Delta T7$ no sensing is performed so that additional triggering cannot happen during the period $\Delta T7$.

It is noted that, since the first threshold crossing due to an LV sensed event 12 may happen at any time during the alert window $\Delta T3$, and since the duration of the ETC signal $\Delta T5$ may be varied from one beat cycle to another (for varying the effects of the ETC signal on myocardial contraction), the duration of the alert refractory period $\Delta T7$ is set such that it is larger than the sum of the durations of the alert window $\Delta T3$, the delay interval $\Delta T4$ and the maximal allowable duration $\Delta T5_{MAX}$ of the ETC signal. The maximal allowable duration $\Delta T5_{MAX}$ is a preset value.

Thus, $\Delta T7 > \Delta T3 + \Delta T4 + \Delta T5_{MAX}$. This ensures that no further threshold crossings will be sensed and detected after the first threshold crossing detection until the ETC signal has ended, irrespective of the time of occurrence of the first threshold crossing detection $T_2$ within the alert window duration $\Delta T3$ and of the specific duration $\Delta T5$ of the ETC signal delivered within the current beat cycle.

Typically, the duration $\Delta T3$ of the alert window is approximately 30 milliseconds, the duration of the delay interval $\Delta T4$ is approximately 60 milliseconds and the maximal allowable duration $\Delta T5_{MAX}$ of the ETC signal is approximately 20–30 milliseconds. However, other values of $\Delta T3$, $\Delta T4$ and $\Delta T5_{MAX}$ may be used.

A typical value of the duration of the alert refractory period $\Delta T7$ is therefore approximately 150–200 milliseconds. However, other values of the duration of the alert refractory period $\Delta T7$ may be used depending, inter alia, on the particular values of $\Delta T3$, $\Delta T4$ and $\Delta T5_{MAX}$ used. The duration of the alert refractory period $\Delta T7$ is a preset value and does not change from one beat cycle to another. However, The duration of the alert refractory period $\Delta T7$ may be changed if necessary by appropriately reprogramming the software embedded within the device 1 telemetrically or non-telemetrically (depending on the specific hardware implementation of the device 1).

For the sake of simplicity of presentation, the method of the present invention will be disclosed as using a single positive threshold level. A certain positive threshold voltage level is set for the pacemaker/ETC device. A crossing of this threshold level by the IEGM signal occurring within the time interval between $T_R$ and $T_3$ will be detected as an event. For example, the detection threshold may be set as +3.0 millivolts but other suitable threshold levels may also be used for detection, depending, inter alia, on the placement and quality of contact of the sensing electrode or electrodes with the cardiac site at which the sensing is performed. A refractory period of approximately 150–200 milliseconds starting at the time of detection of threshold crossing, may be used to prevent multiple threshold crossing detections, but other suitable values of the sense refractory period may also be used. In accordance with one preferred embodiment of the present invention, the use of the refractory period may be implemented as disclosed in detail in the above referenced co-pending U.S. patent application to Mika et al., Ser. No. 09/276,460, Titled "APPARATUS AND METHOD FOR TIMING THE DELIVERY OF NON-EXCITATORY ETC SIGNALS TO A HEART".

In accordance with another preferred embodiment of the present invention, the ETC device or pacemaker/ETC device of the present invention may continuously perform morphological analysis on the IEGM signal locally sensed in or about the left ventricle (or at a cardiac site in the vicinity of the cardiac site at which the ETC signal is to be delivered) for the entire duration of the alert window period, and the decision as to which of the depolarization events (provided that there was more than one such depolarization event within the alert window duration) is to be used as the ETC signal triggering event may be made based on the results of the morphological analysis which determine the depolarization event which gives the best match according with predetermined morphological criteria. After determining the event which is to be used as the ETC signal trigger, the timing of the delivery of the ETC signal is determined as disclosed in detail by Mika et al. In the co-pending U.S. patent application, Ser. No. 09/276,460 cited hereinabove.

It will be appreciated that any suitable method of morphological analysis known in the art including but not limited to the methods disclosed by Xue et al., Langberg et al., Ham and Han, and Flammang, may be used for morphological analysis in the method of the present invention, provided that the processor or controller used in the ETC device or pacemaker/ETC device has sufficient processing power.

It is noted that, many other suitable methods of event detection, including but not limited to the methods of using IEGM single threshold crossing, IEGM multiple threshold crossings, IEGM derivative (for signal slope determination), signal morphology detection methods or combinations thereof may be used in the ETC signal timing method of the present invention.

The conduction characteristics of the myocardium of a patient may vary considerably. Among the factors influencing the conduction velocity of the myocardium are electrophysiological changes induced in the myocardium due to patient exercise, increased metabolic activity or stress. These changes may be mediated, inter alia, by noradrenaline and other hormones which are released into the circulation and affect the myocardial conduction velocity or by sympathetic (or parasympathetic in some cases) neural control of cardiac tissue. Such mechanisms may lead to changes in the heart rate through their effects on the natural SA node pacemaker. Thus, under conditions of patient exercise, increased metabolic activity or stress, the heart rate increases and the conduction velocity of the myocardial depolarization wave increases. This increase in conduction velocity causes the electrogram signal sensed in the LV by the lead 6 (FIG. 1) to be shifted in time such that the time interval $T_2 - T_0$ decreases and may be smaller than $T_1$ which results in the locally sensed event 12 falling outside of the alert window and within the inhibition window ΔTI, which will lead to active inhibition of the delivery of the ETC signal. Slowing of the heart rate may cause the IEGM signal sensed in the LV by the lead 6 (FIG. 1) to be shifted in time such that the time $T_2$ of occurrence of the locally sensed event 12 occurs later within the alert window ΔT3 of FIG. 2, or occurs at a time point later than the time point $T_3$, which is outside of the alert window ΔT3 in which case no triggering will occur.

Additionally, the conduction velocity of a paced event in the myocardium is slower than the conduction velocity of the depolarization wave evoked by a naturally evoked sinus rhythm.

Another factor influencing the myocardial conduction velocity is the delivery of ETC signals to the myocardium. During the application of ETC signals to the myocardium the conduction velocity of myocardial depolarization may be modified. The conduction velocity may be increased or decreased depending, inter alia, on the type of ETC signal which is delivered to the myocardium.

Thus, the conduction velocity and consequently the time interval between the RV sensed event and the LV sensed event are heart rate dependent and may depend on other cardiac conditions.

In accordance with one embodiment of the present invention, the method of timing of the delivery of the ETC signal uses a fixed alert window delay period (ΔT2) and a fixed alert window duration (ΔT3) which is wide enough to enable acceptably accurate detection under a variety of conditions involving different myocardial conduction velocity values. A single set of alert window parameters is determined which includes the detection threshold value used for triggering within the alert window, the alert window starting time point $T_1$ and the alert window end time point $T_3$. This alert window parameter set is determined such as to enable an acceptable level of detection of events for all or most of the conditions involving different myocardial conduction velocity values. The pacemaker/ETC device 1 may then be programmed with this determined single set of alert window parameters as is disclosed in detail hereinafter. In this preferred embodiment of the present invention, once the alert window parameters are determined, the implanted pacemaker/ETC device 1 is programmed with these parameters and uses the same set of alert window parameters for the timing of the delivery of the ETC signals as disclosed hereinabove. The above cited co-pending U.S. patent application to Mika et al., Ser. No. 09/276,460, titled "APPARATUS AND METHOD FOR TIMING THE DELIVERY OF NON-EXCITATORY ETC SIGNALS TO A HEART", discloses a method and apparatus for timing the delivery of ETC signals to a heart using an alert window having preset fixed parameters.

However, it may be advantageous to use a plurality of different sets of alert window parameters. The use of a plurality of different alert window parameters is desirable since excessive widening of the alert window duration which may be required for suitable event detection under a variety of different patient cardiac conditions when a single alert window parameter set is used, may result in an increased probability of spurious detection of noise and/or ectopic events. In contrast, when a plurality of alert window parameter sets are used, the delay and duration of each specific alert window may be better adapted to a particular patient condition, such as but not limited to a particular heart rate, by modifying the alert window parameters sufficiently to position the alert window at the time period most proper for event detection to acceptably reduce the probability of detection of spurious noise and/or ectopic events.

Each set of alert window parameters includes data which may be used to calculate in real time the values of $T_1$ and $T_3$ which are optimized for a specific condition or for a specific range of conditions. The data of each set are determined so as to optimize detection of LV locally sensed events under the specific condition without unduly increasing spurious triggering. This method may be of particular advantage in patients in which the myocardial conduction velocity substantially varies between the different conditions disclosed hereinabove and in which the use of a single set of alert window parameters may lead to significant inaccuracies in the detection of the locally sensed event or in the timing of the ETC signal delivery during at least one of the various different conditions leading to changes of myocardial conduction velocity disclosed hereinabove. Such inaccuracies may occur due to a shift of the time of occurrence of the LV locally sensed event which may increase the probability of such a sensed event occurring out of the alert window time interval. This will cause a certain percentage of the LV locally sensed events to go undetected, so that not every LV locally sensed event will trigger the delivery of an ETC signal. While this may not by itself endanger the patient, it may lead to a reduction in the desired effect of the ETC signal on cardiac contractility. However, the use of a single common set of window parameters under varying conditions may result in increased rate of incorrect triggering of ETC signal delivery by spurious noise or by PVCs. This may lead to delivery of ETC signals outside of the inexcitable myocardial period which may be arrhythmogenic.

Therefore, in accordance with another preferred embodiment of the present invention, the implanted device 1 is programmed with a plurality of predetermined alert window parameter sets. Each of the predetermined parameter sets includes data for computing the values of $T_1$ and $T_3$ of the alert window in real time and may also include a detection threshold value. If a detection method using morphological IEGM parameters is used the alert window parameter sets may also include morphological parameter data useful for detecting a depolarization event. Each set of alert window parameters is optimized for use under specific conditions. For example, different alert window parameter sets may be used for different ranges of heart rates as is disclosed in detail hereinafter. Other different sets of alert window parameters may be used for paced events, sensed events, and for events occurring in periods during which ETC signals are delivered to the myocardium.

Systems and methods for determining alert window parameters

The present invention discloses, inter alia, systems and methods for determination of the alert window parameters.

Figure 3A:
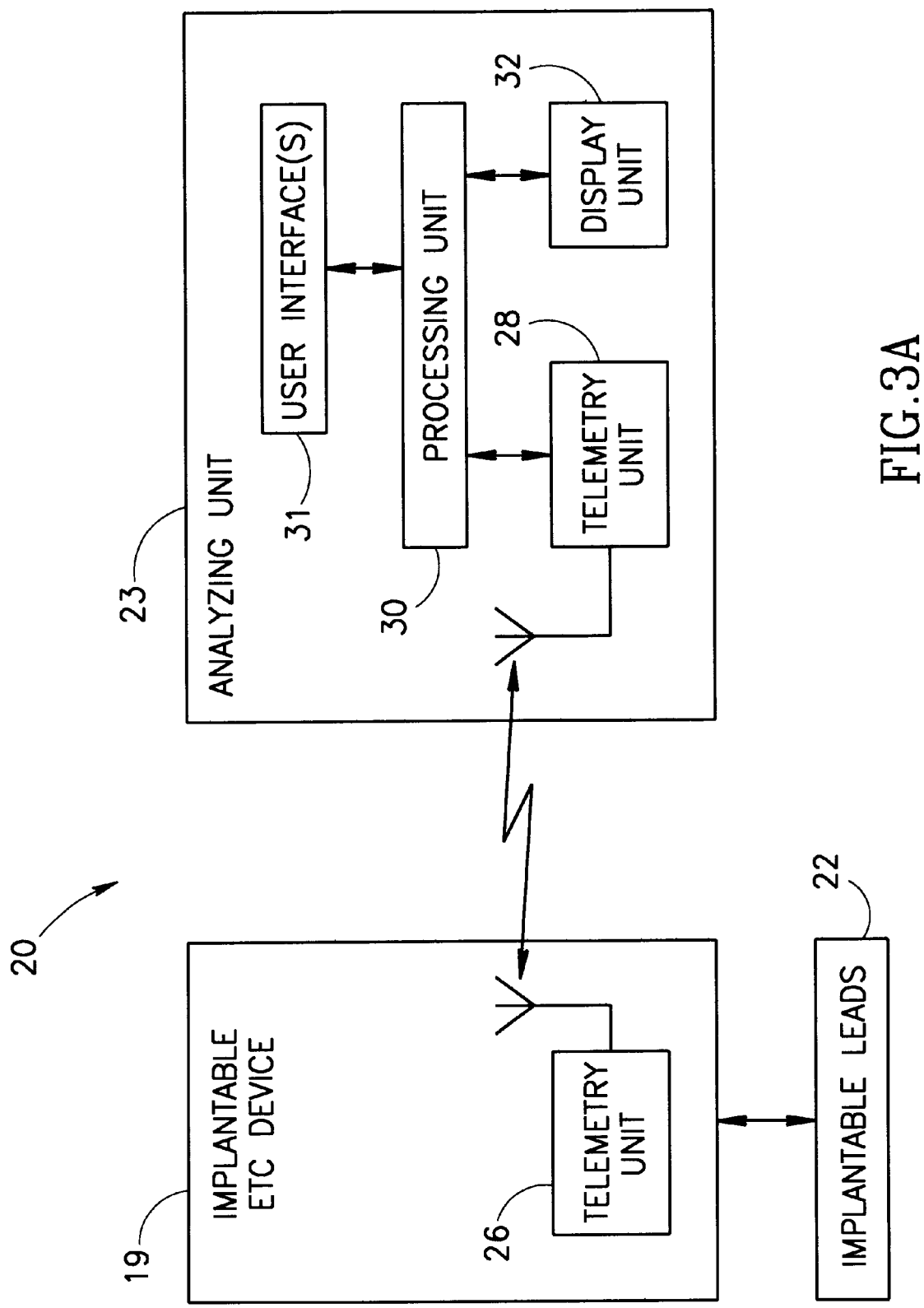
FIG. 3A is a schematic diagram illustrating a system for determining and programming alert window parameters for an implanted ETC device or pacemaker/ETC device, in accordance with a preferred embodiment of the present invention.

Reference is now made to FIG. 3A which is a schematic diagram illustrating a system for determining and programming alert window parameters for an implanted ETC device or pacemaker/ETC device, in accordance with a preferred embodiment of the present invention. The system 20 includes an implanted ETC device 19 and an analyzing unit 23. The implanted ETC device 19 further includes electronic circuitry (not shown in FIG. 3A for the sake of clarity of illustration) for event sensing and for delivering ETC signals, the details of such circuitry are disclosed in detail hereinafter. The implanted ETC device 19 may or may not include pacing circuitry (not shown in FIG. 3A for the sake of clarity of illustration) for pacing the heart as is disclosed in detail hereinafter. The implanted ETC device 19 is suitably connected to one or more implantable leads 22 and includes a telemetry unit 26 for wirelessly communicating with the analyzing unit 23. The analyzing unit 23 includes a telemetry unit 28 for wirelessly communicating with the telemetry unit 26 of the pacemaker/ETC device 19. The analyzing unit 23 further includes a processing unit 30 in communication with the telemetry unit 28 for receiving data from the telemetry unit 28 and for storing and processing the received data. The analyzing unit 23 further includes a display unit 32 suitably connected to the processing unit 30 for displaying graphic symbolic and numerical data processed by the processing unit 30. The processing unit 30 may be a computer, a personal computer, a workstation, a mainframe or any other type of computing device capable of storing and processing data. The display unit 32 may be a cathode ray tube (CRT) display, a video monitor, an LCD display or any other suitable type of display or monitor. The analyzing unit 23 further includes one or more user interfaces 31 for enabling a user such as a cardiologist or another operator to control the operation of the analyzing unit 23. The user interface 31 may be a keyboard, a pointing device or any other suitable user interface device or a combination of user interface devices which are known in the art.

Figure 3B:
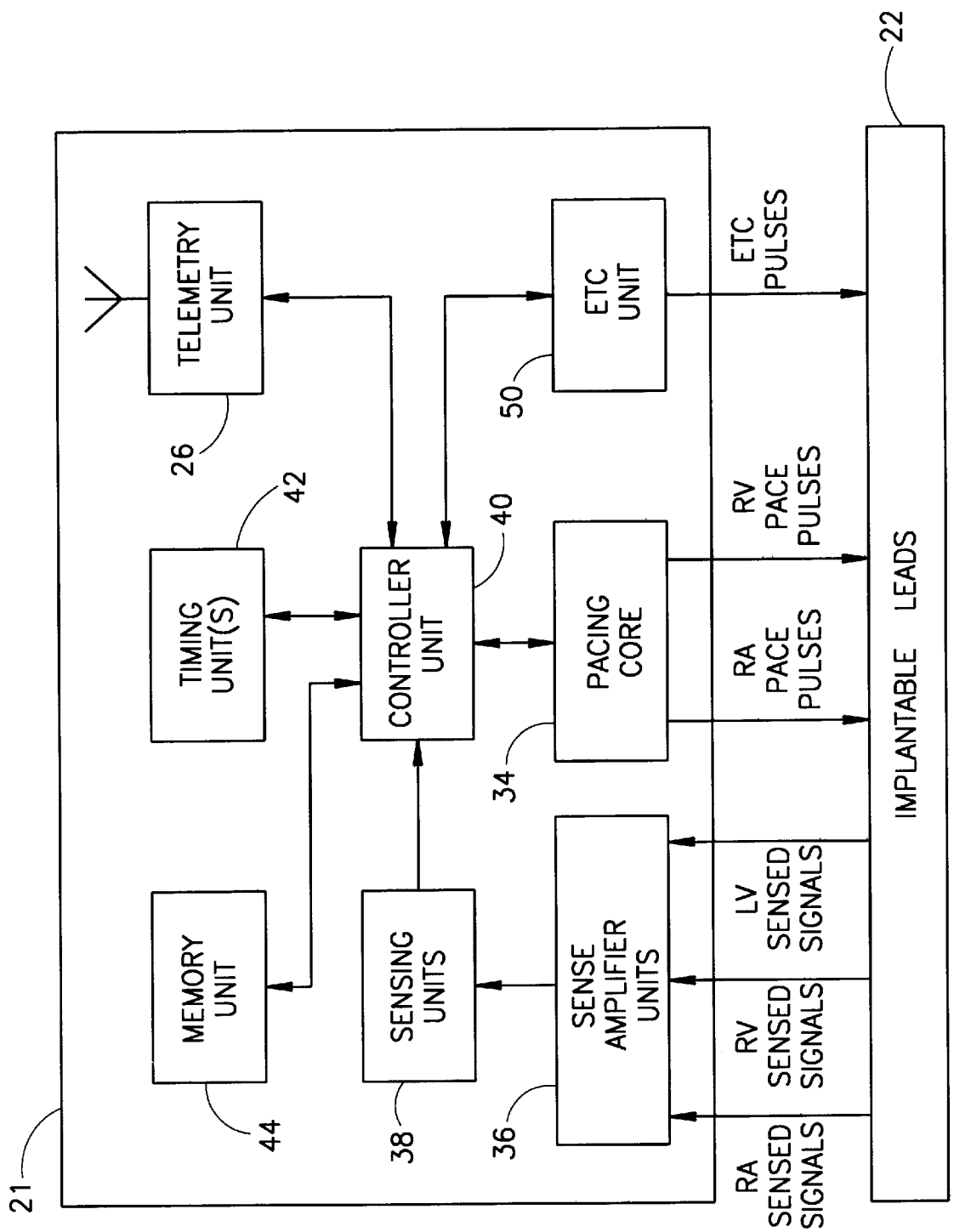
FIG. 3B is schematic functional block diagram illustrating the details of an implantable device for pacing the heart, for delivering ETC signals to the heart and for data acquisition and processing usable as the implantable device of the system of FIG. 3A, in accordance with a preferred embodiment of the present invention.

Reference is now made to FIG. 3B which is schematic functional block diagram illustrating the details of an implantable device for pacing the heart, for delivering ETC signals to the heart and for data acquisition and processing usable as the implantable device of the system of FIG. 3A, in accordance with a preferred embodiment of the present invention. The implantable pacemaker/ETC device 21 is a preferred version of the implantable device 19 of FIG. 3A suitable for use within the system 20 of FIG. 3A The pacemaker/ETC device 21 includes a pacing core 34 for providing pacing pulses to the RA and RV pacing electrodes (not shown) of the implantable leads 22. The pacemaker/ETC device 21 further includes sense amplifier units 36 for amplifying the RA, RV and LV signals locally sensed by the sensing electrodes (not shown) of the implantable leads 22. For example, when the pacemaker/ETC device 21 represents the pacemaker/ETC device 1 of FIG. 1, one of the sense amplifier units 36 receives the signal locally sensed in the RA 8 from lead 2 of FIG. 1, another of the sense amplifier units 36 receives the signal locally sensed in the RV 9 from lead 4 of FIG. 1 and a third one of the sense amplifier units 36 receives the signal locally sensed in the LV 10 from the lead 6 of FIG. 1.

The pacemaker/ETC device 21 further includes sensing units 38 suitably connected to a controller unit 40. The sensing units 38 receive the amplified locally sensed signals from the amplifier units 36 and provide trigger signals to the controller unit 40 for activating the pacing core as is known in the art. The pacemaker/ETC device 21 further includes timing units 42, connected to the controller unit 40 for providing the controller unit 40 with clock signals, and a memory unit 44 suitably connected to the controller unit 40. The controller 40 can store data in the memory unit 44 and can access the data stored in the memory unit 44 for processing the accessed data and/or for sending data to a telemetry unit 26 for telemetrically communicating the data to a receiving station (not shown) placed outside of the patient. The memory unit 44 may include random access memory (RAM) units (not shown), read only memory (ROM) units (not shown), other suitable type of memory units known in the art, or any suitable combination of memory unit types.

It is noted that the pacemaker/ETC device 21 when connected to implantable leads having the configuration of leads 2, 4, and 6 of FIG. 1, may function, inter alia, as a pacemaker in a DDD mode, which includes, inter alia, the ability to detect PVCs by using PVC detection methods known in the art. For example, PVC detection may be performed by the circuitry of the pacemaker/ETC device 21 using dual chamber event sequence analysis methods as is known in the art. However, other methods known in the art for PVC detection may also be used.

The telemetry unit 26 is used for wirelessly transmitting data stored in memory unit 44 under the control of the controller unit 40. The pacemaker/ETC device 21 further includes an excitable tissue controller (ETC) unit 50. The ETC unit 50 is suitably connected to the controller unit 40 and to one or more ETC electrodes (not shown) within the leads 22. For example, when the pacemaker/ETC device 21 represents the pacemaker/ETC device 1 of FIG. 1, the ETC unit 50 is connected to the ETC signal delivering electrode 6A of the lead 6 of FIG. 1. However in other preferred embodiments of the present invention, the ETC unit 50 may be connected to one or more ETC electrodes or ETC electrode pairs (not shown) which are used for delivering ETC signals. The controller unit 40 controls the delivery of ETC signals to the myocardium by timing the delivery of suitable control signals to the ETC unit 50.

Figure 4:
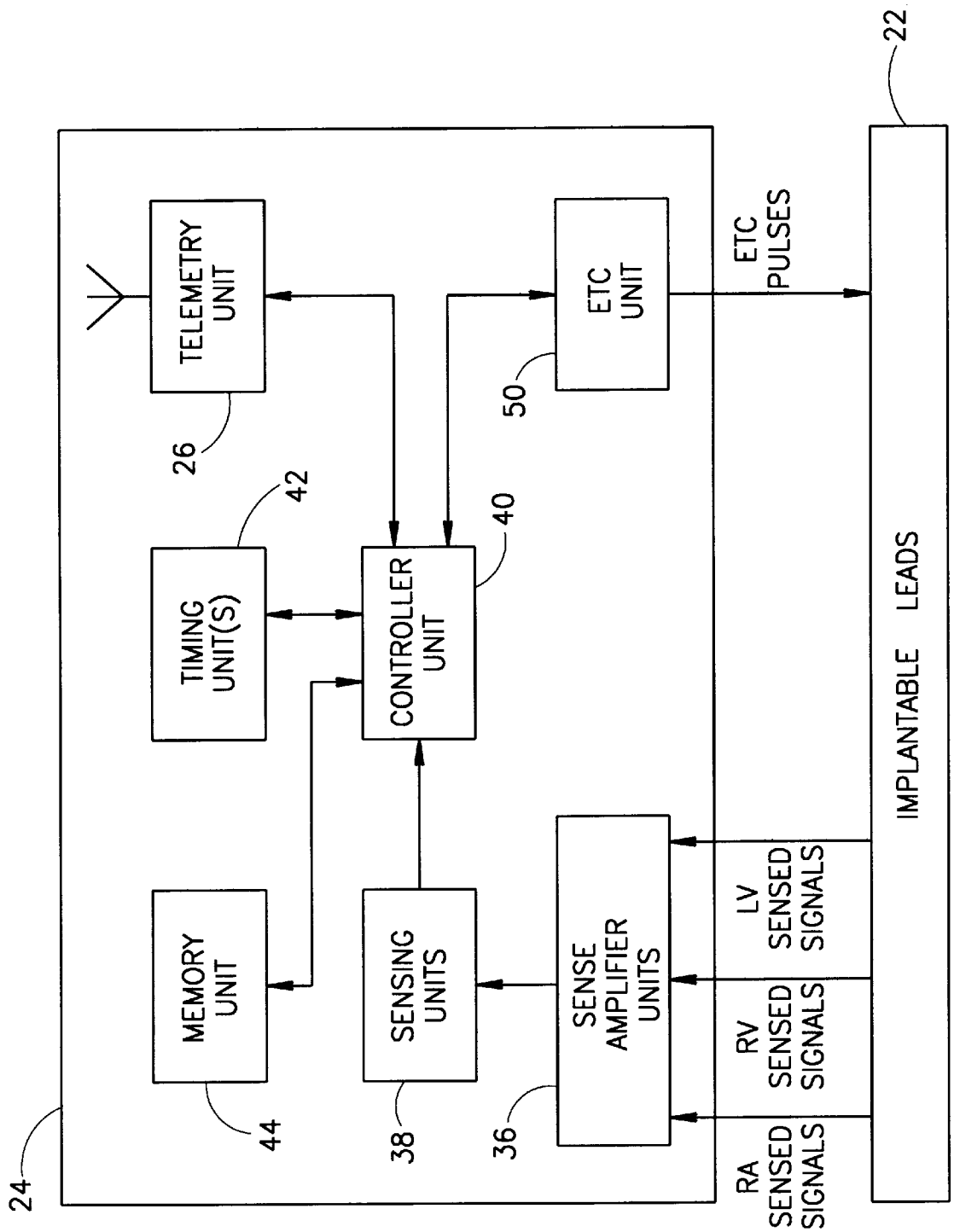
FIG. 4 is schematic functional block diagram illustrating the details of another implantable device for delivering ETC signals to the heart and for data acquisition and processing which is usable as the implantable device of the system of FIG. 3A, in accordance with another preferred embodiment of the present invention.

Reference is now made to FIG. 4 which is schematic functional block diagram illustrating the details of another implantable device for delivering ETC signals to the heart and for data acquisition and processing which is usable as the implantable device of the system of FIG. 3A, in accordance with another preferred embodiment of the present invention. The device 24 is similar to the device 21 of FIG. 3A except that it does not include the pacing core 34 of the device 21 of FIG. 3A and is not capable of pacing.

The device 24 may be used in patients where ETC signals need to be delivered to the heart for modulating cardiac contractility but pacing of the heart is not required, such as but not limited to congestive heart failure (CHF) patients. CHF patients may have an unimpaired cardiac conduction system and may exhibit no chronotropic incompetence. In the cases where the device 24 is used for delivering ETC signals to the heart, the electrodes (not shown) in the implantable leads 22 are used for sensing and for delivering ETC signals and are not used for pacing the heart.

In operation, the data stored in the memory unit 44 of the devices 21 and 24 of FIGS. 3A and 4, respectively, is telemetrically transmitted by the telemetry unit 48 to the analyzing unit 23 (FIG. 3A) which is disposed outside the patient for processing, storage and display. The system 20 of FIG. 3A may graphically display the data on the display unit 32. The displayed data is used by the user or physician to determine the alert window parameters as is disclosed in detail hereinafter. Alternatively, the alert window parameters may be automatically determined and displayed for approval by the user or the physician.

In accordance with another preferred embodiment of the present invention, the alert window parameters may be determined by non-telemetrically communicating the locally sensed IEGM signals sensed in a patients heart to a processing and analyzing system disposed outside the patient.

Figure 5:
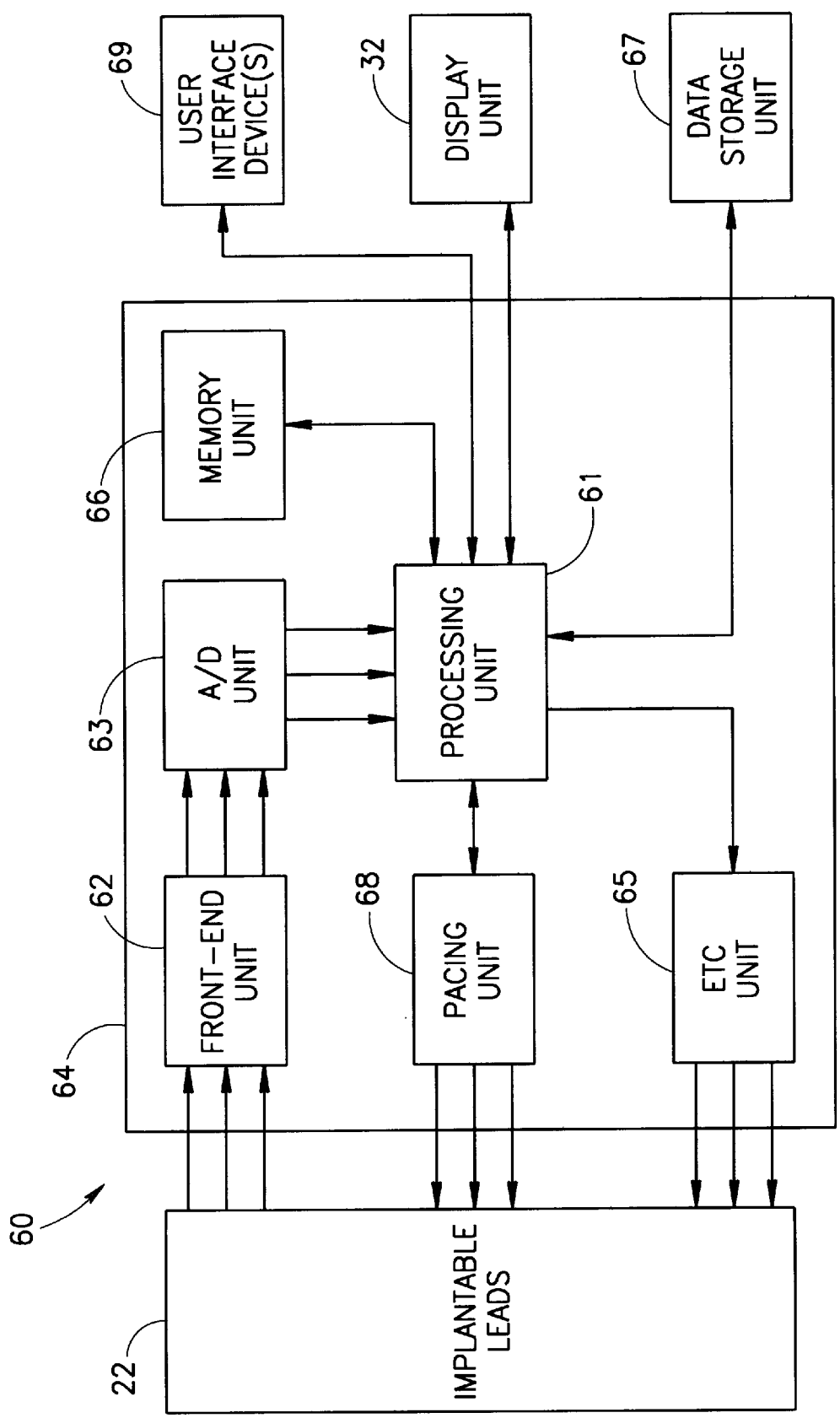
FIG. 5 is a schematic diagram illustrating a system for pacing the heart, for delivering non-excitatory ETC signals and for non-telemetrically determining and programming alert window parameters for an ETC device or pacemaker/ETC device, in accordance with another preferred embodiment of the present invention.

Reference is now made to FIG. 5 which is a schematic diagram illustrating a system 60 for pacing the heart, for delivering non-excitatory ETC signals and for non-telemetrically determining and programming alert window parameters for an ETC device or pacemaker/ETC device, in accordance with another preferred embodiment of the present invention. The system 60 includes a plurality of implantable leads 22 implanted within a patient (the patient is not shown) and an analyzing unit 64. The plurality of implantable leads 22 may include, for example, the leads 2, 4 and 6 of FIG. 1. However, the plurality of leads 22 may include any other suitable combinations of leads including a plurality of sensing, pacing and ETC electrodes positioned in two or more chambers of the heart as disclosed for the devices 1, 19, 21 and 24 hereinabove.

The plurality of leads 22 are implanted in the patient's heart and are then suitably connected to the analyzing unit 64 for data acquisition to collect data for determining the alert window parameters.

The analyzing unit 64 includes a processing unit 61, a front-end unit 62, an analog to digital converting unit (A/D) 63, a pacing unit 68 and an ETC unit 65. The front end unit 62 is suitably connected to one or more of the sensing electrodes of the leads 22 and to the processing unit 61 for pre-conditioning one or more IEGM signals sensed by these one or more sensing electrode. The front-end unit 62 may include suitable circuitry such as one or more amplifier circuits (not shown) for amplifying the IEGM signals sensed by the one or more sensing electrodes. The front-end unit 62 may also include filter circuits (not shown) for filtering the amplified signals prior to digitizing them by the A/D unit 63. The front-end unit 62 is suitably connected to the A/D unit 63 and provides amplified or amplified and filtered IEGM signals thereto for digitizing.

The A/D unit 63 may include one or more separate A/D converters (not shown) each A/D converter being dedicated to a single sensing electrode of the one or more sensing electrodes. Alternatively, the A/D unit 63 may include a single A/D converter (not shown) suitably connected to a plurality of sensing electrodes of the leads 22 through a multiplexer unit (not shown). The digitized IEGM signals are provided to the processing unit 61 by the A/D unit 63 for further processing. The processing unit 61 digitally performs the detection of events based on the digitized IEGM data provided by the A/D unit 63. The analyzing unit 64 further includes a memory unit 66 suitably connected to the processing unit 61 for storing data.

The pacing unit 68 is suitably connected to the processing unit 61 and to one or more pacing electrodes of the leads 22. The pacing unit 68 receives control signals from the processing unit 61 for controlling the delivery of pacing pulses to one or more locations in the heart (not shown). The pacing unit 68 includes all the necessary circuitry for delivering pacing pulses to one or more pacing electrodes. Such circuitry is well known in the art and is not shown in detail hereinafter.

It is noted that the analyzing unit 64 when connected to the implantable leads 22 is capable of performing all the functions of an implanted pacemaker. For example, when the leads 22 have the configuration of leads 2, 4, and 6 of FIG. 1, the analyzing unit 64 is capable of performing, inter alia, all the functions of an implanted pacemaker in a DDD mode. These functions include, inter alia, the ability of detection of PVCs as is well known in the art.

The ETC unit 65 is suitably connected to the processing unit 61 and to one or more ETC signal delivery electrodes of the implantable leads 22. The ETC unit 65 receives control signals from the processing unit 61 for controlling the delivery of ETC signals to the heart through the one or more ETC delivery electrodes of the implantable leads 22.

The ETC unit 65 may be any suitable unit for delivering ETC signals having various waveforms, duration values and intensities as disclosed in detail by Ben Haim et al. in the above referenced International Publications No. WO 97/25098, WO 98/10828, WO 98/10829, WO 98/10830, WO 98/10831 and WO 98/10832. The characteristics of the delivered ETC signals are not the subject of the present invention and will not be further discussed hereinafter.

The system 60 further includes a display unit 32 suitably connected to the processing unit 61 for displaying graphic symbolic and numerical data processed by the processing unit 61 as disclosed hereinabove for the analyzing system 20 of FIG. 3A. The system 60 may further include a data storage unit 67 for storing data. The data storage unit 67 may be any suitable data storage device for storing data on a storage medium such as a magnetic storage medium, an opto-magnetic storage medium, an optical storage medium, a holographic storage medium or any other type of fixed or removable storage medium. Some non-limiting examples of the storage device are, a magnetic hard disk drive, a magnetic floppy disk drive, an opto-magnetic disk drive, an optical disc drive. The data stored on the data storage device may include, inter alia, patient clinical data, patient demographic data, various IEGM and histogram data collected in the process of determining the alert window parameters and various determined alert window parameter sets. The data storage device may be used for storing data for a plurality of different patients.

The system 60 further includes one or more one user interface devices 69 suitably connected to the processing unit 61 through a suitable communication interface (not shown) for enabling the user of the system 60 to input data and commands for controlling the operation of the analyzing unit 64. The user interface device(s) 69 may be a keyboard, a pointing device such as a mouse, a light pen in combination with a suitable touch sensitive screen or tablet, or any other suitable device for inputting data or commands to the analyzing unit 64, or any suitable combination thereof.

In operation, after the leads 22 are implanted in the heart of the patients and are connected to the analyzing unit 64, the analyzing unit 64 is operated to collect data for determining the parameter sets for the alert window under various conditions as is disclosed in detail hereinafter. It is noted that the analyzing unit 64 is capable of performing all the activities of an implanted pacemaker/ETC device such as the pacemaker/ETC device 21 of FIG. 3A except for the telemetry functions. The analyzing unit 64 may perform cardiac pacing at one or more cardiac locations and may controllably deliver ETC signals to one or more cardiac locations. The performance of the functions of a pacemaker/ETC device by the analyzing unit 64 may be achieved by using different methods and/or different hardware implementation than the methods and hardware of an implantable pacemaker/ETC device. For example, while in the pacemaker/ETC device 21 the event detection is performed by sensing units 38 which are analog circuits, the event detection in the analyzing unit 64 is performed by digitally processing the digitized IEGM data provided by the A/D unit 63. Additionally, the pacing unit 68 and the ETC unit 65 may have hardware and software implementations different than those of the pacing core 34 and the ETC unit 50, respectively, of the pacemaker/ETC device 21 because of the physical size and current consumption limitations imposed on the design of the pacing core 34 and the ETC unit 50 of the pacemaker/ETC device 21. These limitation are not relevant in the non-implanted analyzing unit 64. However, functionally, the sensing, pacing and ETC delivery of the analyzing unit 64 are similar to and may be regarded as simulating the same functions of an implanted of the pacemaker/ETC device, such as, for example, the functions of the pacemaker/ETC device 21 of FIG. 3A. Therefore, after the different alert window parameter sets are determined using the analyzing unit 64, these alert window parameter sets may be used to program an implanted pacemaker/ETC device and are used to operate the programmed implanted pacer/ETC device after it has been suitably connected to the implantable leads 22 and implanted in the patient.

Figure 6:
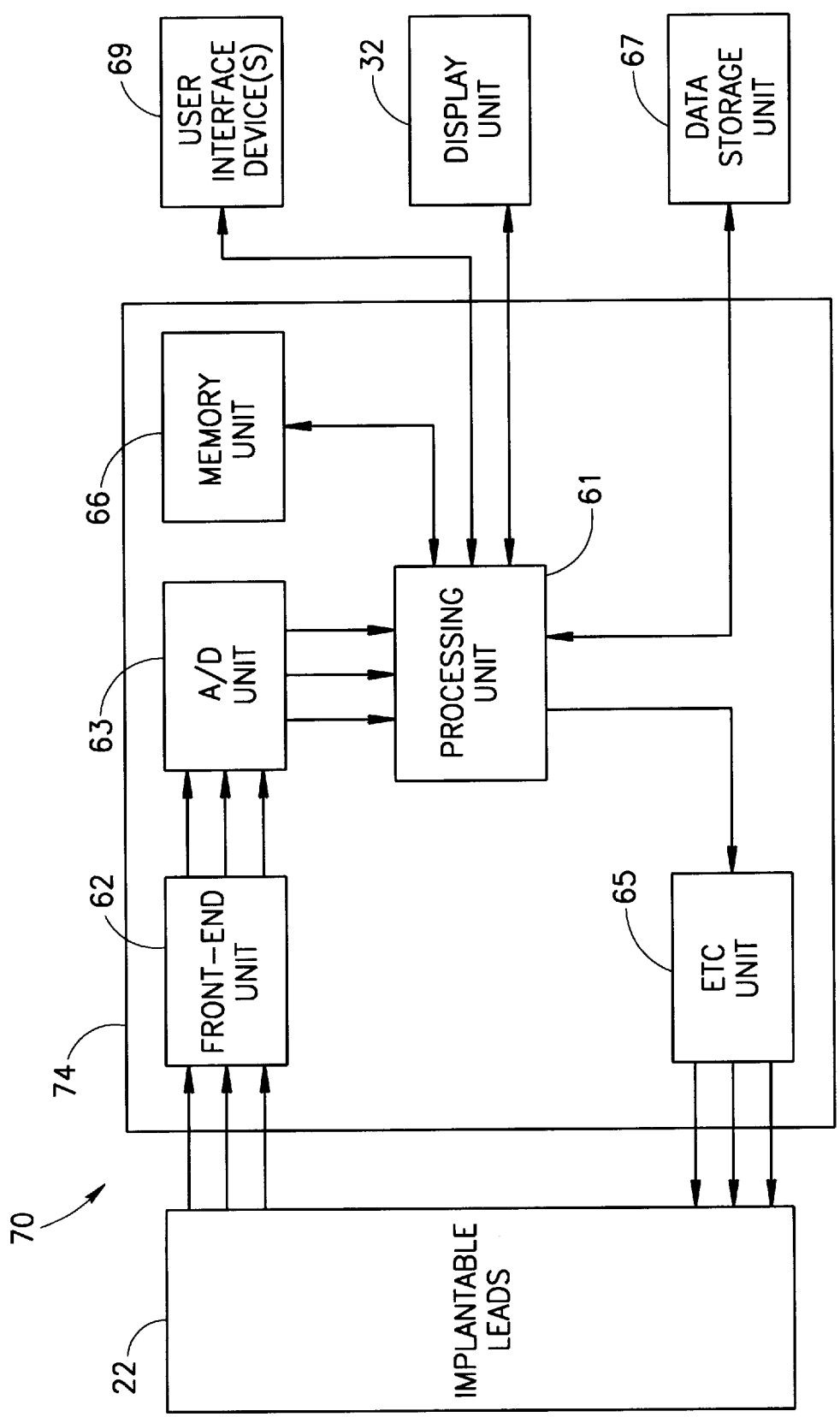
FIG. 6 is a schematic functional block diagram illustrating a system 70 for delivering non-excitatory ETC signals and for non-telemetrically determining alert window parameters for use in an ETC device, in accordance with another preferred embodiment of the present invention.

Reference is now made to FIG. 6 which is a schematic functional block diagram illustrating a system 70 for delivering non-excitatory ETC signals and for non-telemetrically determining alert window parameters for use in an ETC device, in accordance with another preferred embodiment of the present invention.

The system 70 includes an external non-implanted analyzing unit 74 suitably connected to a plurality of implantable leads 22. The analyzing unit 74 of FIG. 6 is similar to the analyzing unit 64 of FIG. 5, except that it does not include the pacing unit 68. The analyzing unit 74 operates similarly to the analyzing unit 64, except that it does not have the pacing capacity of the analyzing unit 64 and is therefore not capable of pacing of the heart.

It is noted that, while the devices 1, 19, 21 and 24 of FIGS. 1,3, 3A and 4 respectively, and the systems 60 and 70 of FIGS. 5 and 5A, respectively, may use the single threshold crossing detection method disclosed in detail hereinabove, all of these devices and systems may use other detection methods. The detection methods for detecting depolarization events in the IEGM signals sensed by one or more of the electrodes or electrode pairs included in one or more of the implantable leads such as the leads 2,4, and 6 of the device 1 and the plurality of implantable leads 22 of the devices 19, 21 and 24 and the systems 60 and 70, may include any suitable detection methods known in the art for detection of locally sensed cardiac depolarization events based on signal morphology and/or methods based on multiple threshold crossings and/or signal slope or any combinations thereof as disclosed hereinabove.

Typically, the data acquisition method of the present invention includes automatically varying the detection threshold levels and cumulatively recording data of threshold crossing events at predefined time bins starting at the time of detection of an RV event ($T_0$ of FIG. 2).

After implantation of the pacemaker/ETC device 21 the pacing parameters are set (including, inter alia, the pacing voltage, the pacing pulse width, and other relevant pacing parameters), data acquisition and processing will take place as explained hereinbelow. If the device 24 or the system 70 are used for data acquisition no pacing parameters need be set since the device 24 and the system 70 have no pacing capability and no pacing is performed thereby.

It is noted that in accordance with a preferred embodiment of the present invention data acquisition may also be performed by implanting the implantable electrodes 22 in a patient and then operatively connecting the implantable leads 22 to the external analyzing unit 64 of the system 60 of FIG. 5 or to the external analyzing unit 74 of the system 70 of FIG. 6. The pacing parameters of The external analyzing unit 64 of the system 60 are set (including, inter alia, the pacing voltage, the pacing pulse width, and other relevant pacing parameters), and data collection may be then performed while the patient is recovering from the electrode implantation procedure for as long as the electrodes 22 implanted in the patient are connected to the analyzing unit 64. Similarly data may be collected by operatively connecting the implanted electrodes 22 to the analyzing unit 74 wherein no pacing is performed.

While the data collected from a patient with an implanted device may be different from data collected from a hospitalized patient using the systems 60 and 70, the cardiac conditions of the patient may be altered by instructing the patient to perform certain types of physical activity while he is in bed.

For the sake of simplicity, the following description of the data acquisition method relates to freely moving patients having an implanted pacemaker/ETC device such as the device 21 of FIG. 3A. However, it will be appreciated that the methods are also adaptable to patients in which the device 24 or one of the systems 60 and 70 is used, by suitably adapting and modifying the methods to the different patient conditions or to the absence of cardiac pacing when the device 24 or the system 70 are used.

Data acquisition

After implantation of the pacemaker/ETC device 21 in the patient, the patient is sent home for a time period which is estimated as sufficient for collecting enough data such as a few days or weeks. The patient is instructed to carry out daily routine behavior. The pacemaker/ETC device 21 records data as is disclosed in detail hereinafter. The data is then offloaded from the pacemaker/ETC device 21 telemetrically as disclosed hereinabove. The off-loaded data is then stored for further processing by the analyzing unit 23 of FIG. 3A.

Record data structure

Figure 7:
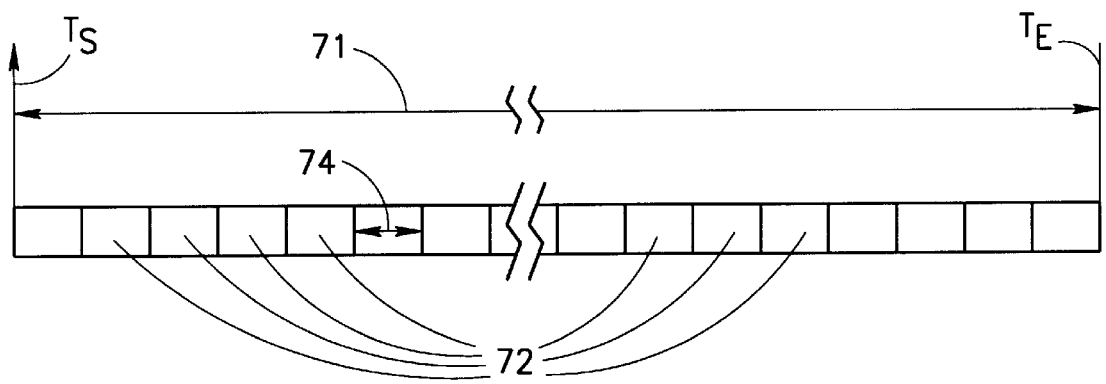
FIG. 7 is a schematic diagram illustrating the structure of a typical data collection time interval useful in the acquisition of data histograms, in accordance with a preferred embodiment of the present invention.

Reference is now made to FIG. 7 which is a schematic diagram illustrating the structure of a typical data collection time interval useful in the acquisition of data histograms, in accordance with a preferred embodiment of the present invention.

For each cardiac beat, Detected LV event data is collected within the duration of a data collection time interval 71. The data collection time interval 71 begins at a starting time point $T_S$ and ends at an ending time point $T_E$.

In ETC devices having pacing capability such as the pacemaker/ETC device 21 of FIG. 3B, the analyzing unit 64 of the system 60 of FIG. 5 and the like, the initiation of the data collection time interval 71 is triggered by the detection of an RV event or by the delivering of a pacing pulse to the RV. However, in embodiments of the present invention in which no sensing and no pacing are performed in the RV, the initiation of the data collection time interval 71 is triggered by the detection of an RA event or by the delivering of a pacing pulse to the RA.

In ETC devices having no pacing capability such as the pacemaker/ETC device 24 of FIG. 4, the analyzing unit 74 of the system 70 of FIG. 6 and the like, the initiation of the data collection time interval 71 is triggered by the detection of an RV event. However, in embodiments of the present invention in which no sensing is performed in the RV, the initiation of the data collection time interval 71 is triggered by the detection of an RA event.

The duration of the time interval 71 is preset by the user or cardiologist before the beginning of the data collection period and does not change during the data collection. The duration of the time interval 71 is typically 100–150 milliseconds, however, other duration values of the data collection time interval 71 may be used. The duration of the data collection time interval 71 is set such that it is large enough to include the LV sensed events representing the myocardial depolarization wave under extreme cardiac conditions which may be encountered in a patient including, inter alia, various ranges of heart rates with or without ETC signal application, with or without pacing in both non-treated and drug treated patients. The duration of the data collection time interval 71 is selected such that it does not extend into the next heart beat cycle. Practically, the duration of the data collection time interval 71 may also be limited by the data storage capacity available in the memory unit of the pacemaker/ETC devices or the ETC devices disclosed in detail hereinabove.

The data collection time interval 71 is divided into N contiguous time bins 72 of equal duration. The double headed arrow 74 represents the duration of each of the time bins 72 (which is equal to $T_E-T_S$). This set of time bins forms the basis for recording a plurality of histogram data sets. Each of the plurality of histogram data sets may be stored in the memory unit 44 of the pacemaker/ETC device 21 (FIG. 3B) or of the ETC device 24 (FIG. 4) or in the memory unit 66 of the analyzing unit 64 of the system 60 (FIG. 5) or of the analyzing unit 74 of the system 70 (FIG. 6). Each histogram data set of the plurality of histogram data sets represents a cumulative time distribution histogram and includes a set of integer variables each representing the cumulative number of locally sensed LV events which were detected within a particular time bin of the N time bins 72 in a plurality of beat cycles belonging to a particular histogram data set. Each of the histograms represents data collected from a plurality of beat cycles having in common a unique set of conditions including a specific LV detection sensitivity level, the beat being paced or sensed beats, and the beats having been collected during a time period in which ETC signal delivery substantially affects myocardial depolarization wave conduction velocity or during a time period in which no ETC signal delivery occurred or the ETC delivery which did occur did not substantially affect the myocardial depolarization wave conduction velocity, and having a cycle length belonging to a particular class of cycle lengths as is disclosed in detail hereinbelow. Each particular cycle length class includes heart beats having a duration falling within predetermined range of cycle length durations.

Figure 8A:
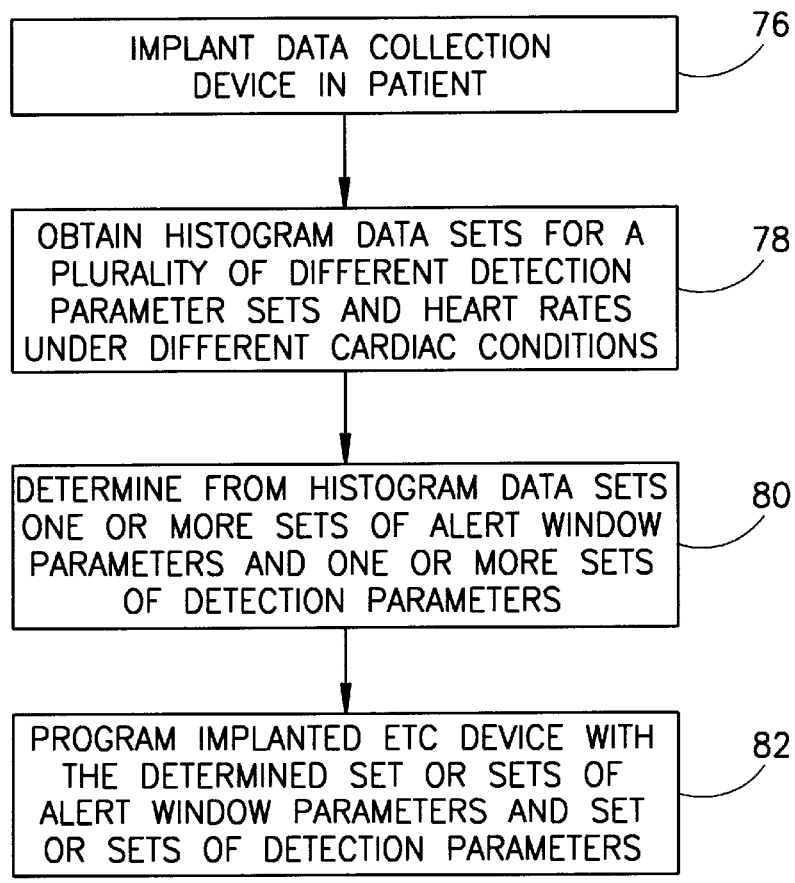
FIG. 8A is a schematic diagram illustrating the general steps of a method for collecting time histogram data sets under various cardiac conditions and for determining one or more sets of alert window parameters or one or more and one or more detection parameter sets from the histogram data, in accordance with a preferred embodiment of the present invention.

Reference is now made to FIG. 8A which is a schematic diagram illustrating the general steps of a method for collecting time histogram data sets under various cardiac conditions and for determining one or more sets of alert window parameters and one or more detection parameter sets from the histogram data, in accordance with a preferred embodiment of the present invention.

The method includes the implanting of a data collecting device in a patient (step 76). The term data collection device of step 76 is used herein as a broad term describing a device capable of sensing and detecting depolarization events in at least two cardiac sites and of processing and storing data. The data collection device is capable of delivering ETC non-excitatory signals to the heart. Preferably (but not necessarily), the device may also be capable of pacing the heart as is known in the art. For example, The data collection device may include the implantable electrodes 22 operatively connected to the pacemaker/ETC device 21 of FIG. 3A or to the device 24 of FIG. 4. Alternatively, the data collection device may include the implanted leads 22 operatively connected to the external analyzing unit 64 of the system 60 of FIG. 5 or to the external analyzing unit 74 of the system 70 of FIG. 6.

The method further includes obtaining the histogram data sets disclosed in detail hereinabove (step 78). The histogram data sets are obtained by using a plurality of different detection parameters or a plurality of different detection parameter sets depending, inter alia, on the type and complexity of the event detection method which is implemented by the data collection device. Different histogram data sets are obtained under different cardiac conditions such as, but not limited to, different heart rate ranges, artificially paced heart beats, and naturally occurring heart beats (sensed), artificially paced heart beats in the presence of on-going delivery of non-excitatory ETC signals and naturally occurring heart beats in the presence of the on-going delivery of non-excitatory ETC signals. These different conditions are disclosed in detail hereinafter.

The histogram data sets collected by the pacemaker/ETC device 21 may be stored in the memory unit 44 and telemetrically transmitted to the analyzing unit 23 (FIG. 3A) for processing. If the ETC device 24 of FIG. 4 is used for data collecting, the histogram data sets are stored in the memory unit 44 of the device 24. If the system 60 of FIG. 5 is used for data collection, the histogram data sets collected by the analyzing unit 64 are stored in the memory unit 66 for further processing. If the system 70 of FIG. 6 is used for data collection, the histogram data sets collected by the analyzing unit 74 are stored in the memory unit 66 for further processing.

The method further includes processing of the histogram data sets obtained in step 78 to determine one or more sets of alert window parameters, and one or more sets of detection parameters (step 80). Typically, each of the alert window parameter sets includes an alert window starting time value and an alert window ending time value. Each of the determined alert window parameter sets and detection parameter sets may be suitable for use under a particular combination of cardiac conditions such as a particular heart rate in a sensed or in a paced heart beat, and in the absence or presence of on-going delivery of non-excitatory ETC signals. Each particular set of alert window parameters may be associated with a particular set of detection parameters. However, in some cases a common single set of detection parameters may be associated with some or with all of the sets of alert window parameters.

In other cases, a single common set of window parameters may be used for some or for all of the cardiac conditions disclosed hereinabove.

The method also includes the step of programming an implanted ETC device or ETC/pacemaker device with the determined set or sets of alert window parameters and with the determined set or sets of detection parameters (step 82).

It is noted that, the step 78 and the step 80 may or may not be performed by the same device. For example, in accordance with a preferred embodiment of the present invention, step 78 may be performed by an implanted device such as but not limited to the device 21 of FIG. 3A (or the implanted device 24 of FIG. 4), the stored data may then be telemetrically transmitted to an external analyzing unit such as but not limited to the analyzing unit 23 of FIG. 3A, step 80 is then performed by the analyzing unit 23 and in step 82 the implanted device 21 of FIG. 3A (or the implanted device 24, of FIG. 4) is telemetrically programmed with the determined set or sets of alert window parameters and with the set or sets of detection parameters.

In accordance with another preferred embodiment of the present invention, step 78 may be performed by a device including implanted electrodes such as the implantable electrodes 22 which are operatively connected to an external device such as but not limited to the analyzing unit 64 of FIG. 5 (or the analyzing unit 74 of FIG. 6) and the data is stored in the memory unit 66 of the analyzing unit 64 (or of the analyzing unit 74). Step 80 is then performed by the analyzing unit 64 (or the analyzing unit 74). The implantable electrodes 22 are then disconnected from the analyzing unit 64 (or from the analyzing unit 74) and in step 82 an implantable ETC or ETC/pacemaker device such as but not limited to the device 21 of FIG. 3A (or the device 24 of FIG. 4) is connected to the implantable electrodes 22 and implanted in the patient. The programming (step 82) of the device 21 (or the device 24) with the alert window parameter set of the or sets and with the detection parameter set(s) may be performed prior to the implantation of the device 21 (or the device 24) within the patient or may be performed telemetrically after implantation of the device 21 (or the device 24).

Figure 8B:
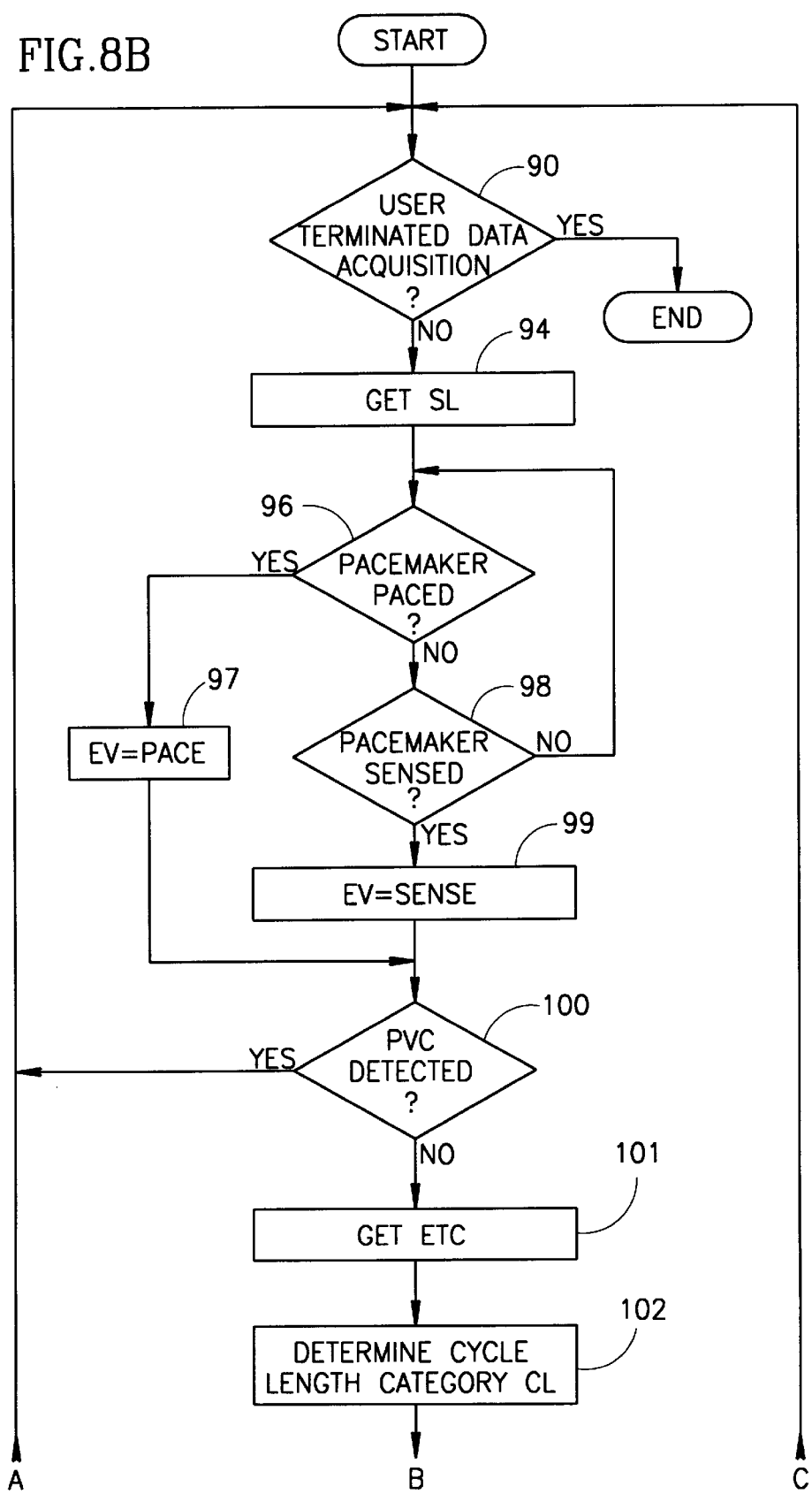
FIGS. 8B and 8C are schematic flow control diagrams illustrating the steps of a data collection method for collecting time histogram data sets in detail, in accordance with a preferred embodiment of the present invention.
Figure 8C:
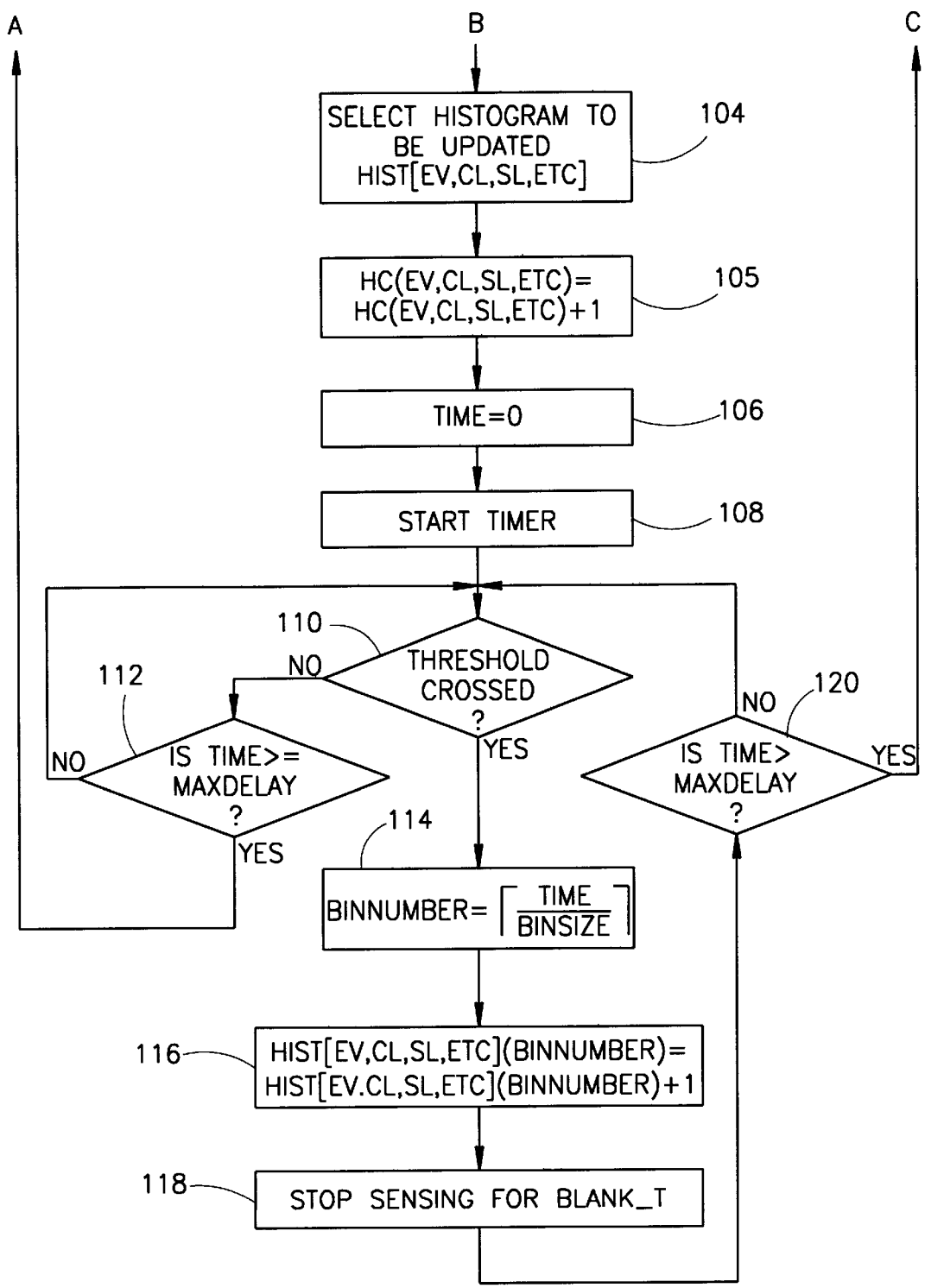

Reference is now made to FIGS. 8B and 8C which are schematic flow control diagrams illustrating the steps of a data collection method for collecting time histogram data sets in detail, in accordance with a preferred embodiment of the present invention.

The data collection program embedded within the pacemaker/ETC device 21 or the analyzing unit 64 starts by checking whether the user or operator has terminated the collection of data (step 90). The user (typically the cardiologist) may terminate data collection by a suitable command which is transmitted telemetrically to the pacemaker/ETC device 21 of the system 20, or input manually to the analyzing unit 64 of the system 60 through one of the user interface device(s) 69. Typically, the command may set a suitable flag or change the value of a variable which is checked by the program. However, other suitable methods for terminating data collection may be used. If the user did terminate data collection the data collection program ends (step 92). If the user did not terminate data collection, the program gets the current sensitivity level value SL (step 94). The sensitivity level variable SL may be an integer variable which can take any integer value selected from a group of integer numbers, each representing a particular sensitivity value available for use in the pacemaker/ETC device 21 or the analyzing 64. For example, if the event detection sensitivity is determined by the crossing of a single voltage threshold and the pacemaker/ETC device can have 8 different sensitivity levels, SL may be any integer in the range 1–8.

The data collection program checks whether the pacemaker paced (step 96). This is performed by checking the pacing data for the current beat cycle which is stored by the pacemaker/ETC device 21 or by the pacing program operating the processing unit 61 of the analyzing unit 64. If the pacemaker paced the data collection program sets the value of the logical parameter to EV=PACE to indicate a paced beat cycle (step 97) and transfers control to step 100. If the pacemaker did not pace, the data collection program checks whether the pacemaker sensed (step 98) this is performed by checking the event sensing status data which is stored for the current beat cycle by the pacemaker/ETC device 21 or by the pacing program operating the processing unit 61 of the analyzing unit 64. If the pacemaker sensed, the data collection program sets the value of the logical parameter to EV=SENSE to indicate a sensed beat cycle (step 99) and transfers control to step 100.

The data collection program then checks whether a premature ventricular contraction (PVC) was detected (step 100). The detection of a PVC is performed by the pacemaker/ETC device 21 or by the pacing program operating the processing unit 61 of the analyzing unit 64. A PVC may be detected using the signals sensed in the RV. As is known in the art, PVC's may be identified by detecting two consecutive ventricular events without an atrial event therebetween. For example, PVC detection methods used in pacemakers operating in a DDD mode are suitable for use in the data collection method of the present invention. However, other methods suitable for PVC detection may be used. PVC detection methods are well known in the art, are not the subject matter of the present invention and will therefore not be discussed in detail hereinafter.

If a PVC was detected the data collection program returns control to step 90 for avoiding collection of data for the current beat cycle. If a PVC was not detected, the data collection program gets the value of the variable ETC (step 101). The variable ETC is a logical variable which can have the values "ON" and "OFF". When ETC=OFF the histogram is assumed to represent data considered to be collected under conditions in which there was no practical influence of the prior delivery of ETC signals on the cardiac conduction velocity. When ETC=ON the histogram is assumed to represent data considered to be collected under conditions in which the delivery of ETC signals has some influence on the cardiac conduction velocity. The detailed procedure of setting the value of the variable ETC and the criteria used to set the value of the variable ETC are disclosed in detail hereinafter.

The program then determines the cycle length category CL (step 102). CL is a variable representing the cycle length category which holds an integer number in the range 1–CLENGTH, where CLENGTH is the number of cycle length categories.

The cycle length category is determined (step not shown) from the time interval between the current RV event detection and the previous RV event detection. This time interval is known in the art as the "R—R interval". The time of occurrence of detection of the current and previous RV events are stored in the memory of the pacemakers ETC device 21 of FIG. 3A or of the analyzing unit 64 of FIG. 5 as is known in the art.

The CL value of the current R—R interval is determined (steps not shown) by assigning the appropriate cycle length category CL depending on the current value of the R—R interval. The number of cycle length categories and the range of R—R interval lengths included in each of the cycle length categories are predetermined. For example, all R—R intervals having a value between 400 milliseconds and 449 milliseconds are assigned a first cycle length category variable value CL=1, all R—R intervals having a value between 450 milliseconds and 499 milliseconds are assigned a second cycle length category variable value CL=2, all R—R intervals having a value between 500 milliseconds and 549 milliseconds are assigned a third cycle length category variable value CL=3 and so forth.

It is noted that the above disclosed values of the ranges of the R—R intervals and CL values are given by way of example only and that the number of predetermined cycle length categories values CL which are selected and the selected ranges of the R—R intervals may be varied depending, inter alia, on the amount of memory available for data storage, the desired temporal resolution, the processing power of the processing unit 30 (FIG. 3A) or of the controller 40 (FIG. 4) and other practical considerations.

The program then selects a histogram to be updated HIST(EV,CL,SL,ETC) based on the current values of the variables EV,CL, SL and ETC and updates the number of beats contributing to the data accumulated in the selected histogram by increasing by one the value of a histogram beat counter HC(EV,CL,SL,ETC) associated with the selected histogram HIST(EV,CL,SL,ETC) (step 105). It is noted that, the value of all the plurality of histogram beat counters HC(EV,CL,SL,ETC) is set to zero at the start of the data collection procedure (step not shown). The program then sets the value of the variable TIME to zero (step 106) and starts a timer (step 108) which updates the value of the variable TIME representing the time from starting of the current RV event detection. The program then checks whether a threshold crossing has occurred (step 110). If a threshold crossing does not occur, the program checks whether the value of the variable TIME is equal to or larger than the value of the variable MAXDELAY (step 112) wherein MAXDELAY is a constant value representing the longest delay between a detected RV event and a detected LV event value for which the LV event is registered in a histogram. The value of MAXDELAY is represented by the data collection time interval 71 of FIG. 7, and is equal to the number of bins 72 multiplied by the bin duration 74 (FIG. 7).

If the value of the variable TIME is not equal to or larger than the value of the variable MAXDELAY, the program returns control to step 110. If the value of the variable TIME is equal to or larger than the value of the variable MAXDELAY, the program returns control to step 90.

If a threshold crossing occurs, the program calculates BINNUMBER the serial number of the time bin 72 within which the threshold crossing occurred (step 114). The bin number is calculated by dividing the current value of the variable TIME by the constant BINSIZE representing the duration of the time bins (BINSIZE is represented as the double headed arrow 74 of FIG. 7) and rounding the result up to the nearest integer value. The program then increments the event count associated with the time bin who's number BINNUMBER was calculated by step 114 by adding one to the value of the variable HIST[EV,CL,SL, ETC] (BINNUMBER) (step 116).

The program then stops sensing of the LV sensed signal for a blanking time period of BLANK_T (step 118). The blanking time period BLANK_T is used to prevent spurious event detection caused by LV events having multiple peaks. The program then checks whether the value of the variable TIME is larger than the value of the variable MAXDELAY (step 120). If the value of the variable TIME is not larger than the value of the variable MAXDELAY, the program returns control to step 110. If the value of the variable TIME is larger than the value of the variable MAXDELAY, the program returns control to step 90.

As the cycle length of the patient's heart beats varies during the data collection time period depending on the state of exertion of the patient and since the detection sensitivity level is typically automatically changed by the pacemaker/ETC device as is disclosed in detail hereinafter, the different histogram data sets will include at the end of the data collection period the cumulative time distribution histogram data for each unique data set.

In order to collect enough data histograms in the shorter cycle lengths categories, the patient may be asked by the cardiologist or physician to engage in physical activity. In the cases where the data is collected by the implanted pacemaker/ETC device 21 of FIG. 3A, the physician may instruct the patient to engage in a suitable physical activity regimen once a day or at any other suitable frequency. If the data collection is done using the system 60, the physician or user may stop data collection, disconnect the leads 22 from the analyzing unit 64 and ask the patient to perform a suitable physical activity or exercise to increase his heart rate. The physician or user then reconnects the leads 22 to the analyzing unit 64 and continues the data collection.

Additionally, in order to get adequate data collection including sufficient data for both paced and sensed events, the pacemaker A-V delay may be changed. For example, when the data is collected by using the system 60 of FIG. 5, the A-V delay be changed by a physician during the data collection period, by reprogramming the value of the A-V delay using the user interface device(s) 69. In another example, when the data is collected by using the implanted pacemaker/ETC device 21 of FIG. 3A, once each night (by system clock) the sum of the histogram beat counters HC(EV,CL,SL,ETC) of all sensed histograms HIST(EV,CL, SL, ETC) having EV=0 is computed to obtain a first sum representing the total number of sensed beats collected. The sum of the histogram beat counters of all paced histograms HIST(EV,CL,SL,ETC) having EV=1 is also computed to obtain a second sum representing the total number of paced beats collected. The ratio of the first sum and the second sum is then computed. If the computed ratio is smaller than a pre-selected lower limit such as, but not limited to, 1:20 (paced beats: sensed beats), the A-V delay is shortened. A-V delay shortening by approximately 20 milliseconds will typically lead to more paced beats. If the computed ratio is larger than a pre-selected upper limit such as, but not limited to 20:1 (paced beats: sensed beats), the A-V delay is lengthened by approximately 20 milliseconds for obtaining more sensed beats. In order to restrict the range of possible automatic modification of the A-V delay, high and low limits for A-V delay may be set. For example, a low A-V delay limit of 100 milliseconds and a high A-V delay limit of 300 milliseconds may be set but other different limit values may also be used.

Methods for adjusting the A-V delay of a pacemaker are known in the art. For example, U.S. Pat. No. 5,749,906 to Kieval discloses a method including adjustment of the A-V delay to achieve certain pacing conditions.

Alternatively, In cases were it is not possible to automatically adjust the A-V delay, if after the data was off-loaded, the user or the cardiologist finds that not enough data histograms for paced events were recorded, the A-V delay value of the pacemaker/ETC device may be shortened to increase the number of paced events and the patient may be sent away for an additional data collection period.

It is noted that the value of SL is set by an independent program (not shown). Various methods (not shown) for changing the detection sensitivity level may be used (not shown). Preferably, the value of SL is set to a number randomly selected from a group of numbers representing the available sensitivity levels of the pacemaker/ETC device. Alternatively, pseudo-random selection of the sensitivity level values may be used. Additionally, the method may use various forms of cycling of the sensitivity level. The rate of changing of the sensitivity level may be constant or variable. For example, the changing of the sensitivity level may be cyclic, pseudo-random or random, as long as data from enough beats is accumulated for each sensitivity level. The rate of change of the sensitivity level may be fixed, may change according to the time of day, or may be relatively rapid, such that data using the same sensitivity level would be recorded at different hours on different days. The latter rapid sensitivity change method may be useful in view of the fact that patient's behavior is probably different at different times during the day.

Figure 9:
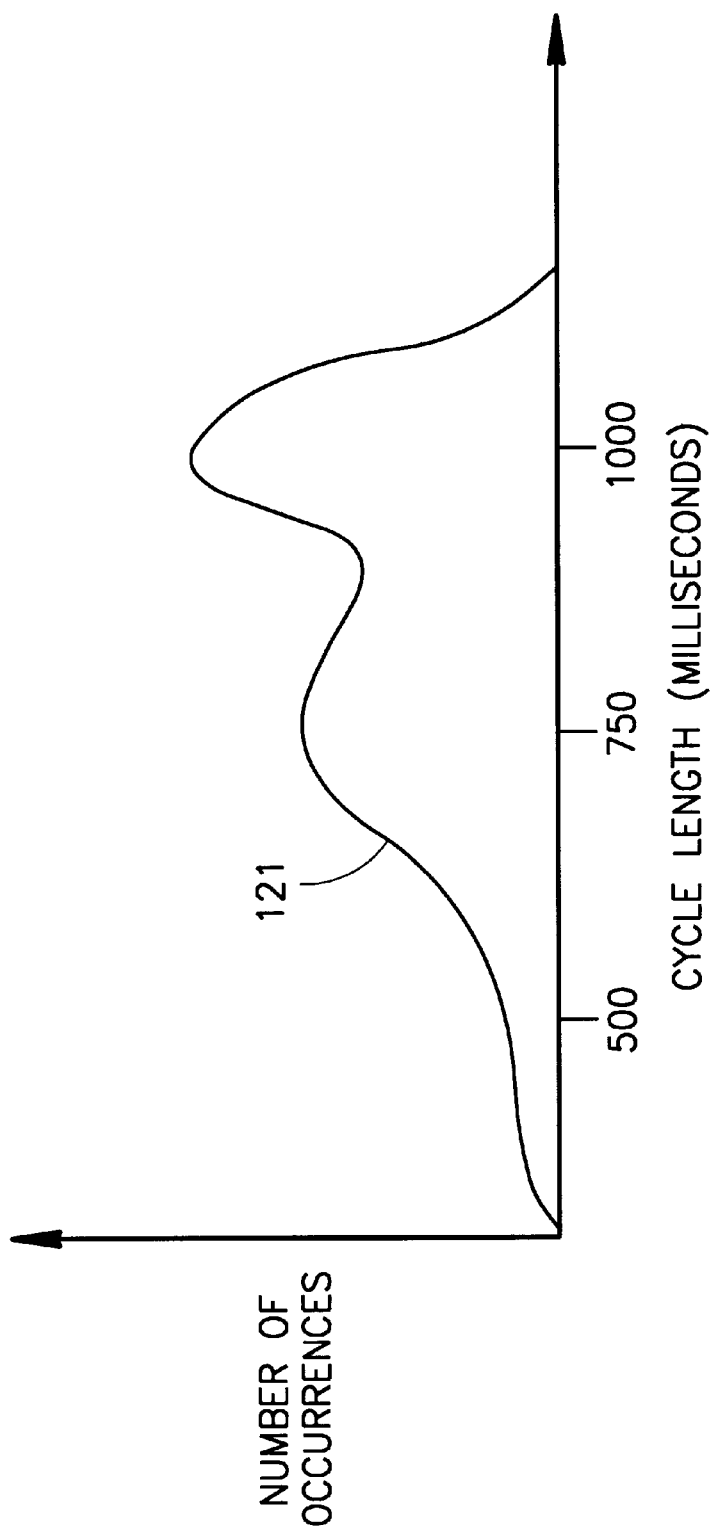
FIG. 9 is a schematic graph illustrating a typical cumulative distribution of cardiac cycle length.

Reference is now made to FIG. 9 which is a schematic graph illustrating a typical cumulative distribution of cardiac cycle length. The horizontal axis represents the cycle length in milliseconds and the vertical axis represents the number of occurrences accumulated over the sampling period for a particular cycle length. The curve 121 represents a typical cycle length cumulative distribution curve which is well known in the art. The data for such a curve may be collected over a sampling period of a few hours or a few days. It is noted that, while the overall cumulative distribution of cycle length may be similar to the exemplary curve 121 of FIG. 9, the longer cycle lengths are more frequent while sleeping (at night), and shorter cycles will be more frequent during working hours.

It is noted that when the pacemaker/ETC device 21 of FIGS. 3 and 4 is used for collecting data, the amount of storage available on the memory unit 44 may be practically limited due to, inter alia, size, cost and current consumption of avaliable memory units. This memory limitation may have to be taken into account with respect to the amount of histogram data that may be simultaneously stored in the memory 44. For example, turning briefly to FIG. 7, each of the bins 72 of the data collection time interval 71 may be allocated 3 bytes of memory space. The data collection time interval 71 may be divided into 100 bins 72, each of the bins 72 spanning a time interval 74 of 2 milliseconds. Twelve cycle length categories CL are pre-set. Each of the 12 cycle length categories CL is associated with cycle lengths falling into the twelve equal duration ranges 999–950 milliseconds, 949–900 milliseconds, . . . , 449–400 milliseconds. If eight different sensitivity levels SL are used and data is collected for paced and for sensed beat cycles and if a histogram header of 3 bytes is included in each histogram, the required amount of bytes that needs to be allocated for data histogram storage under such requirements is given by $(3\times100+3)\times12\times8\times2=58{,}176$ bytes. If histogram data is also collected for sensed and paced beat cycles under ETC delivery conditions which are the histograms HIST[EV, CL SL, ETC] having ETC=ON, 116,352 bytes need to be allocated for histogram data storage.

Memory may be saved by using dynamic memory allocation techniques known in the art.

It is noted that, the particular cycle beat ranges (cycle length categories) disclosed hereinabove are given by way of example only and other different cycle-length categories having different cycle-length ranges may be used. Additionally, while the cycle length categories disclosed hereinabove have cycle length ranges of equal size, in other preferred embodiments of the present invention the data collection method may also use cycle length categories having non-identical R—R interval collection ranges. For example, all R—R intervals having a value between 400 milliseconds and 449 milliseconds may be assigned a first cycle length category variable value CL=1, all R—R intervals having a value between 450 milliseconds and 549 milliseconds are assigned a second cycle length category variable value CL=2, all R—R intervals having a value between 550 milliseconds and 669 milliseconds may be assigned a third cycle length category variable value CL=3 and so forth.

Figure 10:
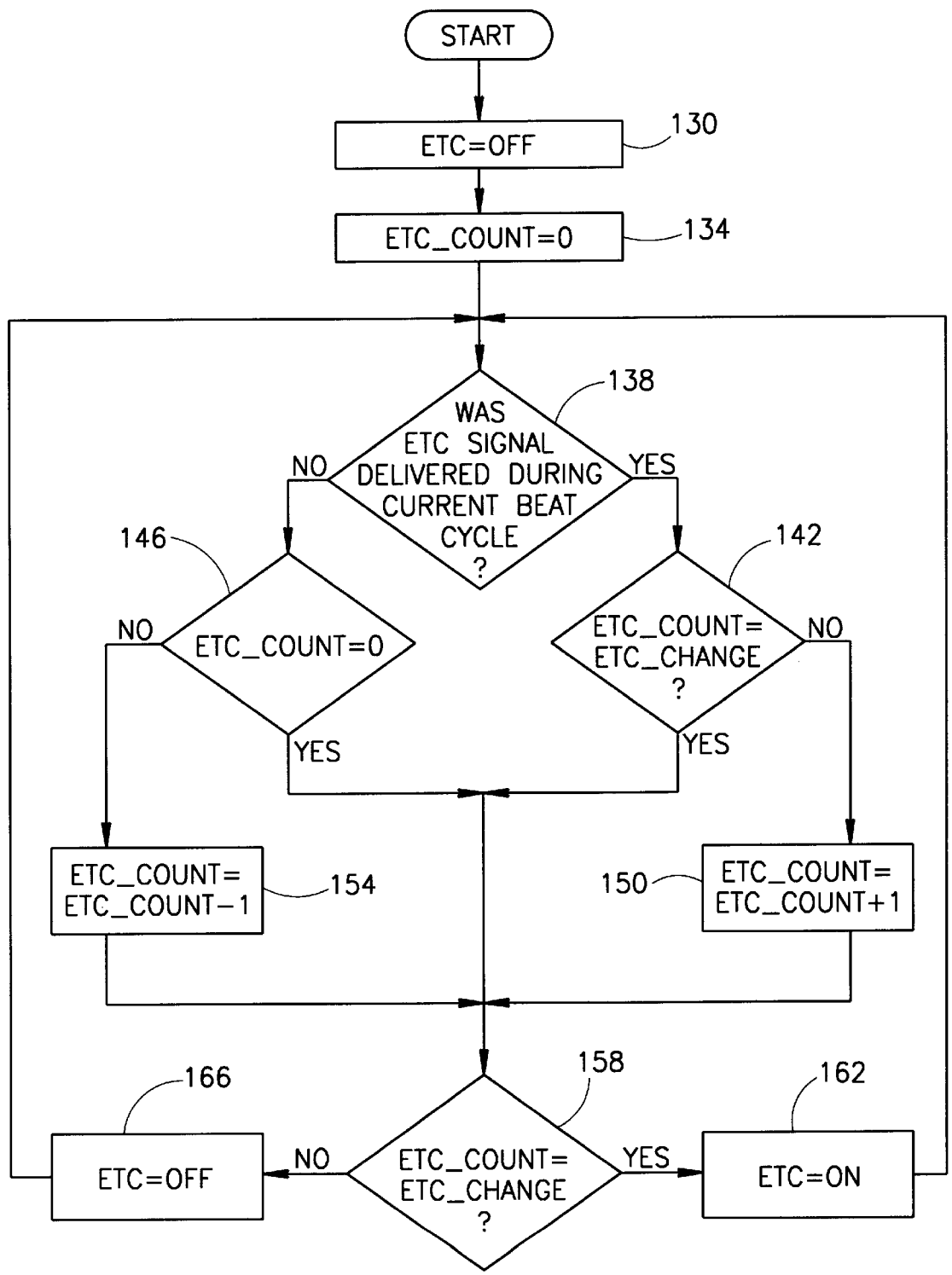
FIG. 10 is a schematic diagram illustrating the steps of the method of updating the value of the logical variable ETC of FIGS. 8B–8C.

Reference is now made to FIG. 10 which is a schematic diagram illustrating the steps of the method of updating the value of the logical variable ETC of FIGS. 8B–8C.

The method may be implemented as a software program which is executed in parallel with the program of FIGS. 8B–8C. on the controller unit 40 of the pacemaker/ETC device 21 or on the processing unit 61 of the analyzing unit 64 or on any other suitable processing unit which is used for data collection in the present invention.

The program starts by setting the value of the logical variable ETC to ETC=OFF (step 130). The program then sets the value of the counter ETC_COUNT to zero (step 134). The program then checks whether an ETC signal was delivered during the current beat cycle (step 138). If an ETC signal was delivered during the current beat cycle, the program checks whether ETC_COUNT=ETC_CHANGE (step 142). ETC_CHANGE is a preset integer constant. The value of ETC_CHANGE is a fixed preset value. Typically, the value of ETC_CHANGE is empirically found and may depend, inter alia, on the intensity, waveform shape, polarity and duration of the delivered ETC stimulation. Typically, the value of ETC_CHANGE may be in the range of approximately 2–8, For example, the value of ETC_CHANGE=6 may be used. However, other values of the ETC_CHANGE may be used.

If an ETC signal was not delivered during the current beat cycle, the program checks whether ETC_COUNT=0 (step 146).

In step 142, if ETC_COUNT is equal to ETC_CHANGE control is transferred to step 158. If ETC_COUNT is not equal to ETC_CHANGE the program increments the current value of ETC_COUNT by one (step 150) and transfers control to step 158.

In step 146, if ETC_COUNT=0, the program transfers control to step 158 and if ETC_COUNT is not equal to zero the program decrements the current value of ETC_COUNT by one (step 154) and transfers control to step 158.

In step 158 the program checks whether ETC_COUNT= ETC_CHANGE. If ETC_COUNT=ETC_CHANGE, the program sets the value of the parameter ETC to ETC=ON (step 162) and returns control to step 138. If ETC_COUNT is not equal to ETC_CHANGE, the program sets the value of the parameter ETC to ETC=OFF (step 166) and returns control to step 138. The program of FIG. 10 thus updates the value of the logical parameter ETC for the current beat cycle.

It is noted that, the procedure for updating the value of the logical variable ETC disclosed hereinabove and illustrated in FIG. 10 is implemented as a precaution in case the prior application of ETC signals does have an effect on the velocity of propagation of a depolarization wave in a portion of the myocardium disposed between the electrode 4A in the RV and the electrode 6A in the LV (or in the portion of the myocardium disposed between the electrode 2A in the RA and the electrode 6A in the LV when the sensing is performed by the electrodes 2A and 6A). If the prior application of ETC signals does not have a substantial effect on the velocity of propagation of the depolarization wave (as has been found in preliminary experimental results in a small number of human patients), the data histograms collected for cardiac conditions differing only in the value of the parameter ETC may be redundant. For example, the histogram pairs HIST(EV, CL, ETC=ON) and HIST(EV, CL, ETC= OFF), may be redundant. However, having such redundant histograms does not adversely affect the method of the present invention since in such a situation the sets of alert time window parameters corresponding with the histogram pairs have identical or similar values. Thus, the data set including these pairs of sets of redundant sets of alert time window parameters becomes a partially degenerate data set without adversely affecting the method of the present invention. When such a degenerate data set is used for setting the beginning time point and ending time point of the alert time window, the timing of the alert window will be correctly set since all the sets of alert time window parameters are computed from actual sampled data, irrespective of whether one or more of these sets is redundant.

Ensuring acquisition of paced and sensed data in order to collect data for all sensitivity level values for each cycle length value of paced and sensed events with and without ETC stimulation, the sensitivity level is automatically changed by the pacemaker/ETC device 21 or by the analyzing unit 64. The order of change might be cyclic, pseudo-random or random, as long as a sufficient number of beats is sampled for each sensitivity level. The rate of change of the sensitivity level may be fixed, changing relative to the time of day, or may be changed relatively fast, so that data collected with the same sensitivity level would be collected at different hours on different days, as the patients' behavior is probably different at different times during the day. While the overall distribution of cycle length might be similar to FIG. 9, the longer cycle lengths are typically more frequent while sleeping (at night), and shorter cycle lengths are typically more frequent during working hours. Thus, preferably, the sensitivity level is randomly or pseudo-randomly changed every beat cycle to prevent biasing of the results due to time of day bias of cycle length.

Data processing and analysis methods

After enough data was collected by the data collection program of FIGS. 8B–8C, the data is telemetrically off-loaded from the pacemaker/ETC device 21 to the analyzing unit 24 of the system 20 for further processing. Alternatively, if the system 60 has been used, the data is stored in memory unit 66 and is available for further processing by the processing unit 61.

Figure 11A:
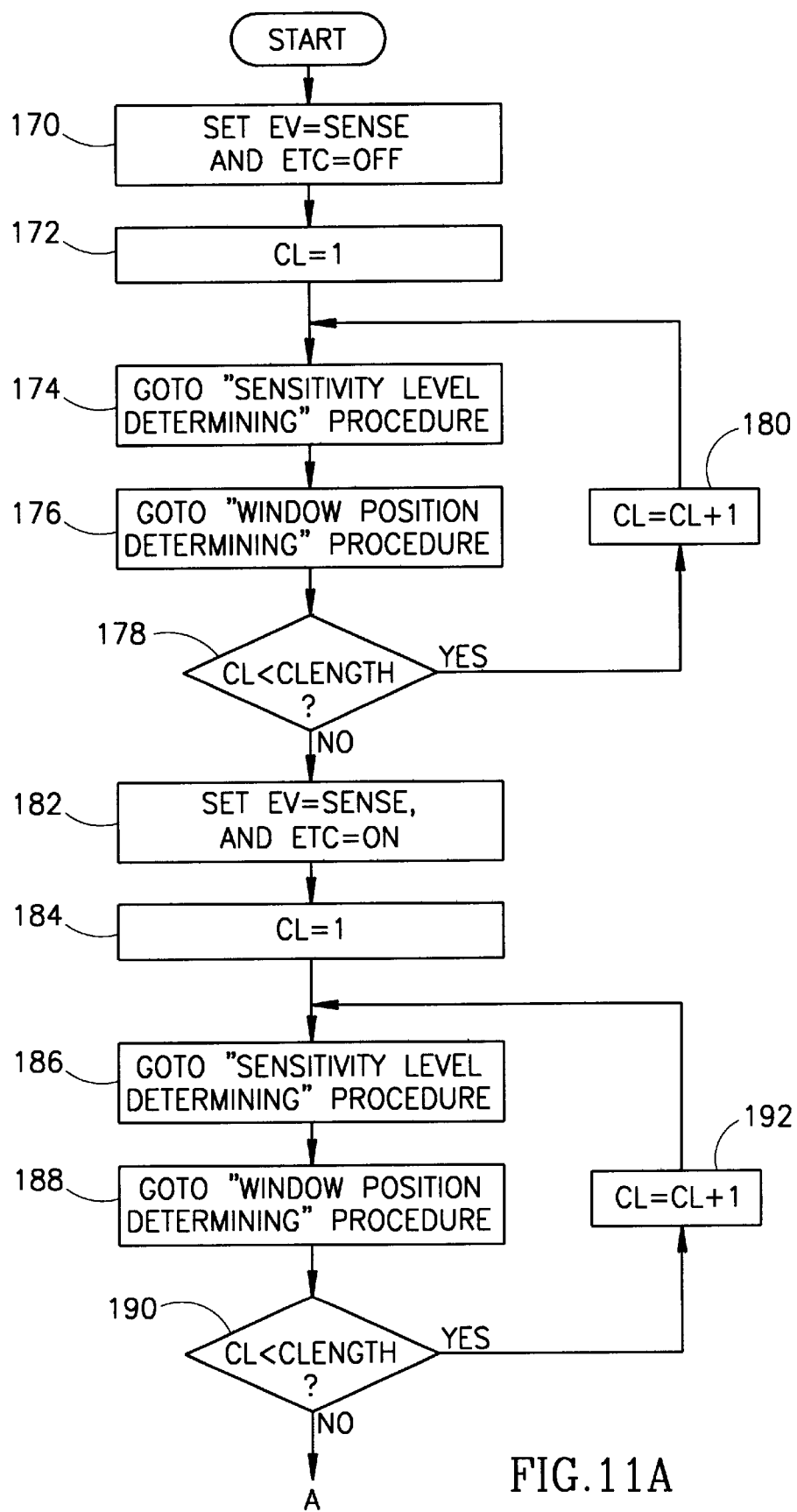
FIGS. 11A and 11B are schematic control flow diagrams of the main program implementing the method for analyzing acquired data histograms, in accordance with a preferred embodiment of the present invention.
Figure 11B:
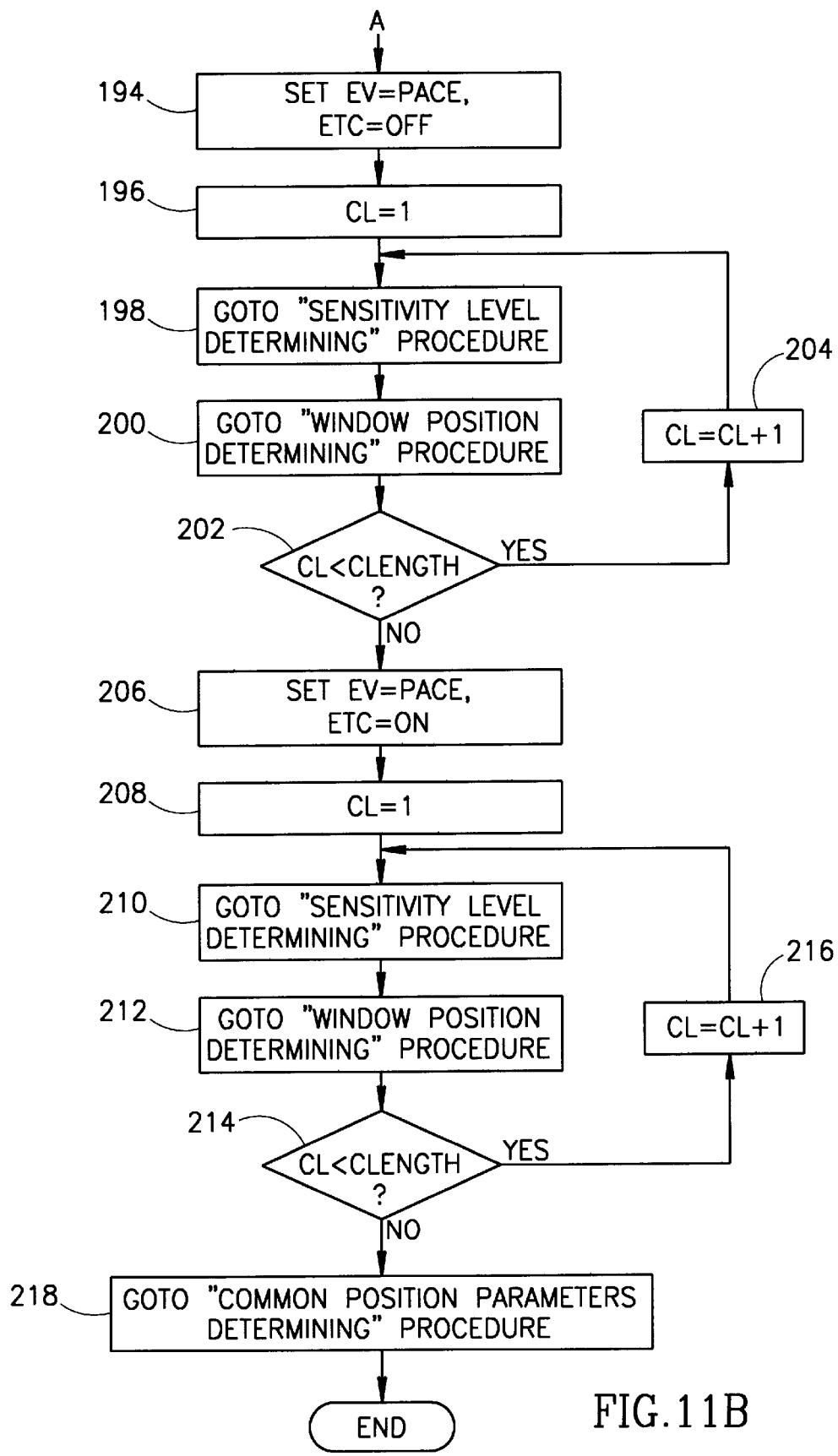

Reference is now made to FIGS. 11A and 11B which are schematic control flow diagrams of the main program implementing the method for analyzing acquired data histograms, in accordance with a preferred embodiment of the present invention.

The main program uses the data histograms collected as disclosed in hereinabove and illustrated in FIGS. 7 and 8 to determine the alert window parameters under a variety of different cardiac conditions. The conditions include paced and sensed events, the absence and in the presence of ETC signals and a plurality of different cycle length ranges. The main program determines a set of appropriate alert window parameters and an appropriate amplifier sensitivity level for each of the above conditions.

The main program starts to analyze the collected data histograms for sensed events in the absence of ETC signal delivery by setting the value of the parameters EV, and ETC as follows EV=SENSE, ETC=OFF (step 170). The program then sets the value of the cycle length category parameter CL to CL=1 (step 172). The program then transfers control to a sensitivity level determining procedure for determining the appropriate sensitivity level SL for the particular histogram having CL=1 (step 174). The sensitivity level determining procedure is disclosed in detail hereinafter. The program then transfers control to a window position determining procedure for determining the alert window position parameters GROUPMIN and GROUPMAX for the particular histogram having CL=1 (step 176). The parameters GROUPMIN and GROUPMAX are defined in detail hereinafter.

The main program then checks whether the current value of the cycle length category parameter CL is smaller than the number of the cycle length categories CLENGTH (step 178). For example, the total number of cycle length categories used in collecting the data may be twelve cycle length categories as in the non-limiting example given hereinabove (CLENGTH=12) but other values of CLENGTH may be used according to the total number of cycle length categories used in collecting the data. If CLENGTH is greater than CL, the program increments the value of CL by 1 (step 180) and returns control to step 174 for determining the alert window parameters SL, GROUPMIN and GROUPMAX of the next cycle length category. If CLENGTH is not greater than CL, the program transfers control to step 182.

In step 182, the program proceeds to analyze the collected data histograms for sensed events in the presence of ETC signal delivery by setting the value of the parameters EV, and ETC as follows EV=SENSE, ETC=ON. The program then sets the value of the cycle length category parameter CL to CL=1 (step 184). The program then transfers control to the sensitivity level determining procedure for determining the appropriate sensitivity level SL for the particular histogram having CL=1 (step 186). The program then transfers control to the window position determining procedure for determining the alert window position parameters GROUPMIN and GROUPMAX for the particular histogram having CL=1 (step 188).

The main program then checks whether the current value of the cycle length category parameter CL is smaller than the number of the cycle length categories CLENGTH (step 190). If CLENGTH is greater than CL, the program increments the value of CL by 1 (step 192) and returns control to step 186 for determining the alert window parameters SL, GROUPMIN and GROUPMAX of the next cycle length category. If CLENGTH is not greater than CL, the program transfers control to step 194.

In step 194, the program proceeds to analyze the collected data histograms for paced events in the absence of ETC signal delivery by setting the value of the parameters EV, and ETC as follows EV=PACE, ETC=OFF. The program then sets the value of the cycle length category parameter CL to CL=1 (step 196). The program then transfers control to the sensitivity level determining procedure for determining the appropriate sensitivity level SL for the particular histogram having CL=1 (step 198). The program then transfers control to the window position determining procedure for determining the alert window position parameters GROUPMIN and GROUPMAX for the particular histogram having CL=1 (step 200).

The main program then checks whether the current value of the cycle length category parameter CL is smaller than the number of the cycle length categories CLENGTH (step 202). If CLENGTH is greater than CL, the program increments the value of CL by 1 (step 204) and returns control to step 198 for determining the alert window parameters SL, GROUPMIN and GROUPMAX of the next cycle length category. If CLENGTH is not greater than CL, the program transfers control to step 206.

In step 206, the program proceeds to analyze the collected data histograms for paced events in the presence of ETC signal delivery by setting the value of the parameters EV, and ETC as follows EV=PACE, ETC=ON. The program then sets the value of the cycle length category parameter CL to CL=1 (step 208). The program then transfers control to the sensitivity level determining procedure for determining the appropriate sensitivity level SL for the particular histogram having CL=1 (step 210). The program then transfers control to the window position determining procedure for determining the alert window position parameters GROUPMIN and GROUPMAX for the particular histogram having CL=1 (step 212).

The main program then checks whether the current value of the cycle length category parameter CL is smaller than the number of the cycle length categories CLENGTH (step 214). If CLENGTH is greater than CL, the program increments the value of CL by 1 (step 216) and returns control to step 210 for determining the alert window parameters SL, GROUPMIN and GROUPMAX of the next cycle length category. If CLENGTH is not greater than CL, the program transfers control to the common window parameter determining procedure for computing a parameter set suitable for all cycle length categories and all cardiac conditions, based on the SL, GROUPMIN and GROUPMAX values computed for all the various cardiac conditions disclosed hereinabove (step 206).

After successful analysis of the available histogram data is completed by the main program the result may be an array or Look up table including the alert window parameter sets associated with each of the specific combinations of the parameters EV, CL, and ETC representing all the various cardiac conditions as disclosed hereinabove. Alternatively, the analysis may result in a single set of alert window parameters commonly used for all the various cardiac conditions as disclosed hereinabove.

Figure 12:
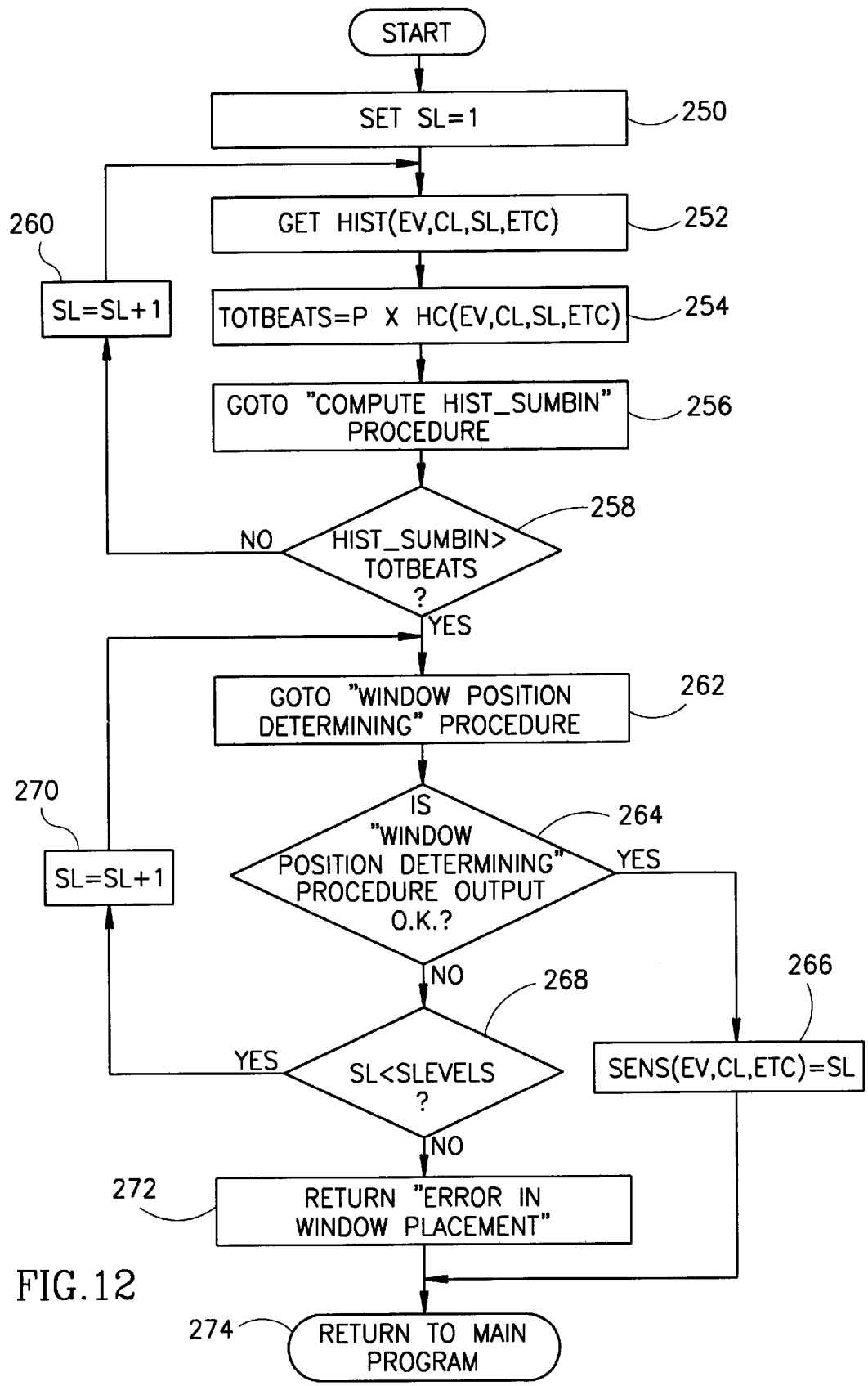
FIG. 12 is a schematic flow control diagram illustrating the steps of the sensitivity level determining procedure used in the main program of FIGS. 11A–11B.

Reference is now made to FIG. 12 which is a schematic flow control diagram illustrating the steps of the sensitivity level determining procedure used in the main program of FIGS. 11A–11B. The sensitivity level determining procedure is used for determining the appropriate sensitivity level and the alert window parameters for a particular cycle length. The data histogram which was acquired using the lowest sensitivity level (the highest threshold for the specific exemplary case of using a single positive threshold level) is processed first. The sum of detected events recorded in the data histogram is compared to the expected cumulative number of detected events for the current data histogram (TOTBEATS). If not enough events were detected, this indicates that the sensitivity level was too low (the threshold is too high), and the data histogram acquired using the next (higher) sensitivity level is processed next.

Ideally, only events that are synchronized to the heart activity, namely the sensing of the ventricle beat in the LV, are supposed to be recorded in the data histograms. However, practically, various types of spurious events may be detected and included in the data histogram. Such spurious ("false") detected events may include electrical depolarization events associated with PVCs and non-random electrical noise peaks which are cyclic or almost cyclic in nature and therefore occur within the alert window period triggered by the RV. The spurious detected events may also include lead movement artifacts which are likely to be synchronized to heart activity, and may therefore appear in a relatively stable position within the data collection time interval 71 of FIG. 7, and electrical Artifacts which are due to skeletal muscle activation which may or may not be synchronized with the cardiac cycle. Spurious detected events may also include polarization artifacts which are electrical noise generated by the activation of parts of the ventricle different from the ventricle's part or site at which the sensing is performed. When the heart is also paced, the spurious events may include pacing artifacts. During data acquisition, the detection time of the LV depolarization event may drift within the data collection time interval 71 because the detection of spurious events in the RV such as electrical noise, depolarization due to PVCs, and the like may lead to premature initiation of data acquisition in the data collection time interval 71.

In addition to the recording of spurious (false) events in the data histograms, It is may also happen that a "true" event is not recorded in a data histogram even though a depolarization wave did occur in the RV, because the depolarization wave was not conducted to the LV.

If enough detected events are recorded in the data histogram, the procedure attempts to establish the alert window parameters. A suitable window may not be found if the sensitivity level was such that not all the actual events registered, but some noise did register as detected events. In such a case, the procedure may get enough events registered in the histogram, but the events will be spread out among the bins. In this case, the procedure will consider a higher sensitivity level. If the procedure succeeds in finding suitable alert window, the sensitivity level for the analyzed histogram is recorded, otherwise an appropriate error message is returned to inform the user of the failure to establish an appropriate alert window for the currently analyzed data histogram.

Thus, preferably, the beginning time point and the ending time point of the alert window are determined such that they are optimized for a predetermined level of LV event detection, while reducing the probability of spurious event detection.

If, for any of the above disclosed reasons, no adequate alert window was found (although there where more events recorded than actual beats happening), the next (higher) sensitivity level is processed. If no appropriate window is found for any of the sensitivity levels (of a particular combination of values of CL,EV and ETC, an error message is returned. The steps of the sensitivity level determining procedure are disclosed in detail hereinbelow.

The sensitivity level determining procedure starts by setting the value of the sensitivity level SL to SL=1 which is the lowest sensitivity level used for the detection (step 250). For example, if the detection method uses only a single positive threshold crossing criterion, the value SL=1 represents the highest voltage threshold level which was used in data collection. Similarly, if the detection method uses another different detection criterion or combination criteria SL=1 will represent the least sensitive detection criterion level or the least sensitive combination of detection criteria which in use will lead to the smallest number of detections, SL=2 will represent the second least sensitive detection criterion level or the second least sensitive combination of detection criteria and the last sensitivity level will represent the most sensitive detection criterion level.

The procedure then gets the data histogram array HIST (EV,CL,SL,ETC) (step 252). The procedure then computes the value of the variable TOTBEATS for the current histogram HIST(EV,CL,SL,ETC) by multiplying the preset parameter P by the value of the histogram beat counter HC(EV,CL,SL,ETC) (step 254). The variable TOTBEATS represents the expected cumulative number of detected events for the current data histogram HIST(EV,CL,SL, ETC). The value of histogram beat counter variable HC(EV, CL,SL,ETC) is the actual number of beats included in the recorded data histogram HIST(EV,CL,SL,ETC) (see step 105 of FIG. 8C). The parameter P is a preset parameter representing the desired minimum probability of event detection (assuming no noise is present). For example, If the preset desired minimum probability of event detection is P=0.98 and the current histogram HIST(EV,CL,SL,ETC) includes data recorded from 100,000 heart beats, the computed value is TOTBEATS=0.98×100,000=98,000 detected events.

The procedure then transfers control to a procedure for computing and returning the value of the variable HIST_SUMBIN (step 256). The steps of the procedure for computing the value of the variable HIST_SUMBIN are disclosed in detail hereinafter (see FIG. 14). Briefly, the variable HIST_SUMBIN represents the total sum of the number of detected events which are recorded in all the bins 72 of the data collection time interval 71 (FIG. 7) and which are stored in the current data histogram HIST(EV,CL,SL, ETC). The procedure then checks whether the current value of HIST_SUMBIN is larger than the value of the parameter TOTBEATS (step 258).

If the current value of HIST_SUMBIN is not larger than the value of the computed parameter TOTBEATS, indicating that the desired value of TOTBEATS is not achievable using the current sensitivity level SL, the procedure increments the value of the parameter SL by 1 (step 260) and transfers control to step 252. If the current value of HIST_SUMBIN is larger than the value of the computed parameter TOTBEATS, this indicates that the desired value of TOT- BEATS is achievable using the current sensitivity level SL, and the procedure transfers control to the window position determining procedure (step 262).

The procedure then checks the output returned by the window position determining procedure (step 264). If the window position determining procedure returned the value "OUTPUT OK", the procedure updates the variable SENS (EV, CL, ETC) which represents the appropriate sensitivity level for cycle length category CL, the current event variable EV and the current excitable tissue control variable ETC, by setting SENS(EV,CL,ETC)=SL (step 266) and returns control to the main program (step 274). If the window position determining procedure did not return the value "OUTPUT OK", the procedure checks whether SL<SLEVELS (step 268). If the current sensitivity level value SL is smaller than the number of sensitivity levels SLEVELS, the procedure increments the value of SL by 1 (step 270), and returns control to step 262. If the current sensitivity level value SL is not smaller than the number of sensitivity levels SLEVELS, the procedure returns an error message "ERROR IN WINDOW PLACEMENT" (step 272) and returns control to the main program (step 274). In such a case the data set is not considered adequate for generating a complete set of alert window parameters.

Figure 13A:
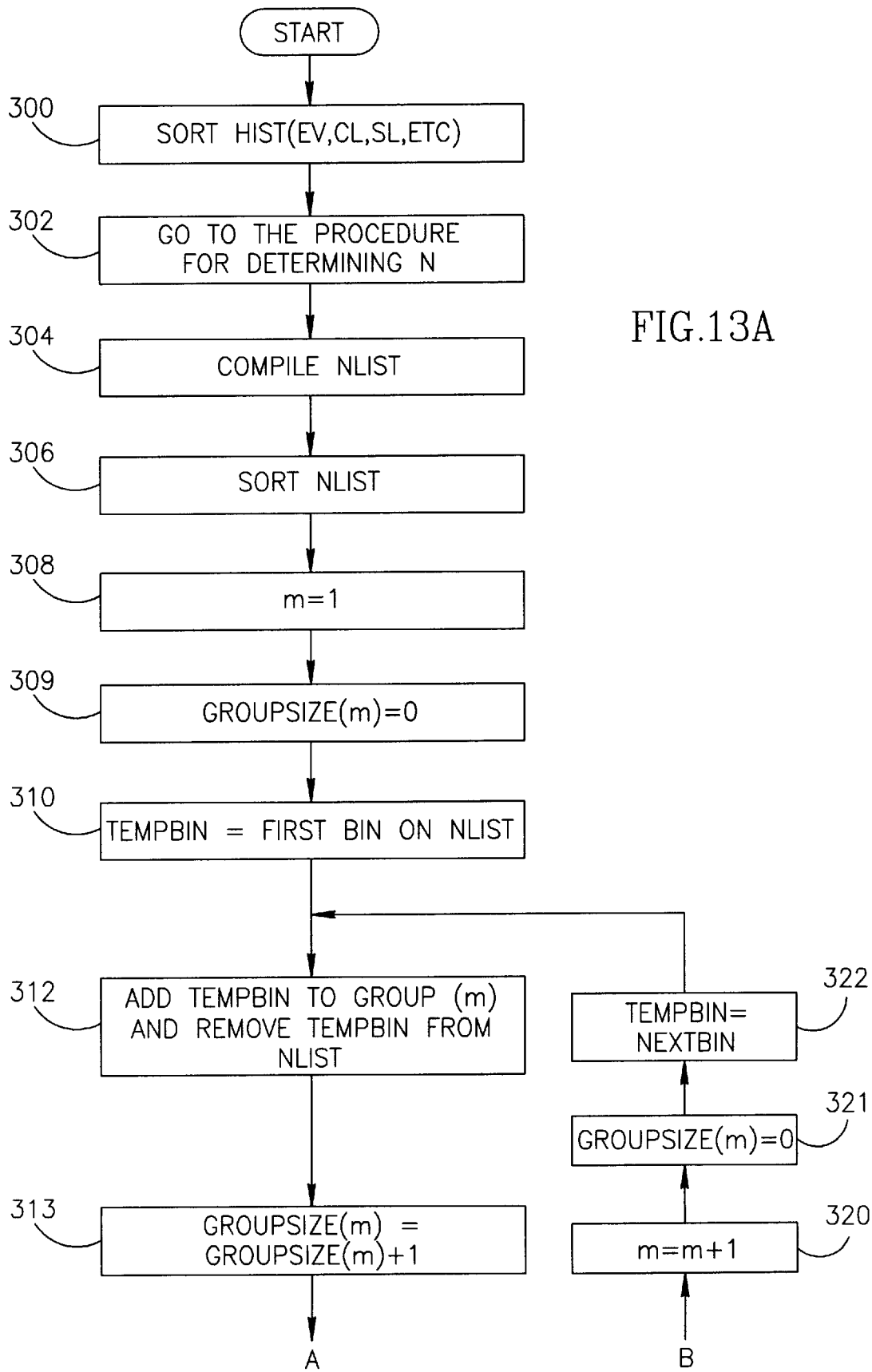
FIGS. 13A–13C are schematic flow control diagrams illustrating the steps of the window position determining procedure used in FIGS. 11A, 11B and in FIG. 12.
Figure 13B:
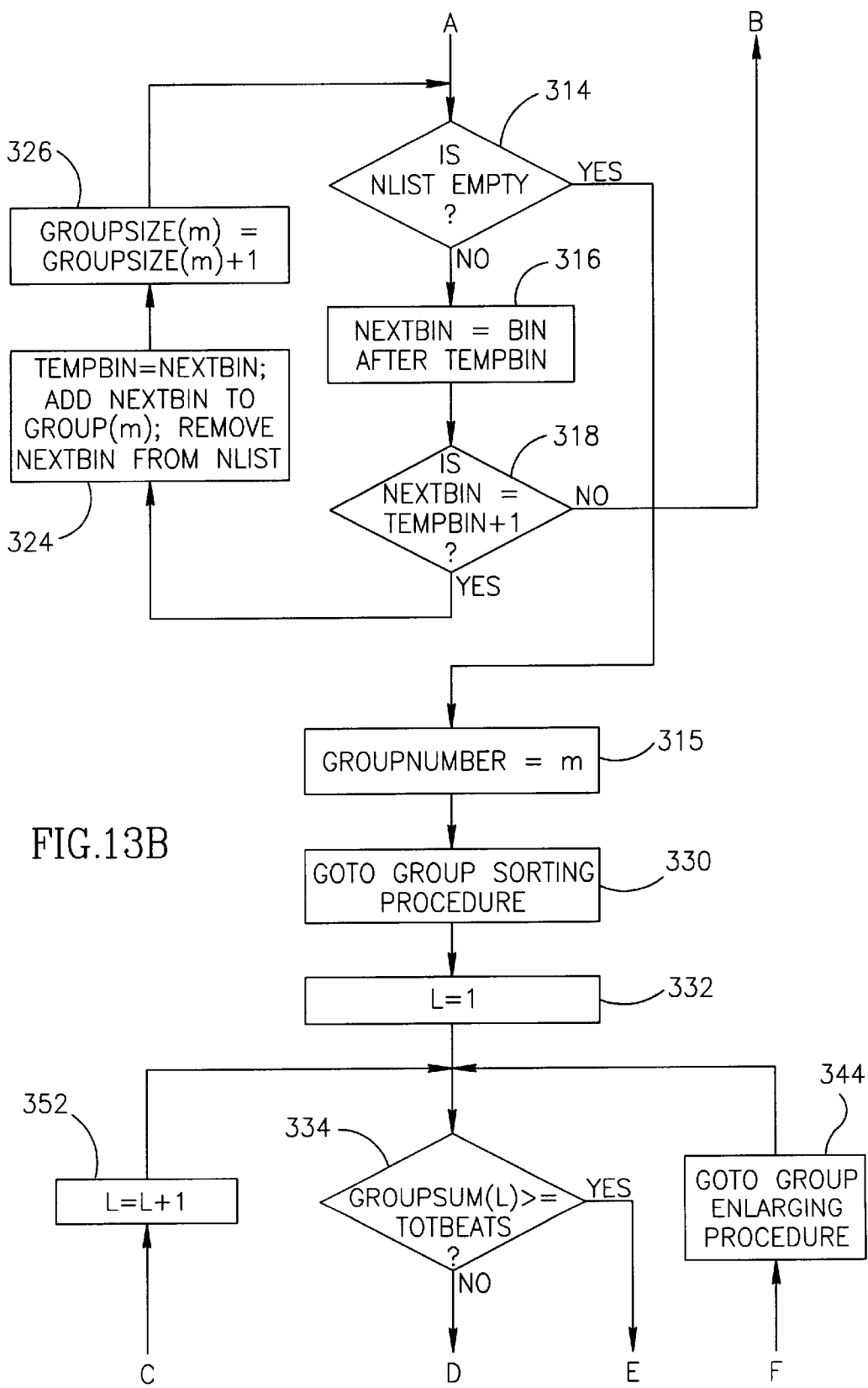
Figure 13C:
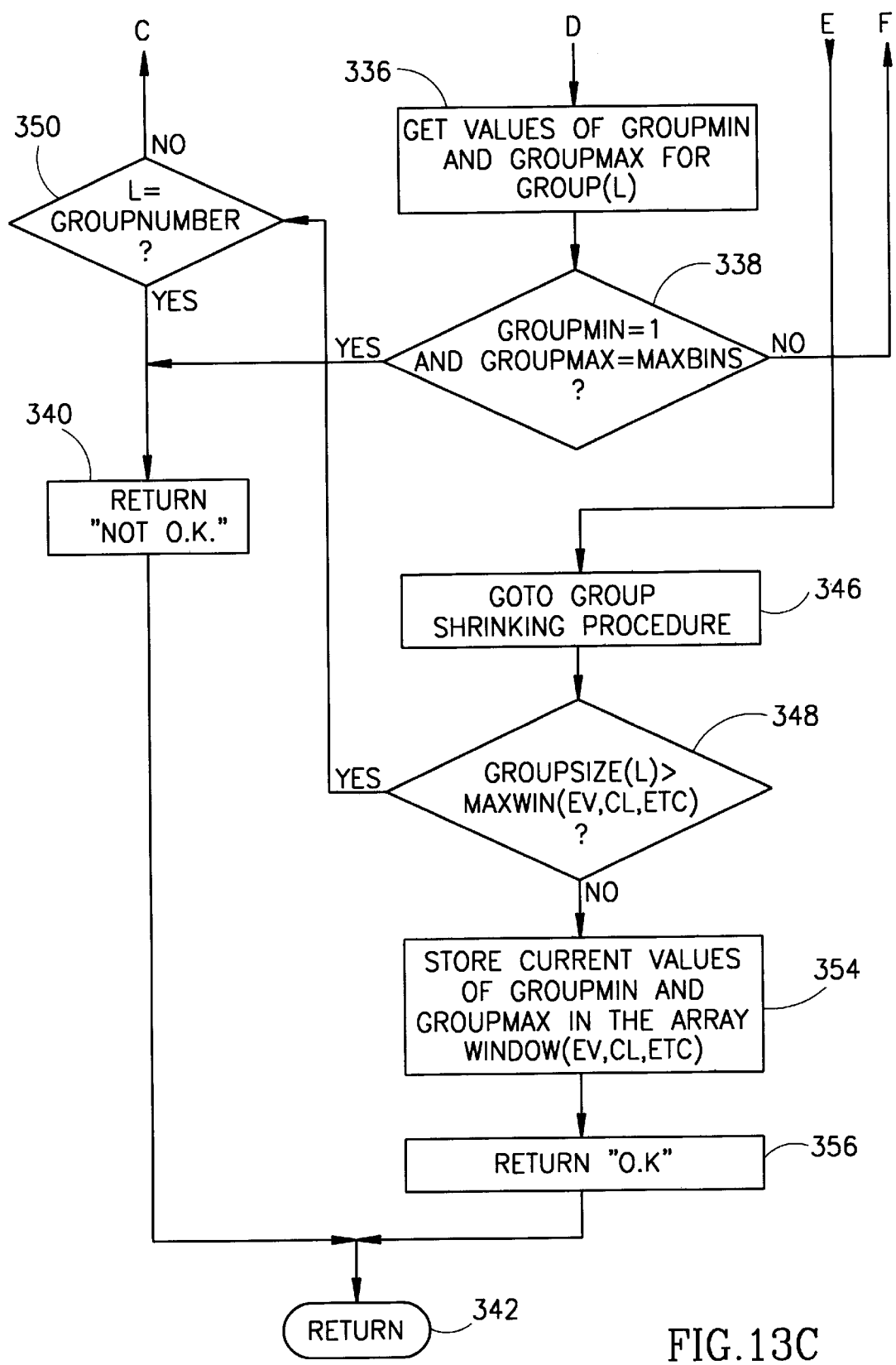

Reference is now made to FIGS. 13A–13C which are schematic flow control diagrams illustrating the steps of the window position determining procedure used in FIGS. 11A, 11B and in FIG. 12.

The window position determining procedure of FIGS. 13A–13C is used to determine the alert window parameters. The procedure returns for each histogram HIST(EV,CL,SL, ETC), a pair of values, representing the starting (earliest) bin number and the ending (latest) bin number of the alert window appropriate for the current histogram. These pairs of starting and ending bin numbers are stored in an array WINDOW(EV, CL,ETC) in which array, for each specific combination of cycle length category value CL, EV value and ETC value there are stored a pair of integer numbers representing the starting bin number and the ending bin number for the alert window determined based on the analysis of the data histogram HIST(EV,CL,SL,ETC) having this specific combination CL, EV and ETC values.

The window position determining procedure starts by sorting the bins of the current histogram HIST(EV,CL,SL, ETC) (step 300). Generally, the number of events recorded in the group of bins constituting an alert window should be at least TOTBEATS events and the number of bins within any alert window is limited to MAXWIN bins. The bin sorting step 300 may be performed by sorting the bins in descending order of bin value wherein the bin value is the number of events accumulated in a particular bin. The sorting of step 300 may be accomplished by any suitable sorting method such as a heap sort, a bubble sort or by any other suitable sorting method known in the art. Thus, the step 300 results in a sorted list of bins. Next, the procedure finds the number N which is the minimum number of bins containing more than TOTBEATS of recorded events by going to the N determining procedure and returning a value for N (step 302).

The procedure then compiles a bin list NLIST including the first N bins within the current histogram (step 304). The procedure then sorts the list NLIST by ascending bin number (step 306). The sorting method may be similar to the sorting method used in step 300 hereinabove except that the sorting is performed according to bin number and not according to the bin value. However, any other suitable sorting method known in the art may be used in step 306.

The procedure then sets the value of an integer group counter m to m=1 (step 308) The procedure thus defines first a bin group GROUP(1) of a number of bin groups GROUP (m). The procedure sets to zero the value of the parameter GROUPSIZE(m) which represents the number of bins currently included in the bin group GROUP(m) (step 309). The procedure stores the value of the bin number of the first bin on the list NLIST in the variable TEMPBIN (step 310). The procedure then adds the bin number TEMPBIN of the first bin on NLIST as the first bin number of the bin group GROUP(m) and removes the bin number TEMPBIN from the bin list NLIST (step 312). The procedure then increments the value of the parameter GROUPSIZE(m) by 1 (step 313). The procedure then checks whether NLIST is empty (step 314). If NLIST is empty, there is only one group of bins containing one bin and the procedure updates the parameter GROUPNUMBER representing the current number of groups by setting GROUPNUMBER=m (step 315), and transfers control to the group sorting procedure of step 330 for group sorting. If NLIST is not empty, the procedure proceeds by storing the number of the next bin after TEMPBIN in the list NLIST in the variable NEXTBIN (step 316). The procedure then checks whether the current first bin in the list NLIST is adjacent to the last bin added to the current bin group GROUP(m), by checking whether NEXTBIN= TEMPBIN+1 (step 318). If the value of NEXTBIN is not equal to TEMPBIN+1, this indicates that the bins are not adjacent bins and the procedure opens a new bin group by incrementing the value of the group counter m by 1 (step 320), resets the value of GROUPSIZE(m) to zero (step 321), stores the current value of NEXTBIN in TEMPBIN (step 322) and returns control to step 312 for generating the next bin group.

If NEXTBIN=TEMPBIN+1, this indicates that the bins are adjacent bins and the procedure stores the current value of NEXTBIN in TEMPBIN, adds the bin number NEXTBIN to the current bin group GROUP(m) and removes the bin number NEXTBIN from the list NLIST (step 324). The procedure then increments the value of the parameter GROUPSIZE(m) by 1 (step 326) and returns control to step 314.

In this way, the procedure generates one or more bin groups, each of these groups including contiguously adjacent bins, until the list NLIST is empty.

The group sorting procedure of step 330 is disclosed in detail hereinafter (and illustrated in FIG. 16 hereinbelow). Briefly, the total number of events in each bin group is determined and the groups are then sorted by descending total number of group events.

After sorting the bin groups for the current histogram, the procedure begins processing the bin group having the largest number of recorded events by setting a group index L to a value of L=1 (step 332). The group index L represents the position of the bin group within the sorted list NLIST. The procedure then checks whether GROUPSUM(L) ≧TOTBEATS, wherein GROUPSUM(L) is the sum of the number of events recorded in all the bins in bin group GROUP(L), and TOTBEATS is the expected cumulative number of detected events for the current data histogram HIST(EV,CL,SL,ETC) (step 334). If GROUPSUM(L) is smaller than TOTBEATS, the procedure gets the values of GROUPMIN and GROUPMAX for GROUP(L) (step 336). These values were found by the group sorting procedure (see FIG. 16) as is disclosed in detail hereinafter. The procedure then checks whether the current group spans the entire histogram length by checking whether GROUPMIN=1 and GROUPMAX=MAXBINS, wherein MAXBINS is the total number of bins in the histogram (step 338). If GROUPMIN=1 and GROUPMAX=MAXBINS, this means that the current group includes all the bins in the entire histogram. However, since in step 334 the procedure determined that the total number of events recorded in the bins of the current group is smaller than the expected total number of events for the entire histogram, a contradiction is indicated and the procedure evokes an error message "NOT OK" (step 340) and returns control to the main program (step 342).

If, in step 338 GROUPMIN is not equal to 1 or GROUPMAX is not equal to MAXBINS, the procedure transfers control to the group enlarging procedure for enlarging GROUP(L) (step 344) as is disclosed in detail hereinafter (see FIG. 18) and returns control to step 334.

Going back to step 334, if GROUPSUM(L) is equal to or larger than TOTBEATS, the procedure transfers control to the group shrinking procedure for shrinking GROUP(L) (step 346) as is disclosed in detail hereinafter (see FIG. 17). After control is returned by the group shrinking procedure, the procedure checks whether GROUPSIZE(L)>MAXWIN (EV,CL,ETC), wherein MAXWIN(EV,CL,ETC) is an array or a look-up table (LUT) including values representing the maximal window size (in bins) which is considered to be the maximal acceptable window size for a specific combination of values of the parameters CL, EV and ETC. Thus, for example, the value stored in the position MAXWIN(1, PACE,ON) of the array or LUT MAXWIN(EV,CL,ETC) represents the maximal acceptable window size for a paced beat having a cycle length falling in the first cycle length category and having a logical variable ETC=ON. In another example, the value stored in the position MAXWIN(3, SENSE, OFF) of the array or LUT MAXWIN(EV, CL, ETC) represents the maximal acceptable window size for a sensed beat having a cycle length falling within the third cycle length category and having a value of the logical variable ETC=OFF.

The values of stored in the array or LUT MAXWIN(EV, CL, ETC) are empirically found values which are typically preset before the data processing by the main program is begun. These values may be based, inter alia, on clinical results previously obtained in a plurality of patients and on considerations involving a compromise between alert window size and acceptable spurious noise levels.

It will be appreciated that some of the values stored in the array or LUT MAXWIN(EV,CL,ETC) may be identical. For example, in accordance with one preferred embodiment of the present invention, the values representing the maximal acceptable window size for a plurality of cycle length categories may be the same. Thus, the array or LUT MAXWIN(EV, CL, ETC) may be partially "degenerate". In accordance with another preferred embodiment of the present embodiment, the array or LUT MAXWIN(EV, CL, ETC) may completely degenerate, in which case it is replaced by a single constant MAXWIN representing a maximal window size acceptable under all cardiac conditions and the check performed in step 348 becomes a check whether GROUPSIZE(L)>MAXWIN (this step is not actually shown in FIG. 13B).

If GROUPSIZE(L)>MAXWIN(EV,CL,ETC), the procedure checks whether L=GROUPNUMBER (step 350). If L=GROUPNUMBER, this indicates that there are no more available bin groups left and that the available collected data does not allow assigning for the current histogram an alert window size which is equal to or smaller than the maximal acceptable window size and the procedure returns an error message "not OK" (step 340) and returns control to the main program (step 342)

If L is not equal to GROUPNUMBER, this indicates that there are bin groups left to be analyzed and the procedure increments the value of L by 1 (step 352) and returns control to step 334 for further processing of additional bin group data.

Going back to step 348, if GROUPSIZE(L) is equal to or smaller than the current value of MAXWIN(EV,CL,ETC), this indicates that the size of the current group is acceptable as the size of the alert window and the procedure stores the current values of GROUPMIN and GROUPMAX as the appropriate pair of values representing the starting (earliest) bin number and the ending (latest) bin number of the alert window, respectively, appropriate for the current histogram in the array WINDOW (EV,CL,ETC) (step 354), the procedure returns an "OK" message (step 356) and transfers control to the procedure or program from which it was invoked (step 342).

Figure 14:
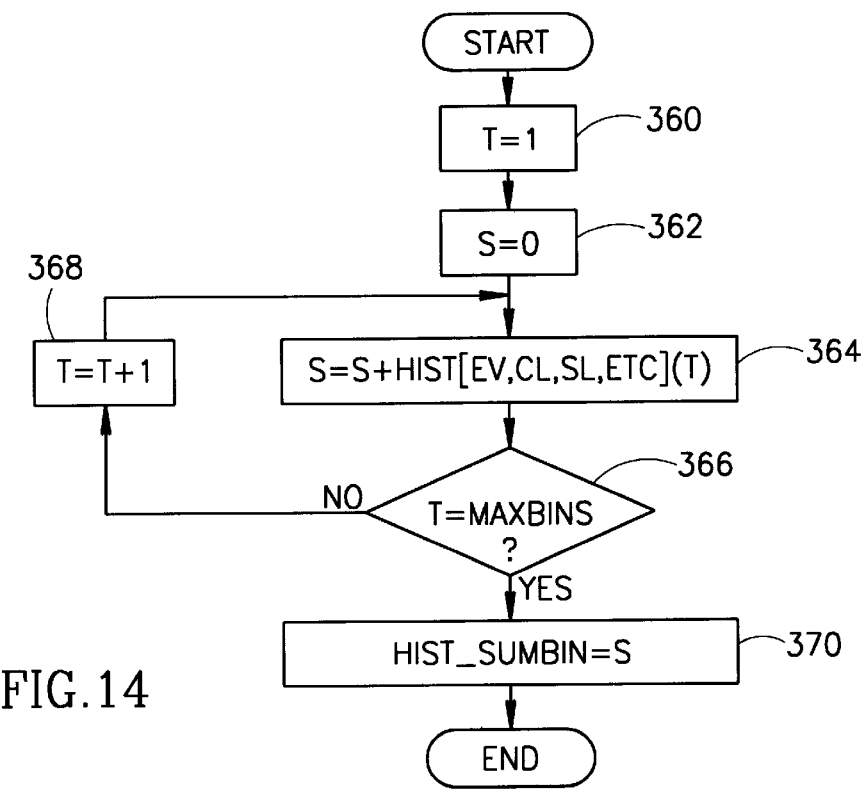
FIG. 14 is a schematic flow control diagram representing the steps of a procedure for determining the sum of the number of detected events stored in a given data histogram, in accordance with a preferred embodiment of the present invention.

Reference is now made to FIG. 14, which is a schematic flow diagram representing the steps of a procedure for determining the sum of the number of detected events stored in a given data histogram, in accordance with a preferred embodiment of the present invention.

The procedure starts by setting the value of an integer counter T to T=1 (step 360). The counter T represents the number of the current bin within the current data histogram HIST(EV, CL,SL,ETC). The procedure also sets the value of an integer bin counter S to S=0 (step 362). The procedure then increments the current value stored in the bin counter S by the number HIST(EV, CL,SL,ETC)(T) representing the number of detected events stored in bin T of the current data histogram HIST(EV, CL,SL,ETC) (step 364). The procedure then checks whether T=MAXBINS (step 366), wherein MAXBINS is the total number of bins in the current data histogram HIST(EV,CL,SL,ETC). If T is not equal to MAXBINS, the procedure increments the value of T by 1 (step 368) and transfers control to step 364. If T=MAXBINS, the procedure stores the current value of S as the value of HIST_SUMBIN (step 370) and returns control to the sensitivity level determining procedure of FIG. 12.

Figure 15:
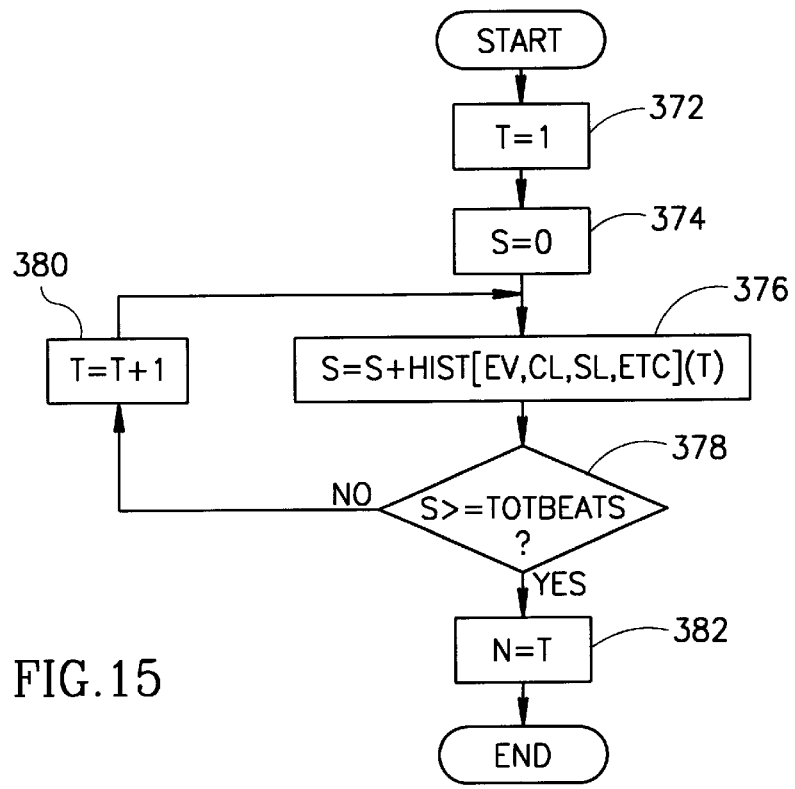
FIG. 15 is a schematic flow control diagram illustrating the steps of a procedure for determining the value of a variable N usable in the window position determining procedure of FIG. 13A–13C.

Reference is now made to FIG. 15 which is a schematic flow control diagram illustrating the steps of a procedure for determining the value of the variable N usable in the window position determining procedure of FIGS. 13A–13C, in accordance with a preferred embodiment of the present invention.

The procedure of FIG. 15 starts setting the value of an integer counter T to T=1 (step 372). The counter T represents the number of the current bin within the current data histogram HIST(EV, CL,SL,ETC). The procedure also sets the value of an integer bin counter S to S=0 (step 374). The procedure then increments the current value stored in the bin counter S by the number HIST(EV, CL,SL,ETC)(T) representing the number of detected events stored in bin T of the current data histogram HIST(EV, CL,SL,ETC) (step 376). The procedure then checks whether S≧TOTBEATS (Step 378). If S is not larger than or equal to TOTBEATS the procedure increments the value of T by 1 (step 380) and transfers control to step 376. If S is larger than or equal to TOTBEATS the procedure stores the current value of T as the value of N (step 382) and returns control to the window position determining procedure of FIGS. 13A–13C.

Figure 16:
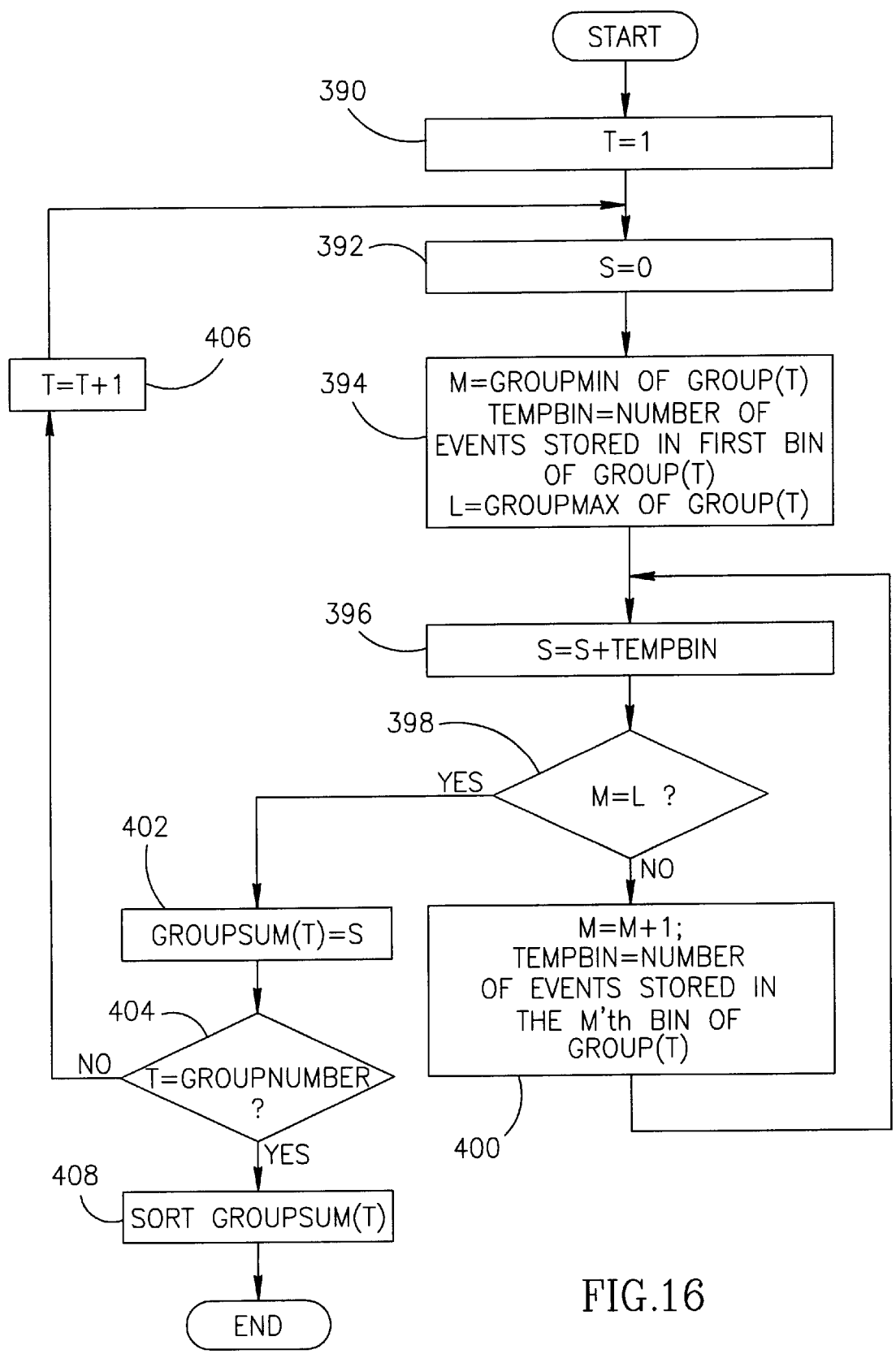
FIG. 16 is a schematic flow control diagram illustrating the steps of a group sorting procedure usable in the window position determining procedure of FIGS. 13A–13C, in accordance with a preferred embodiment of the present invention.

Reference is now made to FIG. 16 which is a schematic flow control diagram illustrating the steps of the group sorting procedure usable in the window position determining procedure of FIG. 13B, in accordance with a preferred embodiment of the present invention.

Briefly, the group sorting procedure sorts the groups obtained for the current data histogram by computing the total number of detected events stored in all the bins included within each of the groups of the current data histogram group GROUP(T), stores the obtained group event sums in an array GROUPSUM(T) and then sorts the groups by sorting the values within the array GROUPSUM (T) by descending order of total group event number.

The procedure sets the value the value of an integer group counter T to T=1 (step 390). The group counter T represents the number of the current bin group GROUP(T). The procedure also sets the value of an integer group event counter S to S=0 (step 392). The procedure stores in an integer variable M the value of the variable GROUPMIN representing the minimal bin number included in the current T'th group GROUP(T), stores in the pointer TEMPBIN the number of detected events which is stored in the first bin of the current bin group GROUP(T), and stores in an integer variable L the value of the variable GROUPMAX representing the maximal bin number included in the current T'th group GROUP(T) (step 394). The group sorting procedure then updates the value of the group event counter S by adding the current value of TEMPBIN to S (step 396). The procedure then checks whether M=L (step 398). If M is not equal to L, indicating that there are additional bins within the current group GROUP(T), the procedure increments the value of M by 1 and stores the number of events stored in the M'th bin of GROUP(T) in TEMPBIN (step 400), and transfers control to step 396.

If M is equal to L, indicating that there are no remaining bins within the current group GROUP(T), the procedure stores the current value of group event counter S in the variable GROUPSUM(T) representing the total sum of the events detected in all the bins included in the current group GROUP(T) (step 402). The procedure then checks whether T=GROUPNUMBER (step 404). If the group counter T is not equal to GROUPNUMBER, indicating that not all the groups for the current data histogram have been processed, the procedure increments the value of the group counter T by 1 (step 406) and transfers control to step 392 for further group processing. If T=GROUPNUMBER, indicating that all the groups obtained for the current data histogram have been processed, the procedure sorts the values stored in the array GROUPSUM(T), in descending order(step 408) and returns control to the window position determining procedure (of FIG. 13B).

Figure 17:
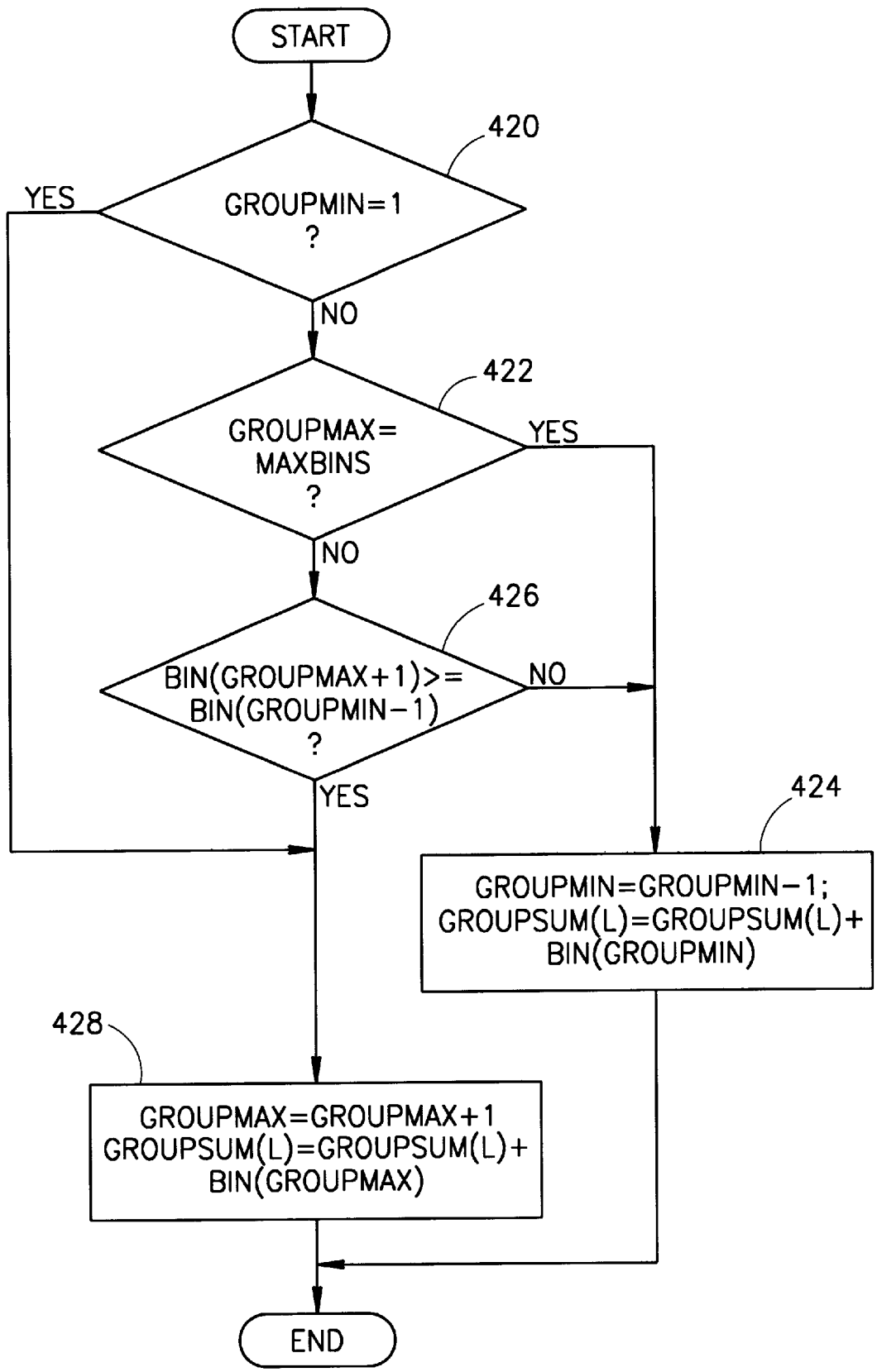
FIG. 17 is a schematic flow control diagram illustrating the steps of the group enlarging procedure usable in the window position determining procedure of FIGS. 13A–13C, in accordance with a preferred embodiment of the present invention.

Reference is now made to FIG. 17 which is a schematic flow control diagram illustrating the steps of the group enlarging procedure usable in the window position determining procedure of FIG. 13B, in accordance with a preferred embodiment of the present invention. As disclosed hereinabove (in step 334, 336 and 338 of FIG. 13B), the group enlarging procedure is used to enlarge a bin group in cases in which the current group includes less than TOTBEATS detected events. The current bin group is enlarged by consecutively adding bins to the group for increasing the total number of detected events included in the current bin group.

The group enlarging procedure of FIG. 17 starts by checking whether GROUPMIN=1 (step 420). If GROUPMIN=1, indicating that the first bin in the current group is identical to the first bin of the current data histogram, the procedure transfers control to step 428. If GROUPMIN is not equal to 1, indicating that the first bin in the current group is not identical to the first bin of the current data histogram, the procedure checks whether GROUPMAX=MAXBINS (step 422). If GROUPMAX= MAXBINS, the procedure decrements the value of GROUPMIN by 1 to add an additional bin to the group and updates the value of GROUPSUM(L) by adding to it the number of detected events BIN(GROUPMIN) stored in the bin which was added to the group (step 424). The procedure then returns control to the window position determining procedure of FIG. 13B.

If GROUPMAX is not equal to MAXBINS, the procedure checks whether BIN(GROUPMAX+1)≧BIN (GROUPMIN−1) (step 426), wherein BIN(GROUPMAX+ 1) represents the number of detected events stored in the bin of the current data histogram which is adjacent to the last bin of the current bin group and which is not included in the current bin group, and BIN(GROUPMAX−1) represents the number of detected events stored in the bin of the current data histogram which is adjacent to the first bin of the current bin group and which is not included in the current bin group. The check of step 426 is performed in order to determine on which side of the current group the next bin is to be added to the group based upon a comparison of the number of detected events stored in the two bins which are adjacent to the current first and last bins of the current group.

If BIN(GROUPMAX+1) is not equal to or larger than BIN(GROUPMIN−1), the procedure transfers control to step 424.

If BIN(GROUPMAX+1)≧BIN(GROUPMIN−1), the procedure increments the value of GROUPMAX by 1 to add an additional bin to the group and updates the value of GROUPSUM(L) by adding to it the number of detected events BIN(GROUPMAX) stored in the bin which was added to the group (step 428) and returns control to the window position determining procedure of FIG. 13B.

Figure 18:
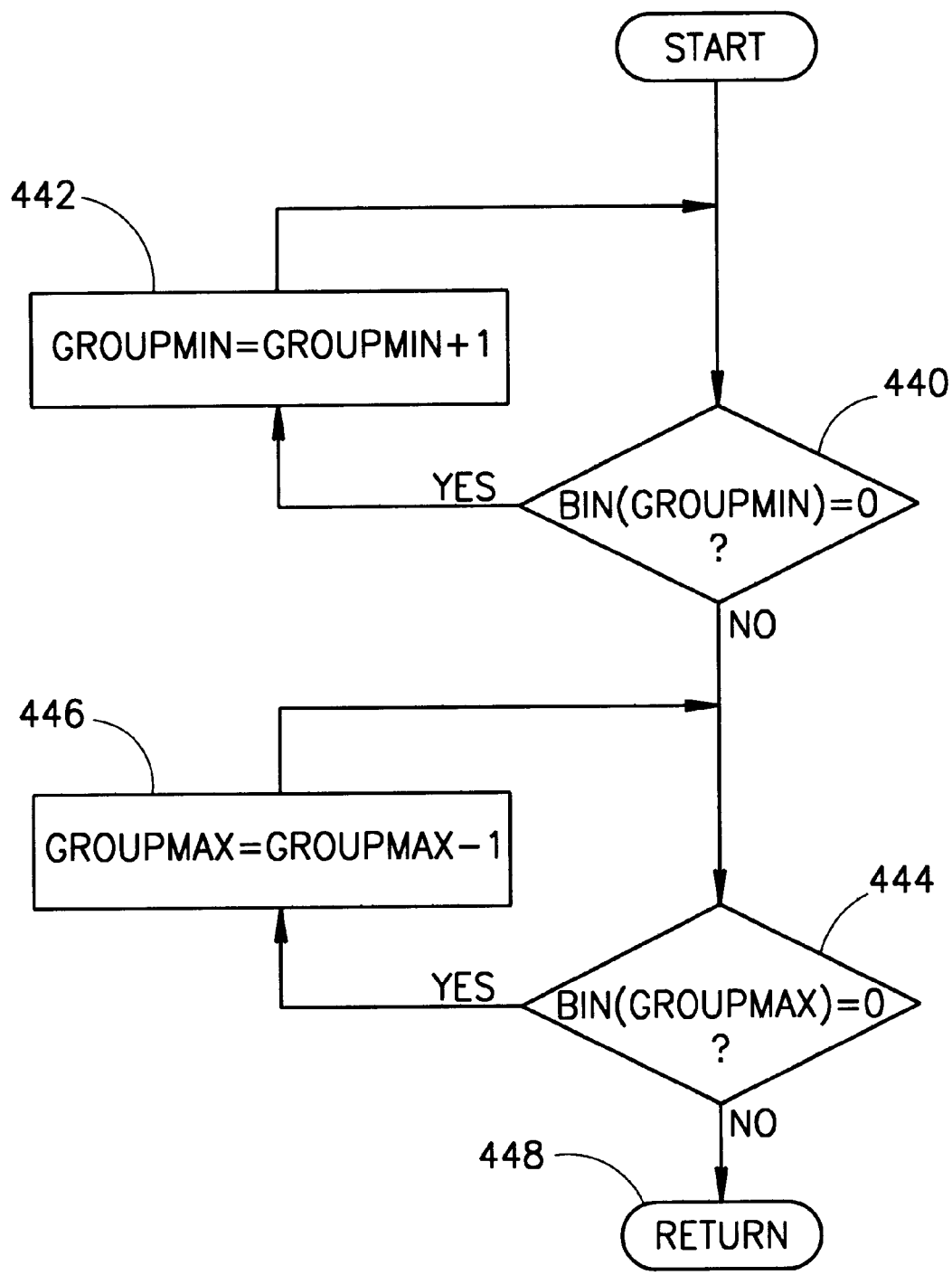
FIG. 18 is a schematic flow control diagram illustrating the steps of the group shrinking procedure usable in the window position determining procedure of FIG. 13B, in accordance with a preferred embodiment of the present invention.

Reference is now made to FIG. 18 which is a schematic flow control diagram illustrating the steps of the group shrinking procedure usable in the window position determining procedure of FIG. 13B, in accordance with a preferred embodiment of the present invention. The group shrinking procedure is invoked by step 334 of the window position determining procedure disclosed hereinabove (FIG. 13B) in cases in which the number of events in the current bin group is equal to or larger than TOTBEATS. The purpose of the group shrinking procedure is to remove from the current bin group bins in which the number of detected events is zero, the removal is performed starting from the bins positioned at the edges of the bin group and proceeds until a bin with a non-zero number of detected events is encountered.

The group shrinking procedure starts by checking whether the number of detected events BIN(GROUPMIN) which is stored in the current first bin of the current bin group is equal to zero (step 440). If BIN(GROUPMIN)=0, the procedure removes the "empty" bin from the group by incrementing the value of the first bin number GROUPMIN by 1 (step 442) and returns control to step 440 for checking the next bin. If BIN(GROUPMIN) is not equal to zero, the bin is not empty and the procedure transfers control to step 444 for checking the last bin of the group. In step 444 the procedure checks whether the number of detected events BIN (GROUPMAX) which is stored in the current last bin of the current bin group is equal to zero. If BIN(GROUPMAX)=0, the procedure removes the empty bin from the group by decrementing the value of the last bin number GROUPMAX by 1 (step 446) and returns control to step 444. If BIN (GROUPMAX) is not equal to zero, the last bin is not empty, the group cannot be further shrunk and the procedure returns control to the window position determining procedure of FIG. 13B (step 448).

Figure 19:
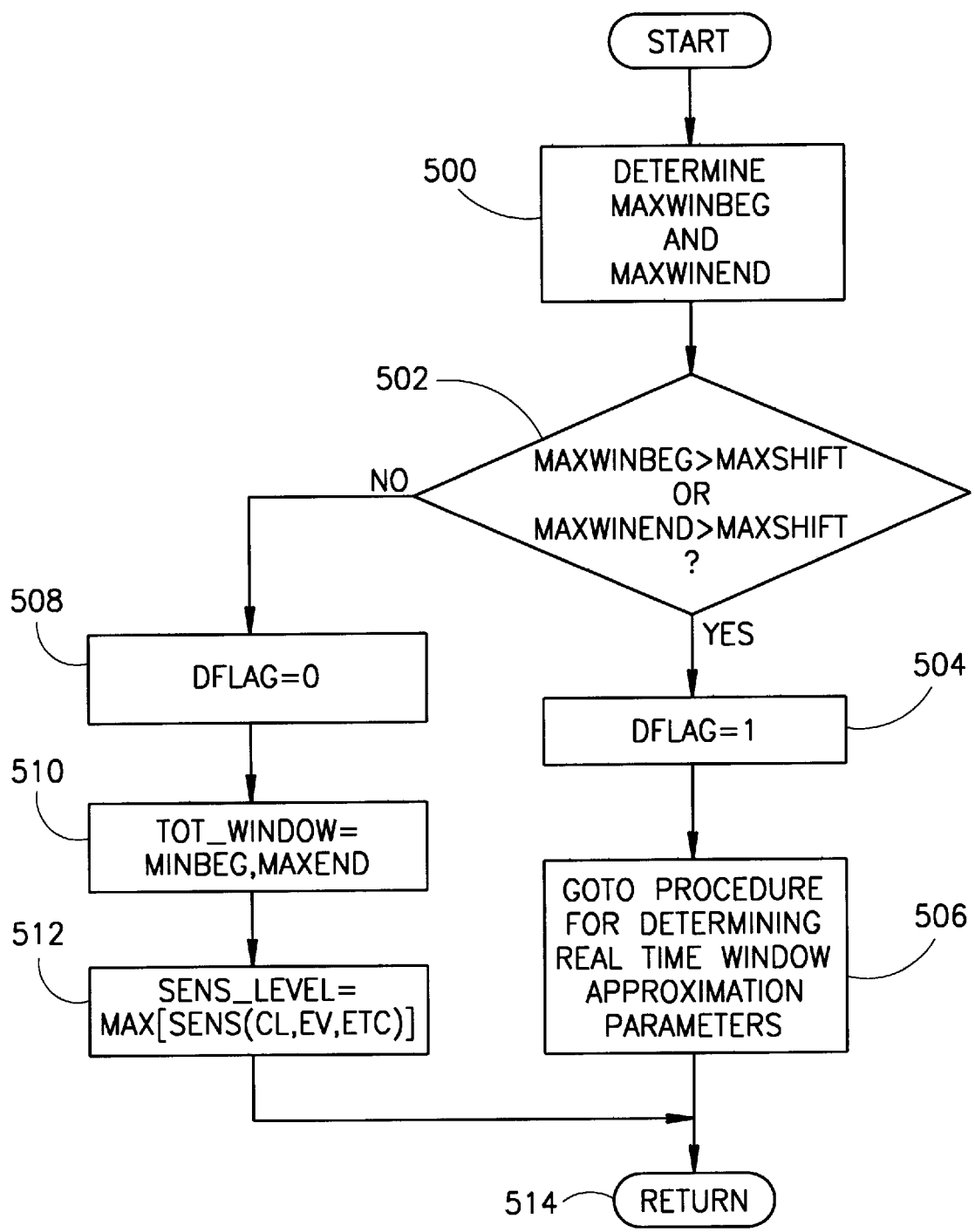
FIG. 19 is schematic flow control diagram illustrating the steps of the common window position parameters determining procedure usable in the main data analysis program of FIGS. 11A–11B, in accordance with a preferred embodiment of the present invention.

Reference is now made to FIG. 19 which is schematic flow control diagram illustrating the steps of the common window position parameters determining procedure usable in the main data analysis program of FIGS. 11A–11B, in accordance with a preferred embodiment of the present invention. The purpose of the procedure illustrated in FIG. 19 is to analyze the values of the first and last window bin numbers which were computed from all the data histograms as disclosed hereinabove and which are stored in the array WINDOW(EV,CL,ETC) and to determine therefrom a set of parameters which may be stored in the memory of the ETC and pacemaker/ETC devices of the present invention and used for real time determination of the alert window timing parameters. The parameters determined by the procedure of FIG. 19 may represent the starting bin number and the ending bin number of a single fixed alert window also referred to as "static alert window" which will be used for all beats irrespective of the beat cycle length. This single set of static alert window parameters will be used for sensed beats (naturally occuring beats) and for paced beats, in the presence and in the absence of the delivery of ETC signals. The details of the use of a static alert window are disclosed in detail in U.S. patent application to Mika et al., Ser. No. 09/276,460, Titled "APPARATUS AND METHOD FOR TIMING THE DELIVERY OF NON-EXCITATORY ETC SIGNALS TO A HEART".

In contrast to using a single set of alert window parameters, the starting time point and the duration of the alert window may be varied for beats having different cycle length (different R—R intervals). The method of adapting the parameters of the alert window (starting time point and ending time point) to the current cardiac conditions is referred to as the "dynamic alert window" method hereinafter.

The parameters determined by the procedure of FIG. 19 may be a set of approximation parameters which are used to compute in real time the alert window parameters. One simple way to determine the beginning and the ending time points for the alert window based on the current known value of the R—R interval and of the value of the current values of the variables EV and ETC, as determined in real time, is to determine into which cycle length category CL the current R—R interval falls and to use the determined value of the alert window parameters (the starting and ending bin numbers) which are stored in the array WINDOW(EV,CL, ETC) to compute the starting and ending time points of the alert window based on the known bin duration. The advantage of such a method is that it is simple to implement. The computing of such an approximation may be advantageous due to the fact that the data recorded in a data histogram was actually derived from a plurality of beats having various different cycle lengths. Thus, while the data within a data histogram is used for computing an "average" common set of alert window parameters from all the beat cycles having a duration falling within the duration limits of a particular arbitrarily chosen cycle length category, the use of such a common set of alert window parameters for real time determining of the alert window delay and duration for all the beats falling within the cycle length category may result in non-optimal placement of the alert window, particularly for those beats having a cycle length value which is close to the "ends" of the cycle length category values (these ends are the shortest and longest beat cycle duration values which are still included within a particular cycle length category). This non-optimal alert window placement may be tolerated in cases in which a relatively large number of cycle length categories is used for data acquisition. However, in some preferred embodiments of the present invention it may be impractical or undesirable to use a large number of cycle length categories due to data capacity limitations of the memory of an implanted ETC or ETC/pacemaker device, or due to the need to acquire a larger number of cardiac beats in order to have enough data acquired for each of the cycle length category leading to an increase in the overall time period required for patient data acquisition. Therefore, in accordance with another preferred embodiment of the present invention, the alert window parameters stored in the array WINDOW(EV,CL,ETC) may be further processed to provide a set of approximation parameters which may be stored in the ETC or pacemaker/ETC device and used to compute in real time improved approximated values of the beginning time point and the ending time point based on the current value of the R—R interval. The advantage of this approximation method is that it provides improved on-line computed approximations of the alert window beginning and ending time points while not overly increasing the necessary number of cycle length categories used for data acquisition, which may also be advantageous in shortening the time period required for collecting the histogram data sets from the patient.

The common window position parameters determining procedure of FIG. 19 starts by determining the values of the variables MAXWINBEG and MAXWINEND (step 500). As disclosed hereinabove, the array WINDOW (EV,CL, ETC) stores a plurality of pairs of bin numbers. The first number within each pair of bin numbers represents the number of the first bin (the bin at the window's beginning of the alert window determined for a particular combination of the variables EV,CL,ETC as disclosed in detail hereinabove), and the second number within each pair of bin numbers represents the number of the last bin (the bin at the window's end) of the same alert window. MAXWINBEG is the difference between the highest first bin number and the lowest first bin number of all the first bin numbers of all of the pairs of bin numbers stored in the array WINDOW (EV,CL,ETC). MAXWINBEG Therefore represents the maximal difference (in bins) between all the alert window beginning points included in the array the WINDOW (EV, CL,ETC).

MAXWINEND is the difference between the highest second bin number and the lowest second bin number of all the second bin numbers of all of the pairs of bin numbers stored in the array WINDOW (EV,CL,ETC). MAXWINEND Therefore represents the maximal difference (in bins) between all the alert window ending points included in the array the WINDOW (EV,CL,ETC).

Determining the values of MAXWINBEG and MAXWINEND may be performed in various ways. For example, in accordance with one non-limiting example, this may be performed by sorting the window beginnings (the first bin numbers of all the bin number pairs) by ascending bin number, then taking the difference between the last and the first bin numbers of the sorted list to obtain MAXWINBEG. Similarly, sorting the window endings (the second bin numbers of all the bin number pairs) by ascending bin number, then taking the difference between the last and first bin numbers of the sorted list to obtain MAXWINEND.

Alternatively, in accordance with another non-limiting example, one may define a minimum beginning variable and a maximum beginning variable, both equal to the first (beginning) bin number of the first pair of bin numbers in WINDOW(CL,EV,ETC), and then running through all the other bin number pairs, updating the value of the minimum beginning variable and the maximum beginning variable numbers if needed until all the bin number pairs in the array WINDOW(CL,EV,ETC) are exhausted. The difference between the maximum beginning variable value and the minimum beginning variable value then gives the value of MAXWINBEG. The value of MAXWINEND is computed by defining a minimum ending variable and a maximum ending variable both equal to the second (ending) bin number of the first pair of bin numbers in WINDOW(CL, EV,ETC), and then running through all the other bin number pairs, updating the value of the minimum ending variable and the maximum ending variable numbers if needed until all the bin number pairs in the array WINDOW(CL,EV, ETC) are exhausted. The difference between the maximum ending variable value and the minimum ending variable value then gives the value of MAXWINEND.

It is noted that the values of MAXWINBEG and MAXWINEND may also be determined by any other suitable method or algorithm known in the art. After determining the values of MAXWINBEG and MAXWINEND, The procedure continues by comparing the values of MAXWINBEG and MAXWINEND to the value of a user determined constant MAXSHIFT which represents the maximal allowable value (in bins) of MAXWINBEG and MAXWINEND (step 502). If MAXWINBEG>MAXSHIFT or MAXWINEND>MAXSHIFT indicating the the maximal allowable value has been exceeded, the procedure sets the value of the flag DFLAG to 1 (step 504), transfers control to a procedure for determining real-time window approximation parameters (step 506) and returns control to the main data analysis program (FIG. 11B). If MAXWINBEG is not larger than MAXSHIFT and MAXWINEND is not larger than MAXSHIFT, the procedure, the procedure sets the value of the flag DFLAG to zero (step 508), stores the value of MINBEG and MAXEND as the first bin number and the last bin number of TOT_WINDOW_(step 510), wherein TOT_WINDOW is an array holding two window parameters representing the overall (unified) alert window, MINBEG represents the lowest value of the first (beginning) bin number of all the pairs of bin numbers stored in the array WINDOW(CL,EV, ETC), and MAXEND represent the highest value of the second (ending) bin number of all the pairs of bin numbers stored in the array WINDOW(CL,EV, ETC).

The procedure then sets an overall sensitivity level SENS_LEVEL for use in conjunction with the window parameters stored in TOT_WINDOW, by selecting the value of the highest sensitivity level determined MAX [SENS(CL,EV,ETC)] for any of the analyzed data as the value of SENS_LEVEL (step 512). For example, this may be accomplished by sorting by ascending or descending order all the sensitivity levels SENSE(EV,CL,ETC) determined by the sensitivity level determining procedure of FIG. 12 procedure during the performance of the main data analysis program of FIGS. 11A and 11B, and by setting the last value or the first value, respectively, in the sorted list of sensitivity level values as the value of SENS_LEVEL. After setting the value of SENS_LEVEL, the procedure returns control to the main data analysis program of FIG. 11B (step 514).

The value of SENS_LEVEL and the array TOT_WINDOW are_later telemetrically or non-telemetrically programmed into the memory unit (not shown) of the implantable ETC device 19 of FIG. 3A or into the memory unit 44 of the devices 21 or 24 (of FIGS. 3A and 4, respectively) and is used in the operation of the devices 19, 21 and 24 for setting the beginning and ending points of the alert window and the detection sensitivity level, respectively, of the devices 19 or 21 or 24 in real-time as disclosed in detail hereinafter.

It is noted that, the value of MAXSHIFT is entered as input by the user (typically the cardiologist performing the data analysis) during the analysis, and may be based on the user's judgment of the duration of allowable common (unified) alert window which will result in the a alert window which is large enough to include most of the events which need to be detected while still being positioned such as not to result in unacceptable levels of detection of spurious events due to electrical noise (synchronous or non-synchronous with the heart beat), PVCs, and the like. The user's decision about the appropriate value of MAXSHIFT may be assisted by visually observing the temporal distribution of detected events within the various data histograms which the user may display on the display unit 32 of the analyzing unit 23 of the system 20 (FIG. 3A) or of the system 60 (FIG. 5) and the system 70 (FIG. 6). The entry of the value of MAXSHIFT may be performed through a suitable user interface such as, but not limited to, one or more of the user interface(s) 31 of FIG. 3A, or one or more of the user interface device(s) 69 of FIGS. 5 and 6.

Figure 20:
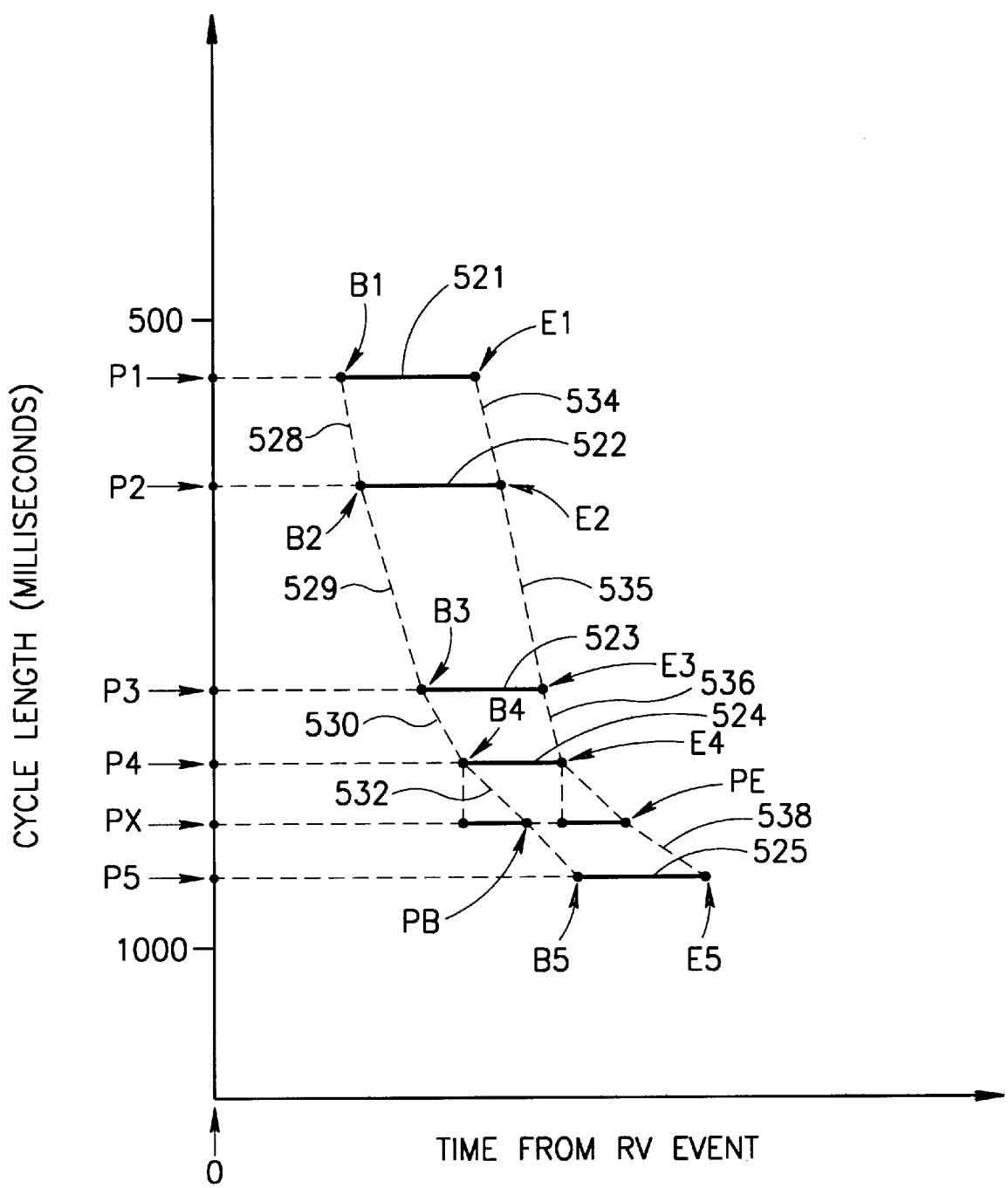
FIG. 20 is a schematic graph useful for understanding a method for computing a set of approximation parameters useful for the real time computing of the alert window parameters, in accordance with a preferred embodiment of the present invention.

Reference is now made to FIG. 20 which is a schematic graph useful for understanding a method for computing a set of approximation parameters for the real time computing of the alert window parameters, in accordance with a preferred embodiment of the present invention. The vertical axis represents the cycle length in arbitrary units and the horizontal axis represents the time measured from the detection of an RV event (the zero time point of the horizontal axis represents the time of detection of an RV event. This zero time point of the horizontal axis coincides with the time of detection of the RV event 11 of FIG. 2. The horizontal lines labeled 521, 522, 523, 524 and 525 schematically represent five alert windows which were determined by the window position determining procedure of FIGS. 13A–13C for the first five contiguous cycle length categories selected out of the twelve cycle length categories of the non-limiting example disclosed hereinabove. It is noted that, for the sake of clarity of illustration, only these five selected alert windows are shown in the graph of FIG. 20 and the remaining other seven alert windows are not shown. It is also noted that, for the sake of clarity of illustration, the starting and ending points of the five alert windows represented by the horizontal lines 521, 522, 523, 524 and 525 are given in arbitrary time units from the time of detection of the RV event 11 and not in bin numbers (as they are stored in the array WINDOW(CL,EV,ETC) disclosed hereinabove). Thus, for example, the alert window represented by the line 523 begins at the time represented by the projection of the beginning point B3 of the line 523 on the horizontal time axis and ends at the time represented by the projection of the ending point E3 of the line 523 on the horizontal time axis. Similarly, the alert windows represented by the lines 521, 522, 524 and 525 have beginning points B1, B2, B4 and B5 and ending points E1, E2, E4 and E5, respectively.

The points P1, P2, P3, P4 and P5 represent the mid points of the cycle length categories used to determine the alert windows represented by the lines 521, 522, 523, 524 and 525, respectively. For example, the midpoint of a cycle length category (not shown in FIG. 20) including beat cycles from 550 to 650 millisecond long will be at 600 milliseconds on the vertical axis (point not shown). It is noted that, the graph of FIG. 20 is given by way of a schematic explanatory example only and does not represent actual experimentally derived values.

In accordance with one preferred embodiment of the present invention, the real time determination of the alert window for each beat cycle uses a piecewise linear approximation method. In the graph of FIG. 20 all the beginning points and ending points of all the determined alert windows (of which only the alert windows represented by the lines 521, 522, 523, 524 and 525 are illustrated) are connected by lines. For example, the beginning points B1 and B2 are connected by the dashed line 528, the beginning points B2 and B3 are connected by the dashed line 529 the beginning points B3 and B4 are connected by the dashed line 530, the beginning points B4 and B5 are connected by the dashed line 532. Similarly, the ending points E1 and E2 are connected by the dashed line 534, the ending points E2 and E3 are connected by the dashed line 535, the ending points E3 and E4 are connected by the dashed line 536, the ending points E4 and E5 are connected by the dashed line 538. The slope of each of the lines 528, 529, 530, 532, 534, 535, 536 and 538 may be computed from the known values of the beginning points B1, B2, B3, B4 and B5, and the ending points E1, E2, E3, E4 and E5. When it is desired to compute the approximated beginning point PB and the approximated ending point PE of an alert window for a detected event having a measured interval value represented by the point PX which lies on the vertical cycle length axis between the cycle length category midpoints P4 and P5, the piecewise linear approximation is used by computing these values from equations 1 and 2:

$$PB = B4 + (PX - P4)^*(SLOPE-532) \quad (1)$$

$$PE = E4 + (PX - P4)^*(SLOPE-538) \quad (2)$$

wherein (SLOPE-532) is the computed value of the slope of the line 532 and (SLOPE-538) is the computed value of the slope of the line 538. It is noted that the slopes of the lines 532 and 538 may or may not be identical and their values depend on the particular values of the points B4 and E4, and B5 and E5 of the computed alert windows represented by the lines 524 and 525, respectively. Similarly, The values of the slopes of the lines 528 and 534, 529 and 535, and 530 and 524 depend on the particular determined values of the beginning and ending points of the corresponding computed alert windows represented by the lines 521, 522, 523, 524 and 525.

Preferably, as disclosed for the R—R interval represented by the point PX, the procedure for linear piecewise approximation uses the beginning and ending points of the line representing the alert window having an associated midpoint which has an equal or lower value than the value of the R—R interval and the slopes of the lines connecting the beginning and ending points of this line with the beginning and ending points of the line representing the alert window directly below it in the graph. However, if the R—R interval has a value smaller than the value of the point P1 on the vertical axis, the computation procedure uses the slopes of the lines 528 and 534. If the value of the R—R interval is equal to or larger than the value of the midpoint (not shown in FIG. 20) of the last cycle length category, the procedure uses for the computation the beginning and ending points of the last alert window (not shown in FIG. 20) and the slopes of the lines connecting the beginning point and ending point of the last alert window with the corresponding beginning point and ending point of the alert window (not shown) which lies above the last alert window in the graph of FIG. 20

It is noted that while the cycle length categories who's midpoints P1, P2, P3, P4 and P5 are shown in FIG. 20 do not span identical time ranges, other embodiments of the present invention may be implemented in which some or all of the cycle length categories span identical time ranges.

It is further noted that, for the non-limiting particular example used in describing the invention, for each acquired data set which is analyzed one may generate four different graphs, corresponding to the four possible combinations of the two variables EV and ETC. These combinations are EV=SENSE, ETC=OFF; EV=SENSE, ETC=ON; EV=PACE, ETC=OFF; and EV=PACE, ETC=ON. Each of these four graphs (not shown) includes twelve alert windows determined for the corresponding twelve cycle length categories of the non-limiting example of the invention disclosed hereinabove. Therefore, if one uses the non-limiting example using 12 cycle length categories disclosed hereinabove, the set of approximation parameters which is determined includes for each of the four possible combinations of EV and ETC 22 slope values, 12 beginning points and 12 ending points. Thus, the full set of approximation parameters includes 88 slope values, 48 beginning points and 48 ending points. However, if another number of cycle length categories is used in data acquisition, the number of approximation parameters will vary accordingly.

The full set of the approximation parameters is telemetrically or non-telemetrically programmed into the memory unit (not shown) of the implantable ETC device 19 of FIG. 3A or into the memory unit 44 of the devices 21 or 24 (FIGS. 3A and 4, respectively) and is used in the operation of the devices 19, 21 and 24 for real-time computing of the approximation of the alert window beginning and ending time points for the various cycle lengths of detected beats under paced and sensed beat conditions in the absence and presence of the delivery of ETC signals.

Figure 21:
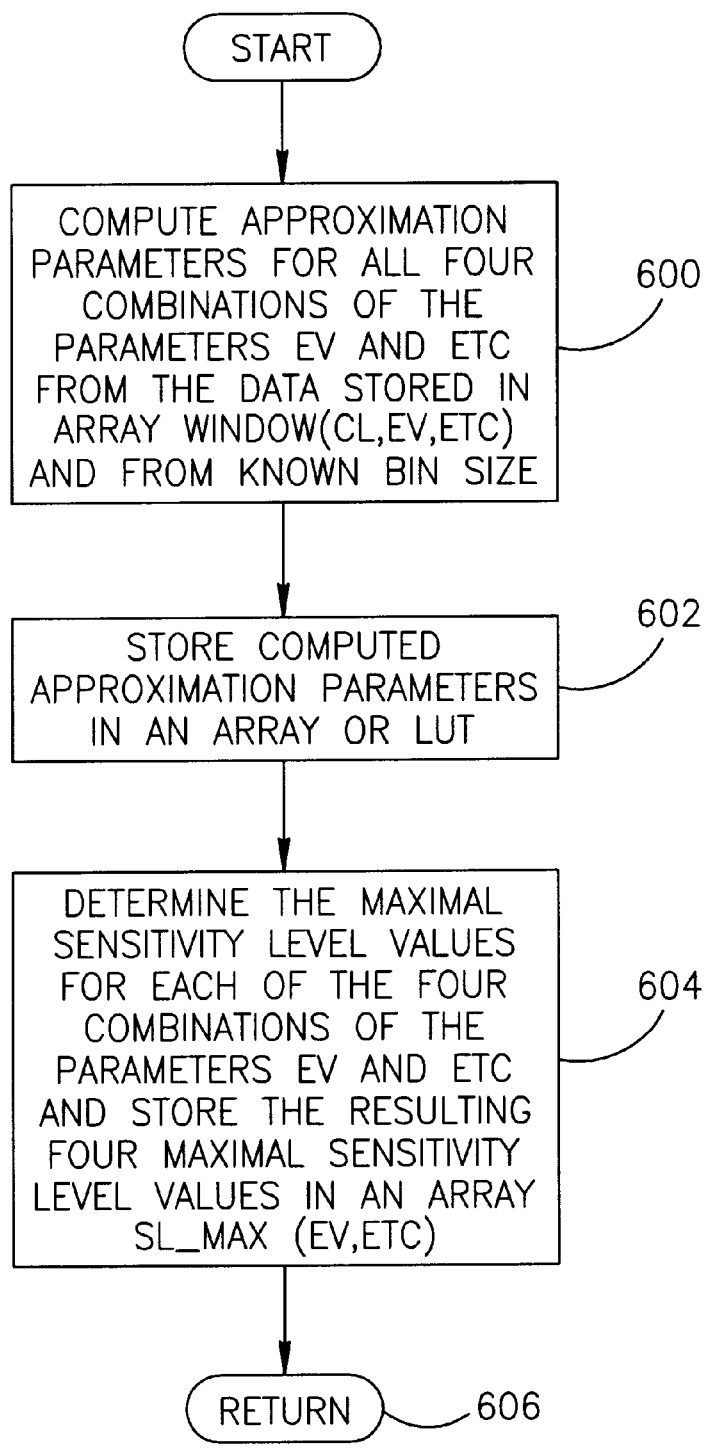
FIG. 21 is a schematic flow control diagram illustrating the steps of an exemplary procedure for determining the real time window approximation parameters of FIG. 19, in accordance with one preferred embodiment of the present invention.

Reference is now made to FIG. 21 which is a schematic flow control diagram illustrating the steps of an exemplary procedure for determining the real time window approximation parameters of FIG. 19, in accordance with one preferred embodiment of the present invention. The procedure starts by computing the approximation parameters for all the possible combinations of the parameters EV and ETC from the data stored in the array WINDOW(CL,EV,ETC) and from the known bin size (step 600). The possible combinations are EV=SENSE and ETC=OFF; EV=SENSE and ETC=ON; EV=PACE and ETC=OFF; EV=PACE and ETC=ON. The approximation parameters include the beginning time points and ending time points for each of the alert windows determined for each cycle length category in each of the above possible parameter combinations. The approximation parameters also include the slopes of each of the lines connecting the beginning points (as disclosed hereinabove and illustrated in FIG. 20) and the slopes of each of the lines connecting the ending points (as disclosed hereinabove and illustrated in FIG. 20) for each of the above possible parameter combinations. The procedure then stores the full set of the approximation parameters in an array or LUT (step 602).

The procedure then determines the maximal sensitivity level values for each of the four combinations of the parameters EV and ETC and stores the resulting four maximal sensitivity level values in an array SL_MAX (EV,ETC) (step 604). The determination of the values of the maximal sensitivity depends on the specific detection method which is used for detecting the LV events and may be performed in any suitable method known in the art. For example, in the above disclosed case where a single positive threshold crossing method is used, one possible way to determines the maximal sensitivity level values is to sort each of the four groups SENS(SENSE,CL,OFF), SENS(SENSE,CL,ON), SENS(PACE,CL,OFF) and SENS(PACE,CL,ON) of sensitivity level values stored in the array SENS(EV, CL,ETC)

(see FIG. 12) in ascending order and storing the last value in each of the sorted groups in the appropriate positions in the array SL_MAX (EV,ETC). The sensitivity level value group SENS(SENSE,CL,OFF) includes the sensitivity levels determined for all the data histograms acquired for the parameter combination EV=SENSE and ETC=OFF (no pacing and no ETC signal delivery). The sensitivity level value group SENS(SENSE,CL,ON) includes the sensitivity levels determined for all the data histograms acquired for the parameter combination EV=SENSE and ETC=ON (no pacing and with ETC signal delivery). The sensitivity level value group SENS(PACE,CL,OFF) includes the sensitivity levels determined for all the data histograms acquired for the parameter combination EV=PACE and ETC=OFF (with pacing and no ETC signal delivery). The sensitivity level value group SENS(PACE,CL,ON) includes the sensitivity levels determined for all the data histograms acquired for the parameter combination EV=PACE and ETC=ON (with pacing and with ETC signal delivery).

In the non-limiting example disclosed hereinabove each of the groups to be sorted SENS(SENSE,CL,OFF), SENS(SENSE,CL,ON), SENS(PACE,CL,OFF) and SENS(PACE,CL,ON) includes 12 values of determined sensitivity levels. It will be appreciated by those skilled in the art that many other ways of determining the maximal sensitivity levels may be used, depending on the type of event detection method which is used. Thus, the method of determining the maximal sensitivity levels for each of the above four groups SENS(SENSE,CL,OFF), SENS(SENSE,CL,ON), SENS(PACE,CL,OFF) and SENS(PACE,CL,ON), may be adapted to the type of event detection method which is used. The array SL_MAX (EV,ETC) is also telemetrically or non-telemetrically programmed into the memory unit (not shown) of the implantable ETC device 19 of FIG. 3A or into the memory unit 44 of the devices 21 or 24 (FIGS. 3A and 4, respectively) and is used in the operation of the devices 19, 21 and 24 for real-time setting of the detection sensitivity level of the devices 19, 21 and 24 as is disclosed in detail hereinafter.

Finally, the procedure returns control to the common window position parameters determining procedure of FIG. 19 (step 606).

The approximation parameter array or LUT, is used for programming of the implantable ETC device 19 of FIG. 3A or the devices 21 or 24 (FIGS. 3A and 4, respectively) as disclosed hereinabove. After programming, the approximation parameters are used for real-time determination of the approximated alert window beginning and ending points as disclosed in detail hereinabove and illustrated in FIG. 20. For instance, in the case of the non-limiting example disclosed hereinabove which includes 12 cycle length categories in each of the four possible combinations of the parameters EV and ETC, the stored array or LUT includes 88 slope values, 48 beginning points and 48 ending points.

Figure 22:
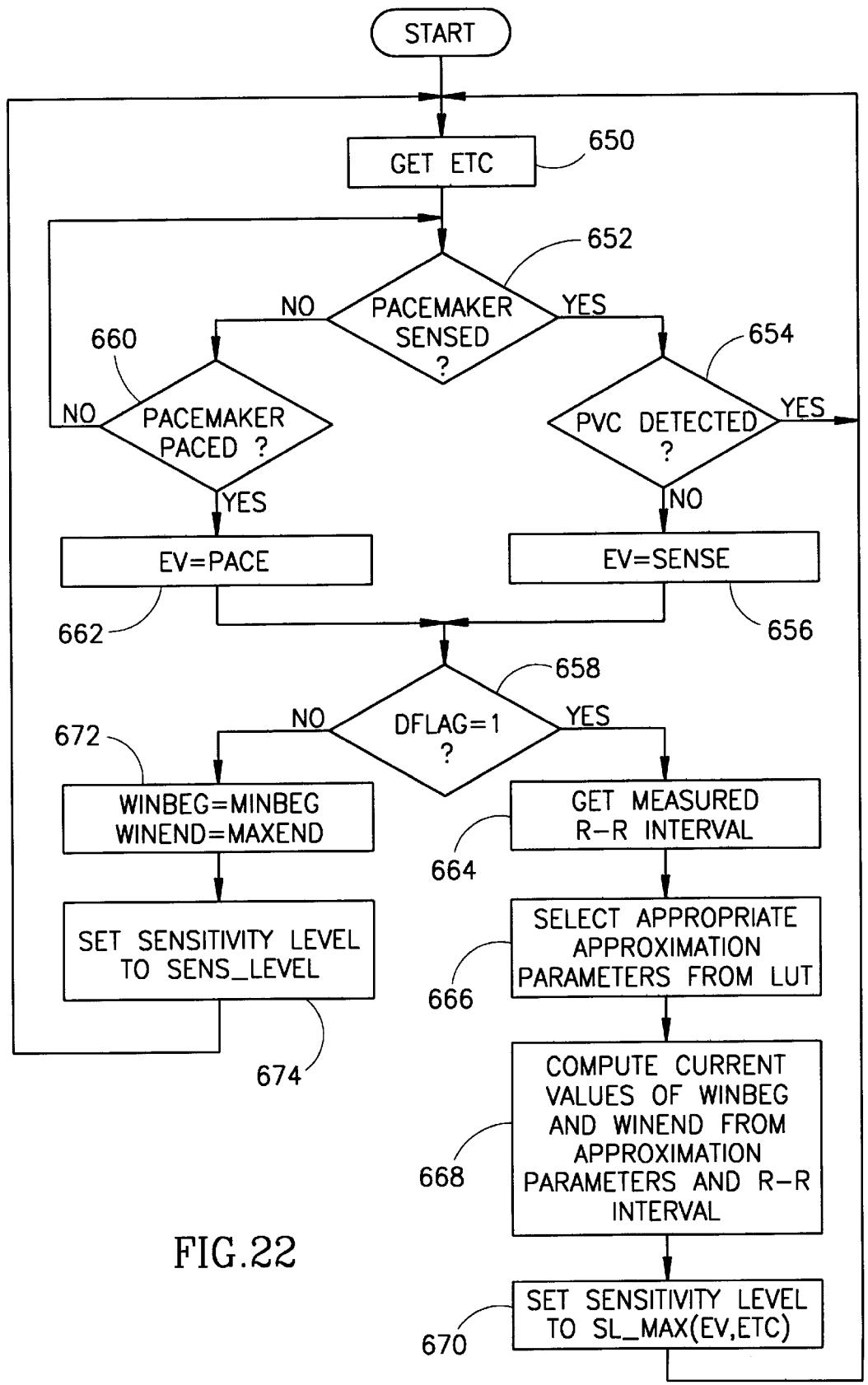
FIG. 22 is a schematic control flow diagram illustrating the steps of a method for real time setting of the beginning and ending time points of an alert window and of the detection parameters in an ETC device having pacing capabilities, in accordance with a preferred embodiment of the present invention.

Reference is now made to FIG. 22 which is a schematic control flow diagram illustrating the steps of a method for real time setting of the beginning and ending time points of an alert window and of the detection parameters in an ETC device having pacing capabilities, in accordance with a preferred embodiment of the present invention. The program implementing the method of FIG. 22 is operative in the devices 19, 21 and 24 after they have been programmed with the appropriate data. The data includes the value of the flag DFLAG, the array or LUT of approximation parameters as disclosed hereinabove and the array of maximal sensitivity level values SL_MAX (EV,ETC) The program starts by getting the current value of the parameter ETC (step 650).

During the real-time operation of the program, the current value of the parameter ETC is continuously updated in real-time by the procedure disclosed hereinabove and illustrated in FIG. 10. The program then checks if the pacemaker circuitry sensed an event (step 652). If the pacemaker sensed an event, the program checks if a PVC was detected (step 654). If a PVC was detected, the program does not allow the delivery of an ETC signal for the current beat and returns control to step 650. If a PVC was not detected, the program updates the value of the parameter EV by setting it's value to EV=SENSE (step 656), and checks the value of the flag DFLAG (step 658).

If in step 652, the pacemaker has not sensed, the program checks if the pacemaker has paced (step 660). If the pacemaker paced, the program updates the value of the parameter EV by setting it's value to EV=PACE (step 662), and transfers control to step 658 for checking the value of the flag DFLAG. If the pacemaker did not pace control is returned to step 652.

In step 658 If DFLAG=1, the program gets the current measured value of the R—R interval from the pacemaker circuitry (step 664), selects the appropriate approximation parameters for the current R—R interval by finding the value of the cycle length category CL within which the current value of the R—R interval falls (the detailed steps of finding the value of the cycle length category CL are not shown herein as they are well known in the art) and using the current values of the cardiac condition defining variables ETC, EV and CL for the selection of the appropriate approximation parameters from the LUT or array (step 666) and computes the current values of the alert window parameters WINBEG representing the approximated beginning time of the alert window and WINEND representing the approximated ending time of the alert window by using the equations 1 and 2 as disclosed in detail hereinabove and illustrated in FIG. 20 (step 668).

For example, if the R—R interval is equivalent to the value represented by the point PX of FIG. 20, step 666 selects the value of the beginning point B4 (FIG. 20), the ending point E4 (FIG. 20) and the slopes of the lines 532 and 538 (FIG. 20) and in step 668 computes PB and PE from equations 1 and 2, respectively, and set WINBEG=PB and WINEND=PE.

The program then sets the current sensitivity level to be used by the detection circuitry by using the sensitivity level stored in the array SL_MAX(EV,ETC) in the array position defined by the current values of the parameters EV and ETC (step 670) and returns control to step 650.

If in step 658 the value of the flag DFLAG is not equal to 1, this indicates that a single pair of values for the alert window beginning time point and ending time points and a single common sensitivity value were selected as adequate for use with all R—R intervals measured in real-time irrespective of the cycle length category into which the measured R—R interval fits (as disclosed in detail in steps 502, 508, 510 and 512 of FIG. 19). The program then updates the values of the parameters WINBEG and WINEND by using the two values MINBEG and MAXEND stored in the array TOT_WINDOW (see FIG. 19) such that WINBEG=MINBEG and WINEND=MAXEND (step 672), sets the sensitivity level to the value stored in SENS_LEVEL (step 674) and returns control to step 650.

It will be appreciated by those skilled in the art that the preferred embodiment of the program for real-time setting of the alert window parameters and the detection sensitivity level disclosed hereinabove and illustrated in FIG. 22, is given by way of example only and that many variations and modifications thereof are possible which are included within the scope of the present invention. For example, while the steps 666 and 668 of the method of FIG. 22 select the proper linear piecewise approximation parameters and computes the values of the alert widow beginning and ending time points WINBEG and WINEND from the selected linear piecewise approximation parameters and the measured R—R interval, other methods (not shown) for computing WINBEG and WINEND may also be used based on other approximation methods known in the art such as, but not limited to, spline approximation methods or the like. Additionally, in accordance with another preferred embodiment of the present invention, the steps the steps 666 and 668 of FIG. 22 may be replaced by steps(not shown) which do not perform an approximation computation but instead compute the beginning point and ending point of the alert window directly from the beginning bin number and the ending bin number of the array WINDOW(EV,CL,ETC) and from the known bin size (the bin duration). In this preferred embodiment, the data in the LUT which is stored in the device includes the array WINDOW(EV,CL,ETC), the array SL_MAX(EV,ETC), the value of the flag DFLAG and the bin size (in time units). As disclosed hereinabove, the latter embodiment may be used in cases where the data acquisition was performed using a large number of cycle length categories which may obviate the need for performing the approximation.

It is noted that, while the above disclosed methods and procedures are adapted for devices which include pacing circuitry, Such as the implantable device 21 of FIG. 3A, the analyzing unit 64 of the system 60 of FIG. 5 and the like, the methods of the present invention may also be adapted with some modifications for use with devices having no cardiac pacing capability, such as the device 24 of FIG. 4, the analyzing unit 74 of the system 70 of FIG. 6, and the like.

Figure 23A:
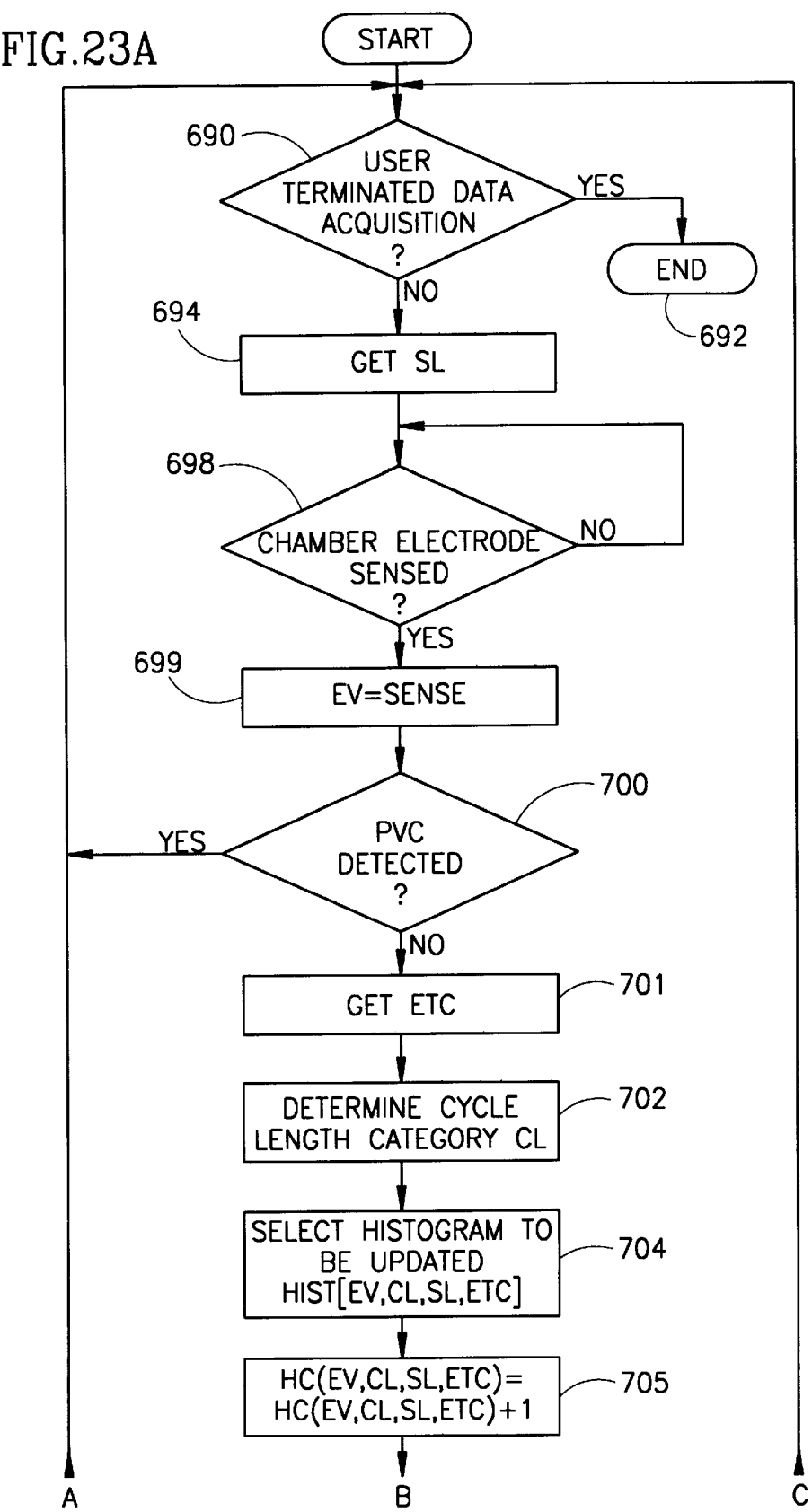
FIGS. 23A–23B are schematic flow control diagrams illustrating the steps of a method for acquiring time histogram data sets under various cardiac conditions in the absence of artificial cardiac pacing and for determining one or more sets of alert window parameters or approximation parameters and one or more detection parameter sets from the histogram data, in accordance with a preferred embodiment of the present invention.
Figure 23B:
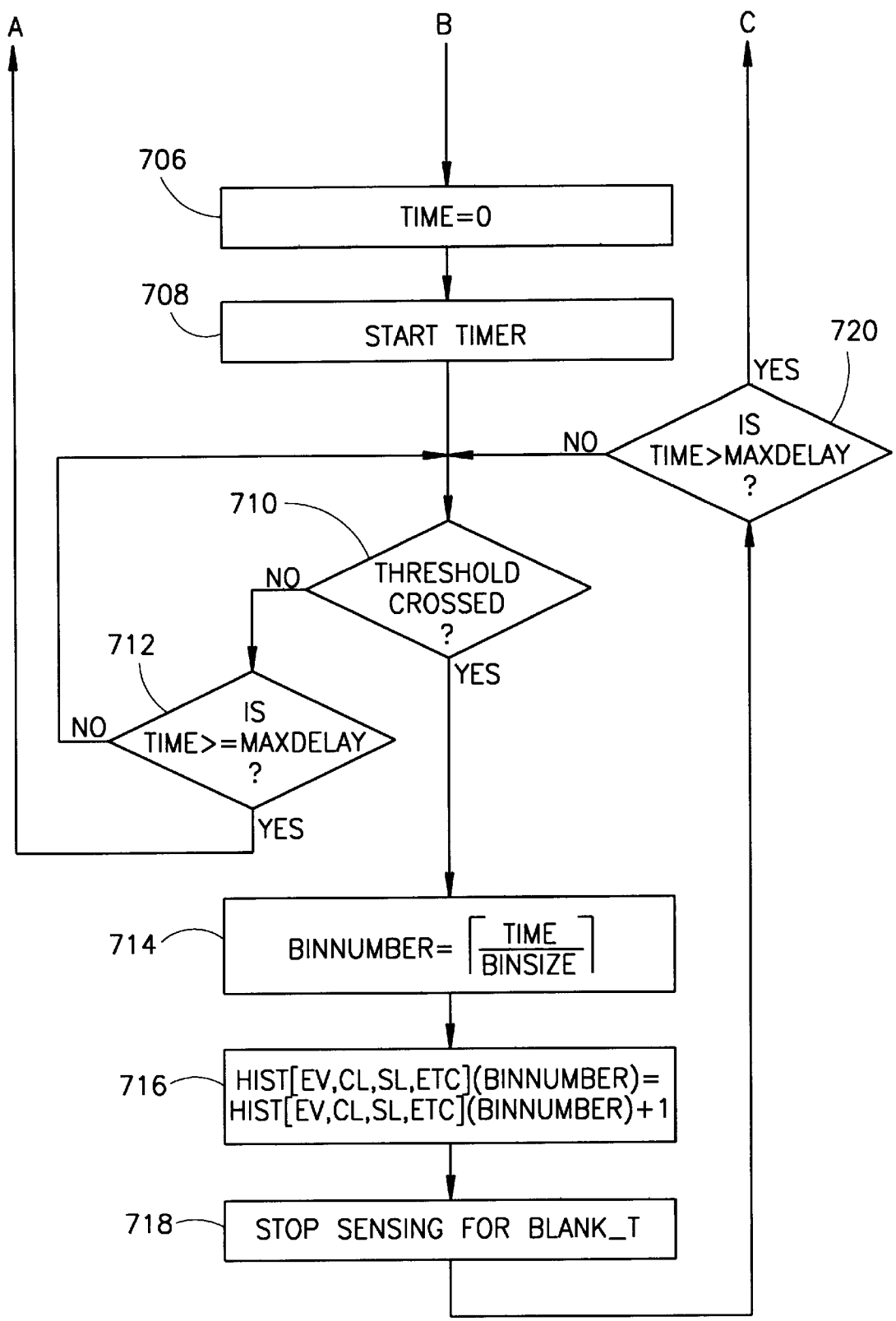

Reference is now made to FIGS. 23A–23B which are schematic flow control diagrams illustrating the steps of a method for acquiring time histogram data sets under various cardiac conditions in the absence of artificial cardiac pacing and for determining one or more sets of alert window parameters or approximation parameters and one or more detection parameter sets from the histogram data, in accordance with a preferred embodiment of the present invention.

The method illustrated in FIGS. 23A–23B is a modified version of the more general method disclosed hereinabove and illustrated in FIGS. 8B–8C. The difference between the two procedures is that in the method of FIGS. 23A–23B there is no pacing during the data acquisition time period.

The data collection program embedded within the pacemaker/ETC device 24 of FIG. 4 or the analyzing unit 74 of FIG. 6 starts by checking whether the user or operator has terminated the collection of data (step 690). The user (typically the cardiologist) may terminate data collection by a suitable command which is transmitted telemetrically to the pacemaker/ETC device 24, or input manually to the analyzing unit 74 of the system 70 through one of the user interface device(s) 69. Typically, the command may set a suitable flag or change the value of a variable which is checked by the program. However, other suitable methods for terminating data collection may be used. If the user did terminate data collection the data collection program ends (step 692). If the user did not terminate data collection, the program gets the current sensitivity level value SL (step 694). The sensitivity level variable SL may be an integer variable which can take any integer value selected from a group of integer numbers, each representing a particular sensitivity value available for use in the pacemaker/ETC device 24 or the analyzing unit 74. For example, if the event detection sensitivity is determined by the crossing of a single voltage threshold and the pacemaker/ETC device can have 8 different sensitivity levels, SL may be any integer in the range 1–8.

The data collection program checks whether the device 24 (or the 74) sensed an event in the RV chamber (step 696). This is performed by the appropriate sensing unit of the sensing units 38 which is operatively associated with the sensing electrode (not shown) of the implantable leads 22 which is positioned in the RV. If the device sensed an RV event, the data collection program sets the value of the logical parameter to EV=SENSE to indicate a sensed beat cycle (step 699) and checks whether a premature ventricular contraction (PVC) was detected (step 700). The detection of a PVC is performed by the ETC device 24 or by the pacing program operating the processing unit 61 of the analyzing unit 74.

It is noted that, while the device 24 and the analyzing unit 74 do not include pacing circuitry for pacing the heart, they do contain suitable circuitry (not shown in detail) which is capable of detecting PVCs. A PVC may be detected using the signals sensed in the RV. As is known in the art, PVC's may be identified by detecting two consecutive ventricular events without an atrial event therebetween. For example, the PVC detection methods used in pacemakers operating in a DDD mode are suitable for use in the data collection method of the present invention.

However, other methods suitable for PVC detection may be used. PVC detection methods are well known in the art, are not the subject matter of the present invention and will therefore not be discussed in detail hereinafter.

If a PVC was detected the data collection program returns control to step 690 for avoiding collection of data for the current beat cycle. If a PVC was not detected, the data collection program gets the value of the variable ETC (step 701). The variable ETC is a logical variable which can have the values "ON" and "OFF". When ETC=OFF the histogram represents data considered to be collected under conditions in which there was no practically substantial influence of the delivery of ETC signals on the cardiac conduction velocity. When ETC=ON the histogram represents data considered to be collected under conditions in which the delivery of ETC signals has substantial influence of on the cardiac conduction velocity. The detailed procedure of setting the value of the variable ETC and the criteria used to set the value of the variable ETC are disclosed in detail hereinabove and illustrated in FIG. 10. The remaining steps of the data acquisition program of FIGS. 23A–23B are similar to the equivalent steps of the data acquisition program of FIGS. 8B–8C. Steps 701, 702, 704, 705, 706, 708, 710, 712, 714, 716, 718 and 720 of FIGS. 23A–23B are similar to steps 101, 102, 104, 105, 106, 108, 110, 112, 114, 116, 118 and 120, respectively, of FIGS. 8B–8C, except that the data histograms HIST(EV, CL,SL,ETC) of the steps of FIGS. 23A–23B represent a degenerate set of the data histograms HIST(EV,CL,SL,ETC) of FIGS. 8B–8C since the value of the parameter EV, as set by step 699 of the method of FIG. 23A, can only be EV=SENSE because the device 24 and the analyzing unit 74 have no pacing capability. Thus, the total number of the data histograms acquired by the data acquisition method of FIGS. 23A–23B is half of the total number of the data histograms acquired by the data acquisition method of FIGS. 8B–8C.

It is noted that in step 712 of FIG. 23B, if TIME>MAXDELAY, control is returned to step 690. In step 720 of FIG. 23B, if TIME>MAXDELAY, control is returned to step 690.

It is further noted that, when the data acquisition is performed by the device 24 of FIG. 4 or by the analyzing unit 74 of FIG. 6, using the data acquisition program illustrated in FIGS. 23A–23B, the program for determining the parameters of the alert window in real-time must also be modified since no pacing is performed by the device 24 or the analyzing unit 74.

Figure 24:
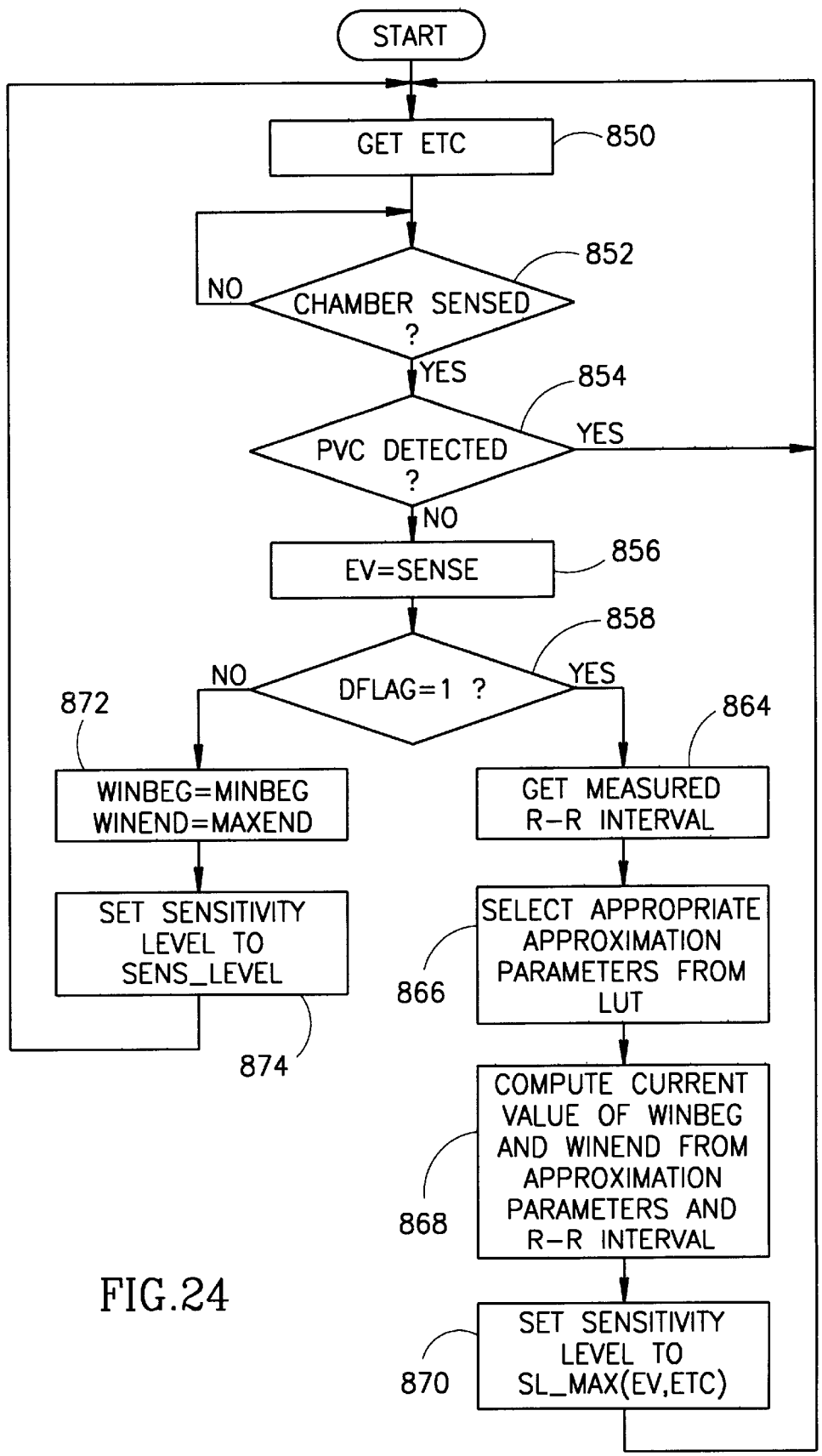
FIG. 24 is a schematic control flow diagram illustrating the steps of a method for real time setting of the beginning and ending time points of an alert window and of the detection parameters in a non-pacing ETC device, in accordance with another preferred embodiment of the present invention.

Reference is now made to FIG. 24 which is a schematic control flow diagram illustrating the steps of a method for real time setting of the beginning and ending time points of an alert window and of the detection parameters in a non-pacing ETC device, in accordance with another preferred embodiment of the present invention.

The program implementing the method of FIG. 24 is operative in the device 24 of FIG. 3A or in the analyzing unit 74 of the system 70 of FIG. 6 after they have been programmed with the appropriate data. The data includes the value of the flag DFLAG, the array or LUT of approximation parameters as disclosed hereinabove and the array of maximal sensitivity level values SL_MAX (EV,ETC).

It is noted that while the device 24 and the analyzing unit 74 do not have pacing capability, they include all the necessary circuitry and embedded programs for sensing and detecting events in one or more cardiac chambers as is known in the art and they are capable of determining and storing the R—R interval of the current beat as is known in the art. If the device 24 is used, the current value of the R—R interval is stored in the memory unit 44. If the analyzing unit 74 is used, the current value of the R—R interval is stored in the memory unit 66.

The program starts by getting the current value of the parameter ETC (step 850). During the real-time operation of the program, the current value of the parameter ETC is continuously updated in real-time by the procedure disclosed hereinabove and illustrated in FIG. 10. The program then checks if the detection circuitry sensed an event in the right ventricle chamber (step 852). When the program is embedded in the device 24 of FIG. 4, the sensing is performed by the appropriate sensing unit of the sensing units 38 which is associated with the sensing electrode positioned in the right ventricle such as the electrode or electrode pair 4A (FIG. 1). When the program is embedded in the analyzing unit 74 of FIG. 6, the sensing is performed by the circuitry of the front end 62 which is associated with the sensing electrode positioned in the right ventricle such as the electrode or electrode pair 4A (FIG. 1). If an event was sensed in the right ventricle chamber, the program checks if a PVC was detected (step 854). If a PVC was detected, the program does not allow the delivery of an ETC signal for the current beat and returns control to step 850. If a PVC was not detected, the program updates the value of the parameter EV by setting it's value to EV=SENSE (step 856), and checks the value of the flag DFLAG (step 858).

In step 858 If DFLAG=1, the program gets the current measured value of the R—R interval from the memory unit 44 of the device 24 or from the memory unit 66 of the analyzing unit 74 (step 864), selects the appropriate approximation parameters for the current R—R interval as disclosed in detail hereinabove (step 866) for FIG. 22 and computes the current values of the alert window parameters WINBEG representing the approximated beginning time of the alert window and WINEND representing the approximated ending time of the alert window by using the equations 1 and 2 as disclosed in detail hereinabove and illustrated in FIG. 20 (step 868).

The program then sets the current sensitivity level to be used by the detection circuitry by using the sensitivity level stored in the array SL_MAX(EV,ETC) in the array position defined by the current value of the parameter ETC (step 870) and returns control to step 650. It is noted that the array SL_MAX(EV,ETC) as determined by the data acquisition program of FIGS. 23A–23B is a degenerate form of the array SL_MAX(EV,ETC) determined by the data acquisition program of FIGS. 8B–8C since the parameter EV can have only the value EV=SENSE, therefore the degenerate array SL_MAX(EV,ETC) includes only two valid sensitivity levels for the cases in which ETC=ON and ETC=OFF.

If in step 858 the value of the flag DFLAG is not equal to 1, this indicates that a single pair of values for the alert window beginning time point and ending time points and a single common sensitivity value were selected as adequate for use with all R—R intervals measured in real-time irrespective of the cycle length category into which the measured R—R interval fits (as disclosed in detail in steps 502, 508, 510 and 512 of FIG. 19). The program then updates the values of the parameters WINBEG and WINEND by using the two values MINBEG and MAXEND stored in the array TOT_WINDOW (see FIG. 19) such that WINBEG=MINBEG and WINEND=MAXEND (step 872), sets the sensitivity level to the value stored in SENS_LEVEL (step 874) and returns control to step 850.

It is noted that, the program of FIG. 24 may be modified to use various different approximation methods such as a spline approximation method or other suitable approximation methods for computing the approximated alert window beginning and ending time points, as disclosed for the program of FIG. 22 hereinabove. Additionally, in accordance with another preferred embodiment of the present invention, the steps the steps 866 and 868 of FIG. 24 may be replaced by steps (not shown) which do not perform an approximation computation but instead compute the beginning point and ending point of the alert window directly from the beginning bin number and the ending bin number of the array WINDOW(EV,CL,ETC) and from the known bin size (the bin duration). In this preferred embodiment, the data in the LUT which is stored in the device includes the array WINDOW(EV,CL,ETC), the array SL_MAX(EV,ETC), the value of the flag DFLAG and the bin size (in time units). As disclosed hereinabove, this embodiment may be used in cases where the data acquisition was performed by the program of FIGS. 8B–8C using a large number of cycle length categories which may obviate the need for performing the approximation.

It is further noted that all the methods and procedures disclosed hereinabove are adapted for use with devices having detection circuitry which is capable of fast switching of the detection sensitivity in real-time. This means that at least one of the sensing units 38 of the devices 21 and 24 is capable of controllably switching from one sensitivity level to another sensitivity level within a time period which is short enough to implement sensitivity level changes from one heart beat to the next heart beat. Similarly, the front end 62 of the analyzing units 64 and 74 will also be capable of controllable fast switching between different sensitivity levels. For example, the sensitivity level may be controllably switched by controllably changing the threshold level of a comparator circuit (not shown). However, other suitable methods may be used for sensitivity changing. The design and implementation of such fast circuits for changing detection sensitivity levels is well known in the art, is not the subject matter of the present invention and is therefore not disclosed in detail herein. Moreover, even if the circuitry of a device used for patient data collection is not fast enough to affect a sensitivity level change on a beat by beat basis, the full set of histogram data may still be collected by acquiring data at a first sensitivity level from a first group of beats, changing the sensitivity level, acquiring data from a second group of beats and so forth until enough data has been acquired for all sensitivity levels.

It is still further noted that, while in the programs disclosed hereinabove and illustrated in FIGS. 22 and 24 the various determined approximation parameters are stored in an LUT or array, the various determined sensitivity levels are stored in an array SL_MAX(EV,ETC) and/or a variable SENS_LEVEL, and DFLAG may be stored in the LUT or separately, the way of storing the approximation parameters, the sensitivity levels and the value of DFLAG is not critical to the invention and many different ways of organizing and storing this information may be implemented as is well known in the art.

It is yet further noted that, while the present invention is disclosed as adapted for use in the ETC devices and in ETC/pacemaker devices disclosed hereinabove, the methods of the present invention may also be adapted for use in devices having additional capabilities. For example, in accordance with another preferred embodiment of the present invention, devices may be implemented which include in addition to the pacing capabilities and the ETC signal delivering capabilities, the capability to deliver defibrilation pulses to the heart as is well known in the art.

Furthermore, while the programs and procedures disclosed hereinabove are adapted for use with an exemplary embodiment of the present invention which uses the R—R interval computed from events sensed in or about the right ventricle, other preferred embodiments of the present invention may be adapted for using an A—A interval which is the computed time interval between consecutive detected atrial events which are locally sensed in or about the right atrium. The electrode configurations for such a preferred embodiment are disclosed in detail in the above referenced co-pending U.S. patent application to Mika et al., Ser. No. 09/276,460.

Further yet, for each beat cycle, after the beginning and ending time points of the dynamic alert window and the detection sensitivity level have been determined as disclosed hereinabove, if an ETC non-excitatory signal is delivered to the heart, the delivery may be performed as disclosed in detail hereinabove (FIG. 2) or as disclosed in the above referenced U.S. patent application Ser. No. 09/276,460. Thus, various preferred embodiments of the present invention make use of the delay period $\Delta T4$ of FIG. 2 and may or may not make use of the refractory period $\Delta T1$, the inhibition window $\Delta TI$, and the alert refractory period $\Delta T7$ of FIG. 2. Some modifications of the method illustrated in FIG. 2 may need to be implemented. For example, since the starting and ending points of the alert window of the present invention are dynamically set for each beat, the inhibition window $\Delta TI$ may be dynamically set for each beat based on the time $T_0$ of detection of the RV event (or alternatively the RA event if detection in the right atrium is used) of the current cardiac beat and on the value of the starting time point $T_1$ of the alert window $\Delta T3$ dynamically computed for the current cardiac beat. Another modification that may be implemented is that the duration of the alert refractory period $\Delta T7$ may be set such that the inequality $\Delta T7 > \Delta T3 + \Delta T4 + \Delta T5_{MAX}$ disclosed hereinabove holds for all possible values of $\Delta T3$. This means that the duration of $\Delta T7$ is set using the highest possible duration of the alert window which may be set under any of the various cardiac conditions (including the use of the approximation method disclosed hereinabove if applied). Thus, the value of $\Delta T7$ may be set to satisfy the above inequality based on the maximal duration of the alert window time period computable from the LUT or array holding the alert window parameters as determined from the data collected in the data collection session disclosed hereinabove.

In accordance with still another preferred embodiment of the present invention, the ETC device and the ETC/pacemaker device may also have fencing capabilities as disclosed in detail in PCT Application, International Publication Number WO 98/10830, titled "FENCING OF CARDIAC MUSCLES" to Ben Haim et al.

It is noted that throughout the present application the term "real-time" is used broadly to imply on-line performance of determinations, computations and approximations which are performed on the fly by the devices of the present invention for each cardiac beat cycle.

It is further noted that in the preferred embodiments of the invention disclosed hereinabove and illustrated in FIGS. 22 and 24 the value of the R—R interval which is used for determining the alert window beginning and ending time points is the currently measured "instantaneous" time interval between the detection of an RV event in the previous heart beat and the detection of an RV event in the current heart beat. However, due to the natural fluctuation of the R—R intervals it may be desired to use an average R—R interval for the real time computation of the alert window beginning and ending time points. Thus, in accordance with another preferred embodiment of the present invention, the procedures of FIGS. 22 and 24 may compute the current value of an average R—R interval (the detailed steps of such a computation of an average interval are well known in the art and are therefore not shown in FIGS. 22 and 24) and use it for the real-time computation of the alert window beginning and ending time points. For example, the programs of FIGS. 22 and 24 may store the R—R-intervals of the last K consecutive heart beats in a the memory 44 or 66 and compute the average R—R interval by summing these K R—R intervals and dividing the sum by K for each heart beat. In the next heart beat, the value of the currently measured R—R interval is added to the beginning of the list of K values, the earliest of the stored R—R interval values is removed from the list and the average is computed again. This may be implemented using a first in first out (FIFO) buffer or by any other suitable method for computing a dynamic average known in the art. When such an averaged R—R interval is used for computing the alert window beginning and ending time points, the number of stored R—R interval values K is preferably a small number in the range of 2–5 to reduce the possible effect of masking or attenuating abrupt changes in the R—R interval due to the averaging.

Since spurious detection in the RV of signals which are not true RV events may introduce an error in the calculation of such an average R—R interval, it may be desired to use the median of the R—R interval values instead of using their mean. In such preferred embodiments which use a computed median, the median value may preferably be computed from a number of stored R—R interval in the range of approximately 5–8 R—R intervals to reduce errors due to PVCs and the like.

It is noted that, throughout the application, the parameters ETC,EV, and CL, are also commonly referred to as the cardiac condition defining parameters. However, the variables ETC, EV and CL used in FIGS. 22 and 24 are generally referred to as the cardiac condition defining variables as they are updated on-line on a beat by beat basis. Thus, in FIGS. 22 and 24, the current values of the cardiac condition defining variables are used to select the appropriate set of approximation parameters having a matching set of associated values of cardiac condition defining parameters.

It is further noted that all the devices illustrated in FIGS. 1, 3A, 3B, 4, 5 and 6 include one or more power sources (not shown for the sake of clarity of illustration). The power source(s) of the implantable devices such as the device 1 of FIG. 1 and the device 19 of FIG. 3A, the device 21 of FIG. 3B and the device 24 of FIG. 4 may be any suitable electrical battery known in the art. In the devices which are not implanted within the body of the patients such as the analyzing units 64 and 74 of FIGS. 5 and 6, respectively, the power source may be any suitable power source known in the art such as a mains operated DC power supply, a battery or any other suitable source of electrical power known in the art. Such power sources are well known in the art, are not the subject matter of the present invention, and are therefore not described in detail hereinabove.

While the invention has been described with respect to a limited number of embodiments, many variations, modifications and other applications of the invention may be made which will be apparent to those skilled in the art. The present invention is thus not to be construed as limited by the modes of operation of the embodiments particularly described but may be practiced according to its concept, spirit and scope, as may be more readily understood by consideration of the appended claims.

What is claimed is:

1. A method for setting the parameters of an alert time window in an excitable tissue control device operative under a plurality of different cardiac conditions of a heart of a patient, the method comprising the steps of:

providing said excitable tissue control device with a set of data, said set of data comprises a plurality of sets of alert time window parameters, each set of alert time window parameters of said plurality of sets of alert time window parameters is associated with one of said plurality of different cardiac conditions, each set of alert time window parameters of said plurality of sets of alert time window parameters comprises at least a set of timing parameters usable for obtaining a beginning time point and an ending time point for said alert time window, each set of alert time window parameters of said plurality of sets of alert time window parameters is obtained by processing data collected from a plurality of cardiac beats of said heart of said patient under said plurality of different cardiac conditions within a data collection session prior to said step of providing;

automatically selecting, for a current beat cycle of said heart, a current set of alert time window parameters of said plurality of sets of alert time window parameters based on the current cardiac conditions detected for said current beat cycle;

using, for said current beat cycle, said current set of alert time window parameters selected in said step of automatically selecting to start and terminate said alert time window based on the time of detecting a first depolarization event at or about a first cardiac site;

detecting within the duration of said alert time window of said current beat cycle a second depolarization event at a second cardiac site of said heart; and triggering the delivery of a delayed non-excitatory excitable tissue control signal at or about said second cardiac site based on the time of detection of said second depolarization event.

2. The method according to claim 1 wherein each set of alert time window parameters of said plurality of sets of alert time window parameters further comprises at least one detection sensitivity parameter having a value representing a detection sensitivity level, and wherein said step of using further includes using said value of said detection sensitivity parameter to set the detection sensitivity level used within the duration of said alert time window of said current beat cycle.

3. The method according to claim 2 wherein said at least one detection sensitivity parameter comprises a voltage threshold level.

4. The method according to claim 2 wherein said at least one detection sensitivity parameter comprises at least one morphological detection parameter.

5. The method according to claim 2 wherein said set of data is a degenerate set of data in which at least some of said sets of alert time window parameters of said plurality of sets of alert time window parameters have identical values of said at least one detection sensitivity parameter.

6. The method according to claim 1 wherein said plurality of cardiac conditions comprises beats having a plurality of different beat to beat time intervals representing different instantaneous heart rates of said heart.

7. The method according to claim 1 wherein said plurality of cardiac conditions further comprises beats initiated by the natural pacemaker of said heart and beats initiated by a pacing pulse delivered by said excitable tissue control device.

8. The method according to claim 1 wherein said plurality of cardiac conditions comprises beats occurring during a time period in which the prior application of excitable tissue control signals results in a change of the velocity of propagation of a depolarization wave in at least a portion of the myocardial tissue disposed between said first cardiac site and said second cardiac site of said heart, and beats occurring during a time period in which the prior application of excitable tissue control signals does not result in a change in the velocity of propagation of a depolarization wave in a portion of the myocardial tissue disposed between said first cardiac site and said second cardiac site of said heart.

9. The method according to claim 1 wherein said set of timing parameters of said alert time window parameters comprises a beginning time point value and an ending time point value for said alert time window.

10. The method according to claim 1 wherein said excitable tissue control device is provided with a value of the bin duration of a time bin used for collecting data within said data collection session, said set of timing parameters of said alert time window parameters comprises a starting bin number and an ending bin number and wherein said step of using includes computing the starting time point and ending time point of said alert time window from said bin duration, said starting bin number and said ending bin number, prior to said starting of said alert time window.

11. The method according to claim 1 wherein said set of timing parameters comprises a set of approximation parameters and wherein said processing of said step of providing comprises using an approximation method to process said data collected from said heart in said data collection session to obtain a plurality of sets of approximation parameters, usable for computing improved approximated values of the beginning time point and the ending time point of said alert time window.

12. The method according to claim 11 wherein said approximation method is a linear piecewise approximation method, said set of approximation parameters comprises a beginning time point parameter and a first slope parameter associated with said beginning time point parameter, an ending time point parameter and a second slope parameter associated with said ending time point parameter, and wherein said step of using comprises computing an approximated beginning time point for said alert time window of said current beat cycle from the values of the current cycle length measured for said current beat cycle, said first slope parameter and said beginning time point parameter, and computing an approximated ending time point for said alert time window of said current beat cycle from the values of said current cycle length, said second slope parameter and said ending time point parameter.

13. The method according to claim 12 wherein said current cycle length is the instantaneous cycle length determined from the current R—R interval or the current A—A interval measured for said current beat cycle.

14. The method according to claim 12 wherein said current cycle length is an average cycle length computed from the values of a plurality of consecutive R—R intervals including the R—R interval of said current beat cycle.

15. The method according to claim 12 wherein said current cycle length is an average cycle length computed from the values of a plurality of consecutive A—A intervals including the A—A interval of said current beat cycle.

16. The method according to claim 1 wherein said set of timing parameters comprises said beginning time point and said ending time point of said alert time window.

17. The method according to claim 1 wherein said set of data is a degenerate set of data in which at least some of said sets of alert time window parameters of said plurality of sets of alert time window parameters have identical values of said set of timing parameters.

18. The method according to claim 1 wherein said first cardiac site is the right ventricle of said heart and said second cardiac site is the left ventricle of said heart.

19. The method according to claim 1 wherein said first cardiac site is the right atrium of said heart and said second cardiac site is the left ventricle of said heart.

20. A method for setting the parameters of an alert time window in an excitable tissue control device operative under a plurality of different cardiac conditions of a heart of a patient, the method comprising the steps of:
providing said excitable tissue control device with a set of data, said set of data comprises a plurality of sets of alert time window parameters, each set of alert time window parameters is uniquely associated with a different set of values of a plurality of cardiac condition defining parameters identifying one of said plurality of different cardiac conditions, each set of alert time window parameters of said plurality of sets of alert time window parameters comprises at least a set of timing parameters usable for obtaining a beginning time point and an ending time point for said alert time window, each set of alert time window parameters of said plurality of sets of alert time window parameters is obtained by processing data collected from a plurality of cardiac beats of said heart of said patient under said plurality of different cardiac conditions within a data collection session prior to said step of providing;
updating for a current beat cycle of said heart the values of a plurality of cardiac condition defining variables corresponding to said cardiac condition defining parameters;
automatically selecting for said current beat cycle a current set of alert time window parameters of said plurality of sets of alert time window parameters based on the current values of said cardiac condition defining variables;
using, for said current beat cycle, said current set of alert time window parameters selected in said step of automatically selecting to start and terminate said alert time window based on the time of detecting a first depolarization event at or about a first cardiac site;
detecting within the duration of said alert time window of said current beat cycle a second depolarization event at a second cardiac site of said heart; and
triggering the delivery of a delayed non-excitatory excitable tissue control signal at or about said second cardiac site based on the time of detection of said second depolarization event.

21. The method according to claim 20 wherein each set of alert time window parameters of said plurality of sets of alert time window parameters further comprises at least one detection sensitivity parameter having a value representing a detection sensitivity level, and wherein said step of using further includes using said value of said detection sensitivity parameter to set the detection sensitivity level of said excitable tissue control device for said current beat cycle.

22. The method according to claim 21 wherein said at least one detection sensitivity parameter comprises a voltage threshold level.

23. The method according to claim 21 wherein said at least one detection sensitivity parameter comprises at least one morphological detection parameter.

24. The method according to claim 21 wherein said set of data is a degenerate set of data in which at least some of said sets of alert time window parameters of said plurality of sets of alert time window parameters have identical values of said at least one detection sensitivity parameter.

25. The method according to claim 20 wherein said plurality of cardiac condition defining parameters comprises a cycle length category parameter, said cycle length category parameter has a value selected from a plurality of preset values each one of said plurality of preset values represents a different range of beat cycle lengths, one of said plurality of cardiac condition defining variables is a cycle length category variable, and wherein said step of updating includes updating the value of said cycle length category variable by determining the cycle length range into which the current measured beat to beat time interval falls and by setting as the value of said cycle length category variable one of said plurality of preset values corresponding with said cycle length range.

26. The method according to claim 20 wherein said plurality of cardiac conditions comprises beats initiated by the natural pacemaker of said heart and beats initiated by a pacing pulse delivered by said excitable tissue control device, one of said plurality of cardiac condition defining parameters is a parameter which may have a first value defining beats initiated by the natural pacemaker of said heart or a second value defining beats initiated by a pacing pulse delivered by said excitable tissue control device, and wherein one of said plurality of cardiac condition defining variables is a variable which may have the said first value defining a current beat initiated by the natural pacemaker of said heart or the said second value defining a current beat initiated by a pacing pulse delivered by said excitable tissue control device.

27. The method according to claim 20 wherein said plurality of cardiac conditions further comprises beats occurring during a time period in which the prior application of excitable tissue control signals results in a change of the velocity of propagation of a depolarization wave in at least a portion of the myocardial tissue disposed between said first cardiac site and said second cardiac site of said heart, and beats occurring during a time period in which the prior application of excitable tissue control signals does not result in a change in the velocity of propagation of a depolarization wave in said portion of the myocardial tissue disposed between said first cardiac site and said second cardiac site of said heart.

28. The method according to claim 20 wherein said set of timing parameters of said alert time window parameters comprises a beginning time point value and an ending time point value for an alert time window.

29. The method according to claim 20 wherein said excitable tissue control device is provided with a value of the bin duration of a time bin used for collecting data within said data collection session, said set of timing parameters of said alert time window parameters comprises a starting bin number and an ending bin number and wherein said step of using includes computing the starting time point and ending time point of said alert time window from said bin duration, said starting bin number and said ending bin number prior to said starting of said alert time window.

30. The method according to claim 20 wherein said set of timing parameters comprises a set of approximation parameters and wherein said processing of said step of providing comprises using an approximation method to process said data collected from said heart in said data collection session to obtain a plurality of sets of approximation parameters, usable for computing improved approximated values of the beginning time point and the ending time point of said alert time window.

31. The method according to claim 30 wherein said approximation method is a linear piecewise approximation method, said set of approximation parameters comprises a beginning time point parameter and a first slope parameter associated with said beginning time point parameter, an ending time point parameter and a second slope parameter associated with said ending time point parameter, and wherein said step of using comprises computing an approximated beginning time point for said alert time window of said current beat cycle from the values of the current cycle length, said first slope parameter and said beginning time point parameter, and computing an approximated ending time point for said alert time window of said current beat cycle from the values of said current cycle length, said second slope parameter and said ending time point parameter.

32. The method according to claim 31 wherein said current cycle length is the instantaneous cycle length determined from the current R—R interval or the current A—A interval measured for said current beat cycle.

33. The method according to claim 31 wherein said current cycle length is an average cycle length computed from the values of a plurality of consecutive R—R intervals including the R—R interval of said current beat cycle.

34. The method according to claim 31 wherein said current cycle length is an average cycle length computed from the values of a plurality of consecutive A—A intervals including the A—A interval of said current beat cycle.

35. The method according to claim 20 wherein said set of timing parameters comprises said beginning time point and said ending time point of said alert time window.

36. The method according to claim 20 wherein said set of data is a degenerate set of data in which the values of said set of timing parameters of at least some of the sets of said plurality of sets of alert time window parameters are identical.

37. The method according to claim 20 wherein said first cardiac site is the right ventricle of said heart and said second cardiac site is the left ventricle of said heart.

38. The method according to claim 20 wherein said first cardiac site is the right atrium of said heart and said second cardiac site is the left ventricle of said heart.

39. An excitable tissue control device for setting on a beat by beat basis the parameters of an alert time window under a plurality of different cardiac conditions of a heart of a patient, the device comprising:

a plurality of electrodes adapted to be implanted in or about said heart;

detection circuitry for detecting electrical depolarization events in a first cardiac site through at least a first electrode of said plurality of electrodes, said at least first electrode is disposed in or about said first cardiac site, and for detecting electrical depolarization events in a second cardiac site through at least a second electrode of said plurality of electrodes, said at least second electrode is disposed in or about said second cardiac site;

an excitable tissue control unit for delivering non-excitatory excitable tissue control signals to at least part of said second cardiac site through one or more electrodes of said plurality of electrodes;

a memory unit for storing a set of data, said set of data comprises a plurality of sets of alert time window parameters, each set of alert time window parameters is uniquely associated with a different set of values of a plurality of cardiac condition defining parameters identifying one of said plurality of different cardiac conditions, each set of alert time window parameters comprises at least a set of timing parameters usable for obtaining a beginning time point and an ending time point for said alert time window, each set of alert time window parameters is obtained by processing data collected from a plurality of cardiac beats of said heart of said patient under said plurality of different cardiac conditions within a data collection session performed in said patient;

a processor unit operatively connected to said detection circuitry, said excitable tissue control unit and said memory unit, for receiving detection signals from said detection circuitry, for controlling said excitable tissue control unit by using the received detection signals, for updating in a current beat cycle of said heart the values of a plurality of cardiac condition defining variables corresponding to said cardiac condition defining parameters, for automatically selecting for said current beat cycle a current set of alert time window parameters of said plurality of sets of alert time window parameters based on the current values of said cardiac condition defining variables, for applying said current set of alert time window parameters to start said alert time window within said current beat cycle after detecting a first depolarization event at or about said first cardiac site and to terminate said alert time window, and for initiating the delivery of a delayed excitable tissue control signal at or about said second cardiac site upon detecting within the duration of said alert time window a depolarization event in or about said second cardiac site of said heart; and a power source for providing power to said detection circuitry, said processor unit said memory unit and said excitable tissue control unit.

40. The device according to claim 39 further including a telemetry unit operatively connected to said power source and said processor unit for telemetrically receiving data from a second telemetry unit disposed outside said patient.

41. The device according to claim 39 wherein said plurality of sets of alert time window parameters of said set of data are stored in said memory unit as a data array or a look up table.

42. The device according to claim 39 wherein said detection circuitry is adapted for being controllably switched between a plurality of detection sensitivity levels, and wherein each set of alert time window parameters of said plurality of sets of alert time window parameters further comprises at least one detection sensitivity parameter having a value representing one of said plurality of detection sensitivity levels of said detection circuitry, and wherein said processor unit is adapted for using said value of said at least one detection sensitivity parameter of said current beat cycle to switch said detection circuitry to a detection sensitivity level represented by said at least one detection sensitivity parameter of said current beat cycle.

43. The device according to claim 42 wherein said detection circuitry is adapted for being switched between a plurality of voltage threshold levels and said at least one detection sensitivity parameter comprises a voltage threshold level.

44. The device according to claim 42 wherein said detection circuitry is adapted for performing event detection based on a morphological detection method and wherein said at least one detection sensitivity parameter comprises at least one morphological detection parameter.

45. The device according to claim 40 wherein said set of data is a degenerate set of data in which at least some of said sets of alert time window parameters of said plurality of sets of alert time window parameters have identical values of said at least one detection sensitivity parameter.

46. The device according to claim 39 wherein said plurality of cardiac conditions comprises beats having a plurality of different beat to beat time intervals representing different instantaneous heart rates of said heart.

47. The device according to claim 46 wherein said plurality of cardiac conditions further comprises beats occurring during a time period in which the prior application of excitable tissue control signals results in a change of the velocity of propagation of a depolarization wave in at least a portion of the myocardial tissue disposed between said first cardiac site and said second cardiac site of said heart, and beats occurring during a time period in which the prior application of excitable tissue control signals does not result in a change in the velocity of propagation of a depolarization wave in at least a portion of the myocardial tissue disposed between said first cardiac site and said second cardiac site of said heart.

48. The device according to claim 39 wherein said plurality of cardiac conditions comprises beats occurring during a time period in which the prior application of excitable tissue control signals results in a change of the velocity of propagation of a depolarization wave in at least a portion of the myocardial tissue disposed between said first cardiac site and said second cardiac site of said heart, and beats occurring during a time period in which the prior application of excitable tissue control signals does not result in a change in the velocity of propagation of a depolarization wave in at least a portion of the myocardial tissue disposed between said first cardiac site and said second cardiac site of said heart.

49. The device according to claim 39 further including a pacing unit operatively connected to said power source, said processor unit and to at least one electrode of said plurality of electrodes for delivering pacing pulses to said heart through said at least one electrode.

50. The device according to claim 49 wherein said plurality of cardiac conditions comprises beats initiated by the natural pacemaker of said heart and beats initiated by a pacing pulse delivered by said excitable tissue control device.

51. The device according to claim 50 wherein said plurality of cardiac conditions further comprise beats having a plurality of different beat to beat time intervals representing different instantaneous heart rates of said heart.

52. The device according to claim 51 wherein said plurality of cardiac conditions further comprises beats occurring during a time period in which the prior application of excitable tissue control signals results in a change of the velocity of propagation of a depolarization wave in at least a portion of the myocardial tissue disposed between said first cardiac site and said second cardiac site of said heart, and beats occurring during a time period in which the prior application of excitable tissue control signals does not result in a change in the velocity of propagation of a depolarization wave in at least a portion of the myocardial tissue disposed between said first cardiac site and said second cardiac site of said heart.

53. The device according to claim 39 wherein said set of timing parameters of said alert time window parameters comprises a beginning time point value and an ending time point value for said alert time window.

54. The device according to claim 39 wherein said excitable tissue control device is provided with a value of the bin duration of a time bin used for collecting data within said data collection session, said value is stored in said memory unit, wherein said set of timing parameters of said alert time window parameters comprises a starting bin number and an ending bin number and wherein said processor unit is adapted for computing the starting time point and ending time point of said alert time window from said bin duration, said starting bin number and said ending bin number, prior to starting of said alert time window within said current beat cycle.

55. The device according to claim 39 wherein said set of timing parameters comprises a set of approximation parameters and wherein said processing comprises using an approximation method to process said data collected from said heart in said data collection session to obtain a plurality of sets of approximation parameters usable for computing improved approximated values of the beginning time point and the ending time point of said alert time window.

56. The device according to claim 55 wherein said approximation method is a linear piecewise approximation method, said set of approximation parameters comprises a beginning time point parameter and a first slope parameter associated with said beginning time point parameter, an ending time point parameter and a second slope parameter associated with said ending time point parameter, and wherein said step of using comprises computing an approximated beginning time point for said alert time window of said current beat cycle from the values of the current cycle length measured for said current beat cycle, said first slope parameter and said beginning time point parameter, and computing an approximated ending time point for said alert time window of said current beat cycle from the values of said current cycle length, said second slope parameter and said ending time point parameter.

57. The device according to claim 56 wherein said current cycle length is the instantaneous cycle length determined from the current R—R interval or the current A—A interval measured for said current beat cycle.

58. The device according to claim 56 wherein said current cycle length is an average cycle length computed from the values of a plurality of consecutive R—R intervals including the R—R interval of said current beat cycle.

59. The device according to claim 50 wherein said current cycle length is an average cycle length computed from the values of a plurality of consecutive A—A intervals including the A—A interval of said current beat cycle.

60. The device according to claim 39 wherein said set of timing parameters comprises said beginning time point and said ending time point of said alert time window.

61. The device according to claim 39 wherein said set of data is a degenerate set of data in which at least some of said sets of alert time window parameters of said plurality of sets of alert time window parameters have identical values of said set of timing parameters.

62. The device according to claim 39 wherein said first cardiac site is the right ventricle of said heart and said second cardiac site is the left ventricle of said heart.

63. The device according to claim 39 wherein said first cardiac site is the right atrium of said heart and said second cardiac site is the left ventricle of said heart.

64. The device according to claim 39 wherein said excitable tissue control device is adapted to be implanted in said patient.

65. The device according to claim 39 wherein said excitable tissue control device is disposed out of said patient and is operatively connected to said plurality of electrodes adapted to be implanted in or about said heart of said patient.

66. An excitable tissue control device for setting on a beat by beat basis the parameters of an alert time window under a plurality of different cardiac conditions of a heart of a patient, the device comprising:

a plurality of electrodes adapted to be implanted in or about said heart;

means for detecting electrical depolarization events in a first cardiac site through at least a first electrode of said plurality of electrodes, said at least first electrode is disposed in or about said first cardiac site, and for detecting electrical depolarization events in a second cardiac site through at least a second electrode of said plurality of electrodes, said at least second electrode is disposed in or about said second cardiac site;

excitable tissue control means for delivering non-excitatory excitable tissue control signals to at least part of said second cardiac site through one or more electrodes of said plurality of electrodes;

memory means for storing a set of data, said set of data comprises a plurality of sets of alert time window parameters, each set of alert time window parameters is uniquely associated with a different set of values of a plurality of cardiac condition defining parameters identifying one of said plurality of different cardiac conditions, each set of alert time window parameters comprises at least a set of timing parameters usable for obtaining a beginning time point and an ending time point for said alert time window, each set of alert time window parameters is obtained by processing data collected from a plurality of cardiac beats of said heart of said patient under said plurality of different cardiac conditions within a data collection session performed in said patient;

processing means operatively connected to said detection means, said excitable tissue control means and said memory means, for receiving detection signals from said detection means, for controlling said excitable tissue control means by using the received detection signals, for updating in a current beat cycle of said heart the values of a plurality of cardiac condition defining variables corresponding to said cardiac condition defining parameters, for automatically selecting for said current beat cycle a current set of alert time window parameters of said plurality of sets of alert time window parameters based on the current values of said cardiac condition defining variables, for applying said current set of alert time window parameters to start said alert time window within said current beat cycle after detecting a first depolarization event at or about said first cardiac site and to terminate said alert time window, and for initiating the delivery of a delayed excitable tissue control signal at or about said second cardiac site upon detecting within the duration of said alert time window a depolarization event in or about said second cardiac site of said heart; and a power source for providing power to said detection means, said processing means said memory means and said excitable tissue control means.

67. The device according to claim 66 further including telemetry means operatively connected to said power source and said processing means for telemetrically receiving data from a second telemetry means disposed outside said patient.

68. The device according to claim 66 further including pacing means operatively connected to said power source, said processing means and to at least one electrode of said plurality of electrodes, for delivering pacing pulses to said heart through said at least one electrode.

* * * * *